(12) United States Patent
Hatayama et al.

(10) Patent No.: US 11,414,475 B2
(45) Date of Patent: Aug. 16, 2022

(54) RECOMBINANT FCγRII

(71) Applicants: TOSOH CORPORATION, Yamaguchi (JP); SAGAMI CHEMICAL RESEARCH INSTITUTE, Kanagawa (JP)

(72) Inventors: Kouta Hatayama, Kanagawa (JP); Teruhiko Ide, Kanagawa (JP); Hiroyuki Ito, Kanagawa (JP); Yosuke Terao, Kanagawa (JP); Naoki Yamanaka, Kanagawa (JP); Satoshi Endo, Kanagawa (JP)

(73) Assignees: TOSOH CORPORATION, Yamaguchi (JP); SAGAMI CHEMICAL RESEARCH INSTITUTE, Kanagawa (JP)

( * ) Notice: Subject to any disclaimer, the term of this patent is extended or adjusted under 35 U.S.C. 154(b) by 814 days.

(21) Appl. No.: 16/335,519

(22) PCT Filed: Sep. 21, 2017

(86) PCT No.: PCT/JP2017/034152
§ 371 (c)(1),
(2) Date: Mar. 21, 2019

(87) PCT Pub. No.: WO2018/056374
PCT Pub. Date: Mar. 29, 2018

(65) Prior Publication Data
US 2019/0233499 A1    Aug. 1, 2019

(30) Foreign Application Priority Data

Sep. 23, 2016 (JP) .............................. JP2016-185717
Sep. 23, 2016 (JP) .............................. JP2016-185718

(51) Int. Cl.
| | | |
|---|---|---|
| C07K 1/00 | (2006.01) | |
| C07K 14/735 | (2006.01) | |
| C07K 1/22 | (2006.01) | |
| C07K 16/06 | (2006.01) | |
| C12N 1/20 | (2006.01) | |
| C12N 15/70 | (2006.01) | |
| C12P 21/02 | (2006.01) | |

(52) U.S. Cl.
CPC .......... C07K 14/70535 (2013.01); C07K 1/22 (2013.01); C07K 16/065 (2013.01); C12N 1/20 (2013.01); C12N 15/70 (2013.01); C12P 21/02 (2013.01)

(58) Field of Classification Search
CPC .............................................. C07K 14/70535
See application file for complete search history.

(56) References Cited

U.S. PATENT DOCUMENTS

| | | |
|---|---|---|
| 2005/0002924 A1 | 1/2005 | Huber et al. |
| 2013/0079499 A1 | 3/2013 | Hatayama et al. |
| 2016/0222081 A1 | 8/2016 | Asaoka et al. |
| 2017/0218044 A1 | 8/2017 | Asaoka et al. |

FOREIGN PATENT DOCUMENTS

| | | |
|---|---|---|
| CN | 105555801 A | 5/2016 |
| JP | 2002-531086 | 9/2002 |
| JP | 2005-515981 | 6/2005 |
| JP | 2011-105716 | 6/2011 |
| JP | 2012-188456 | 10/2012 |
| JP | 2017-178908 | 10/2017 |
| WO | 96/08512 A1 | 3/1996 |
| WO | 00/32767 | 6/2000 |
| WO | 2011/111393 | 9/2011 |
| WO | 2015/199154 | 12/2015 |

OTHER PUBLICATIONS

Powell et al., "Biochemical Analysis and Crystallisation of FcγRIIa, the Low Affinity Receptor for IgG" *Immunology Letters*, vol. 68, No. 1, pp. 17-23 (1999).
Extended European Search Report issued in EP Patent Application No. 17853142.2, dated Apr. 29, 2020.
Takai, *Jpn. J. Clin. Immunol.*, "Role of Fcγ Receptors in Immune Regulation and Diseases," vol. 28, No. 5, pp. 318-326 (2005).
Bruhns, "Properties of Mouse and Human IgG Receptors and Their Contribution to Disease Models," *Blood*, vol. 119, No. 24, pp. 5640-5649 (2012).
Ravetch et al., "Fc Receptors," *Annu. Rev. Immunol.*, vol. 9, pp. 457-492 (1991).
Sondermann et al., "Molecular Basis for Immune Complex Recognition: A Comparison of Fc-Receptor Structures" *J. Mol. Biol.*, vol. 309, pp. 737-749 (2001).
Jung et al., "Efficient Expression and Purification of Human Aglycosylated Fcγ Receptors in *Escherichia coli*," *Biotechnol. Bioeng.*, vol. 107, No. 1, pp. 21-30 (2010).

(Continued)

*Primary Examiner* — Albert M Navarro
(74) *Attorney, Agent, or Firm* — Greenblum & Bernstein, P.L.C.

(57) ABSTRACT

The problem to be addressed by the present invention is to provide improved recombinant FcγRIIb and FcγRIIa that do not require refolding and exhibit high productivity and thermal stability, and to provide a method for producing the same. Said problem is solved by improved recombinant FcγRIIb comprising at least the amino acid residues of the extracellular domain of human FcγRIIb (No. 43 to No. 215 in UniProt No. P31994), wherein, in said amino acid residues, at least one amino acid substitution has occurred at a position corresponding to No. 82, 94, 98, 104, 105, or 139 in UniProt No. P31994. Said problem is also solved by improved recombinant FcγRIIa comprising at least the amino acid residues of the extracellular domain of human FcγRIIa (No. 34 to No. 206 in UniProt No. P12318-1), wherein, in said amino acid residues, at least one amino acid substitution has occurred at a position corresponding to No. 73, 85, 89, 95, 96, or 130 in UniProt No. P12318-1.

10 Claims, 4 Drawing Sheets
Specification includes a Sequence Listing.

(56) References Cited

OTHER PUBLICATIONS

Yamaguchi et al., "Refolding Techniques for Recovering Biologically Active Recombinant Proteins from Inclusion Bodies," *Biomolecules*, vol. 4, pp. 235-251 (2014).

International Search Report issued in PCT/JP2017/034152, dated Dec. 19, 2017, along with an English-language translation.

FIG. 4

| | 29 | 30 | 43 | 58 | 60 | 61 | 135 | 158 | 162 | 163 | 166 | 191 |
|---|---|---|---|---|---|---|---|---|---|---|---|---|
| | Amino acid Nos. in SEQ ID NO:1 | | | | | | | | | | | |
| FcγRIIb (SEQ ID NO:1) | T | P | Q | R | T | H | V | K | R | S | N | Y |
| FcγRIIa (SEQ ID NO:88) | Q | A | P | Q | A | R | M | Q | H | L | T | F |

SEQUENCE LISTING

```
<160> NUMBER OF SEQ ID NOS: 176

<210> SEQ ID NO 1
<211> LENGTH: 209
<212> TYPE: PRT
<213> ORGANISM: Artificial Sequence
<220> FEATURE:
<223> OTHER INFORMATION: MalE signal - FcgRIIb - 6His

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
                20                  25                  30

Pro Pro Lys Ala Val Leu Lys Leu Glu Pro Gln Trp Ile Asn Val Leu
            35                  40                  45

Gln Glu Asp Ser Val Thr Leu Thr Cys Arg Gly Thr His Ser Pro Glu
    50                  55                  60

Ser Asp Ser Ile Gln Trp Phe His Asn Gly Asn Leu Ile Pro Thr His
65                  70                  75                  80

Thr Gln Pro Ser Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190
```

Ser Lys Pro Val Thr Ile Thr Val Gln Gly Gly His His His His
    195                 200                 205

His

<210> SEQ ID NO 2
<211> LENGTH: 209
<212> TYPE: PRT
<213> ORGANISM: Artificial Sequence
<220> FEATURE:
<223> OTHER INFORMATION: MalE signal - FcgRIIb-a4F3 - 6His

<400> SEQUENCE: 2

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Ile Gln Trp Phe His Asn Gly Asn Leu Ile Pro Thr His
65                  70                  75                  80

Thr Gln Pro Thr Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His
    195                 200                 205

His

<210> SEQ ID NO 3
<211> LENGTH: 209
<212> TYPE: PRT
<213> ORGANISM: Artificial Sequence
<220> FEATURE:
<223> OTHER INFORMATION: MalE signal - FcgRIIb-a2E2 - 6His

<400> SEQUENCE: 3

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Ile Gln Trp Phe His Asn Gly Asn Leu Ile Pro Thr His

```
                65                  70                  75                  80
            Thr Gln Pro Ser Tyr Arg Phe Lys Ala Asn Asn Asn Asp Ser Gly Glu
                            85                  90                  95
            Tyr Thr Cys Gln Thr Gly Gln Thr Ser Leu Ser Asp Pro Val His Leu
                           100                 105                 110
            Thr Val Leu Ser Glu Trp Leu Val Leu Gln Thr Pro Arg Leu Glu Phe
                           115                 120                 125
            Gln Glu Gly Glu Thr Ile Val Leu Arg Cys His Ser Trp Lys Asp Lys
                           130                 135                 140
            Pro Leu Val Lys Val Thr Phe Phe Gln Asn Gly Lys Ser Lys Lys Phe
            145                 150                 155                 160
            Ser Arg Ser Asp Pro Asn Phe Ser Ile Pro Gln Ala Asn His Ser His
                           165                 170                 175
            Ser Gly Asp Tyr His Cys Thr Gly Asn Ile Gly Tyr Thr Leu Tyr Ser
                           180                 185                 190
            Ser Lys Pro Val Thr Ile Thr Val Gln Gly Gly His His His His His
                           195                 200                 205
            His

<210> SEQ ID NO 4
<211> LENGTH: 209
<212> TYPE: PRT
<213> ORGANISM: Artificial Sequence
<220> FEATURE:
<223> OTHER INFORMATION: MalE signal - FcgRIIb-a15A6 - 6His

<400> SEQUENCE: 4

Met Lys Ile Lys Thr Gly Ala Arg Ile Leu Ala Leu Ser Ala Leu Thr
1               5                   10                  15
Thr Met Met Phe Ser Ala Ser Ala Leu Ala Met Gly Thr Pro Ala Ala
                20                  25                  30
Pro Pro Lys Ala Val Leu Lys Leu Glu Pro Gln Trp Ile Asn Val Leu
            35                  40                  45
Gln Glu Asp Ser Val Thr Leu Thr Cys Arg Gly Thr His Ser Pro Glu
50                  55                  60
Ser Asp Ser Val Gln Trp Phe His Asn Gly Asn Leu Ile Pro Thr His
65                  70                  75                  80
Thr Gln Pro Ser Tyr Arg Phe Lys Ala Asn Asn Asn Asp Ser Gly Glu
                85                  90                  95
Tyr Thr Cys Gln Thr Gly Gln Thr Ser Leu Ser Asp Pro Val His Leu
            100                 105                 110
Thr Val Leu Ser Glu Trp Leu Val Leu Gln Thr Pro His Leu Glu Phe
            115                 120                 125
Gln Glu Gly Glu Thr Ile Val Leu Arg Cys His Ser Trp Lys Asp Lys
            130                 135                 140
Pro Leu Val Lys Val Thr Phe Phe Gln Asn Gly Lys Ser Lys Lys Phe
145                 150                 155                 160
Ser Arg Ser Asp Pro Asn Phe Ser Ile Pro Gln Ala Asn His Ser His
            165                 170                 175
Ser Gly Asp Tyr His Cys Thr Gly Asn Ile Gly Tyr Thr Leu Tyr Ser
            180                 185                 190
Ser Lys Pro Val Thr Ile Thr Val Gln Gly Gly His His His His His
            195                 200                 205
His
```

```
<210> SEQ ID NO 5
<211> LENGTH: 209
<212> TYPE: PRT
<213> ORGANISM: Artificial Sequence
<220> FEATURE:
<223> OTHER INFORMATION: MalE signal - FcgRIIb-m3 - 6His

<400> SEQUENCE: 5

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
                20                  25                  30

Pro Pro Lys Ala Val Leu Lys Leu Glu Pro Gln Trp Ile Asn Val Leu
            35                  40                  45

Gln Glu Asp Ser Val Thr Leu Thr Cys Arg Gly Thr His Ser Pro Glu
    50                  55                  60

Ser Asp Ser Val Gln Trp Phe His Asn Gly Asn Leu Ile Pro Thr His
65                  70                  75                  80

Thr Gln Pro Thr Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His

<210> SEQ ID NO 6
<211> LENGTH: 209
<212> TYPE: PRT
<213> ORGANISM: Artificial Sequence
<220> FEATURE:
<223> OTHER INFORMATION: MalE signal - FcgRIIb-d10D5 - 6His

<400> SEQUENCE: 6

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
                20                  25                  30

Pro Pro Lys Ala Val Leu Lys Leu Glu Pro Gln Trp Ile Asn Val Leu
            35                  40                  45

Gln Glu Asp Ser Val Thr Leu Thr Cys Arg Gly Thr His Ser Pro Glu
    50                  55                  60

Ser Asp Ser Val Gln Trp Phe His Asn Gly Asn Leu Ile Pro Thr His
65                  70                  75                  80

Thr Gln Pro Thr Tyr Arg Phe Lys Ala Asn Ser Asn Asp Ser Gly Glu
                85                  90                  95
```

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His

<210> SEQ ID NO 7
<211> LENGTH: 209
<212> TYPE: PRT
<213> ORGANISM: Artificial Sequence
<220> FEATURE:
<223> OTHER INFORMATION: MalE signal - FcgRIIb-d11D7 - 6His

<400> SEQUENCE: 7

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Val Gln Trp Phe His Asn Gly Asn Leu Ile Pro Thr His
65                  70                  75                  80

Thr Gln Pro Thr Tyr Arg Phe Lys Ala Thr Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His

<210> SEQ ID NO 8
<211> LENGTH: 209
<212> TYPE: PRT
<213> ORGANISM: Artificial Sequence
<220> FEATURE:
<223> OTHER INFORMATION: MalE signal - FcgRIIb-d6E2 - 6His

<400> SEQUENCE: 8

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
50                  55                  60

Ser Asp Ser Val Gln Trp Phe His Asn Gly Asn Leu Ile Pro Thr Gln
65                  70                  75                  80

Thr Gln Pro Thr Tyr Arg Phe Lys Ala Asn Asn Asn Asp Ser Gly Glu
            85                  90                  95

Tyr Thr Cys Gln Thr Gly Gln Thr Ser Leu Ser Asp Pro Val His Leu
        100                 105                 110

Thr Val Leu Ser Glu Trp Leu Val Leu Gln Thr Pro Arg Leu Glu Phe
    115                 120                 125

Gln Glu Gly Glu Thr Ile Val Leu Arg Cys His Ser Trp Lys Asp Lys
130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
            165                 170                 175

Ser Gly Asp Tyr His Cys Thr Gly Asn Ile Gly Tyr Thr Leu Tyr Ser
        180                 185                 190

Ser Lys Pro Val Thr Ile Thr Val Gln Gly Gly His His His His His
    195                 200                 205

His

<210> SEQ ID NO 9
<211> LENGTH: 209
<212> TYPE: PRT
<213> ORGANISM: Artificial Sequence
<220> FEATURE:
<223> OTHER INFORMATION: MalE signal - FcgRIIb-m5b - 6His

<400> SEQUENCE: 9

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
50                  55                  60

Ser Asp Ser Val Gln Trp Phe His Asn Gly Asn Leu Ile Pro Thr Gln
65                  70                  75                  80

Thr Gln Pro Thr Tyr Arg Phe Lys Ala Asn Ser Asn Asp Ser Gly Glu
            85                  90                  95

Tyr Thr Cys Gln Thr Gly Gln Thr Ser Leu Ser Asp Pro Val His Leu
        100                 105                 110

Thr Val Leu Ser Glu Trp Leu Val Leu Gln Thr Pro Arg Leu Glu Phe
    115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His
        195                 200                 205

His

<210> SEQ ID NO 10
<211> LENGTH: 209
<212> TYPE: PRT
<213> ORGANISM: Artificial Sequence
<220> FEATURE:
<223> OTHER INFORMATION: MalE signal - FcgRIIb-m5c - 6His

<400> SEQUENCE: 10

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Val Gln Trp Phe His Asn Gly Asn Leu Ile Pro Thr His
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His
        195                 200                 205

His

<210> SEQ ID NO 11
<211> LENGTH: 209
<212> TYPE: PRT
<213> ORGANISM: Artificial Sequence
<220> FEATURE:
<223> OTHER INFORMATION: MalE signal - FcgRIIb-m6b - 6His

<400> SEQUENCE: 11

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
                20                  25                  30

Pro Pro Lys Ala Val Leu Lys Leu Glu Pro Gln Trp Ile Asn Val Leu
            35                  40                  45

Gln Glu Asp Ser Val Thr Leu Thr Cys Arg Gly Thr His Ser Pro Glu
50                  55                  60

Ser Asp Ser Val Gln Trp Phe His Asn Gly Asn Leu Ile Pro Thr Gln
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
                100                 105                 110

Thr Val Leu Ser Glu Trp Leu Val Leu Gln Thr Pro Arg Leu Glu Phe
            115                 120                 125

Gln Glu Gly Glu Thr Ile Val Leu Arg Cys His Ser Trp Lys Asp Lys
130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
                180                 185                 190

Ser Lys Pro Val Thr Ile Thr Val Gln Gly His His His His
            195                 200                 205

His

<210> SEQ ID NO 12
<211> LENGTH: 310
<212> TYPE: PRT
<213> ORGANISM: Homo sapiens
<300> PUBLICATION INFORMATION:
<308> DATABASE ACCESSION NUMBER: UniProt P31994
<309> DATABASE ENTRY DATE: 2000-05-30
<313> RELEVANT RESIDUES IN SEQ ID NO: (1)..(310)

<400> SEQUENCE: 12

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
                20                  25                  30

Ala Val Leu Phe Leu Ala Pro Val Ala Gly Thr Pro Ala Ala Pro Pro
            35                  40                  45

Lys Ala Val Leu Lys Leu Glu Pro Gln Trp Ile Asn Val Leu Gln Glu
50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
                100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
130                 135                 140
```

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
            165                 170                 175

Ser Asp Pro Asn Phe Ser Ile Pro Gln Ala Asn His Ser His Ser Gly
        180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
            245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300

Asp Asp Gln Asn Arg Ile
305                 310

<210> SEQ ID NO 13
<211> LENGTH: 627
<212> TYPE: DNA
<213> ORGANISM: Artificial Sequence
<220> FEATURE:
<223> OTHER INFORMATION: DNA encoding MalE signal - FcgRIIb-a4F3 - 6His

<400> SEQUENCE: 13
atgaaaataa aaacaggtgc acgcatcctc gcattatccg cattaacgac gatgatgttt      60
tccgcctcgg ctctcgccat gggaactccc gcagcgcctc aaaggcggt tctgaaactg      120 gagccgcagt ggattaatgt gttgcaggaa gatagcgtga cgctgacctg ccgtggaacc      180
catagcccgg aatcagacag catacagtgg tttcacaacg gcaatttgat ccccactcat      240
acgcagccga cgtaccgttt caaagccaac aataacgatt cgggcgaata cctgccag       300 acaggccaga ccagcctgag cgatccagtg cacctgaccg tgctgtcaga atggctggtg      360
ctgcaaaccc cgcatctgga atttcaggaa ggcgaaacca tagtgctgcg ttgccacagc      420
tggaaagata aaccgctggt gaaggtcacg ttcttccaga acgggaagag caagaagttc      480
tcccgtagcg acccgaattt tagcatcccc caggcgaatc atagccatag cggcgattat      540
cactgcaccg ggaatattgg gtatacgttg tatagcagca agccggttac tatcaccgtg      600
cagggcggcc atcatcatca tcatcat                                         627

<210> SEQ ID NO 14
<211> LENGTH: 627
<212> TYPE: DNA
<213> ORGANISM: Artificial Sequence
<220> FEATURE:
<223> OTHER INFORMATION: DNA encoding MalE signal - FcgRIIb-a2E2 - 6His

<400> SEQUENCE: 14
atgaaaataa aaacaggtgc acgcatcctc gcattatccg cattaacgac gatgatgttt      60
tccgcctcgg ctctcgccat gggaactccc gcagcgcctc aaaggcggt tctgaaactg      120

```
gagccgcagt ggattaatgt gttgcaggaa gatagcgtga cgctgacctg ccgtggaacc      180
catagcccgg aatcagacag catacagtgg tttcacaacg gcaatttgat ccccactcat      240
acgcagccgt cgtaccgttt caaagccaac aataacgatt cgggcgaata tacctgccag      300
acaggccaga ccagcctgag cgatccagtg cacctgaccg tgctgtcaga atggctggtg      360
ctgcaaaccc cgcgtctgga atttcaggaa ggcgaaacca tagtgctgcg ttgccacagc      420
tggaaagata aaccgctggt gaaggtcacg ttcttccaga acgggaagag caagaagttc      480
tcccgtagcg acccgaattt tagcatcccc caggcgaatc atagccatag cggcgattat      540
cactgcaccg ggaatattgg gtatacgttg tatagtagca agccggttac tatcaccgtg      600
cagggcggcc atcatcatca tcatcat                                          627

<210> SEQ ID NO 15
<211> LENGTH: 627
<212> TYPE: DNA
<213> ORGANISM: Artificial Sequence
<220> FEATURE:
<223> OTHER INFORMATION: DNA encoding MalE signal - FcgRIIb-a15A6 - 6His

<400> SEQUENCE: 15
atgaaaataa aaacaggtgc acgcatcctc gcattatccg cattaacgac gatgatgttt      60
tccgcctcgg ctctcgccat gggaactccc gcagcgcctc caaaggcggt tctgaaactg      120
gagccgcagt ggattaatgt gttgcaggaa gatagcgtga cgctgacctg ccgaggaacc      180
catagcccgg aatcagacag cgtacagtgg tttcacaacg gcaatttgat ccccactcat      240
acgcagccgt cgtaccgttt caaagccaac aataacgatt cgggcgaata tacctgccag      300
acaggccaga ccagcctgag cgatccagtg cacctgaccg tgctgtcaga atggctggtg      360
ctgcaaaccc cgcatctgga atttcaggaa ggcgaaacca tagtgctgcg ttgccacagc      420
tggaaggata aaccgctggt gaaggtcacg ttcttccaga acgggaagag caagaagttc      480
tcccgtagcg acccgaattt tagcatcccc caggcgaatc atagccatag cggcgattat      540
cactgcaccg ggaatattgg gtatacgttg tatagcagca agccggttac tatcaccgtg      600
cagggcggcc atcatcatca tcatcat                                          627

<210> SEQ ID NO 16
<211> LENGTH: 627
<212> TYPE: DNA
<213> ORGANISM: Artificial Sequence
<220> FEATURE:
<223> OTHER INFORMATION: DNA encoding MalE signal - FcgRIIb-m3 - 6His

<400> SEQUENCE: 16
atgaaaataa aaacaggtgc acgcatcctc gcattatccg cattaacgac gatgatgttt      60
tccgcctcgg ctctcgccat gggaactccc gcagcgcctc caaaggcggt tctgaaactg      120
gagccgcagt ggattaatgt gttgcaggaa gatagcgtga cgctgacctg ccgtggaacc      180
catagcccgg aatcagacag cgtacagtgg tttcacaacg gcaatttgat ccccactcat      240
acgcagccga cgtaccgttt caaagccaac aataacgatt cgggcgaata tacctgccag      300
acaggccaga ccagcctgag cgatccagtg cacctgaccg tgctgtcaga atggctggtg      360
ctgcaaaccc cgcgtctgga atttcaggaa ggcgaaacca tagtgctgcg ttgccacagc      420
tggaaagata aaccgctggt gaaggtcacg ttcttccaga acgggaagag caagaagttc      480
tcccgtagcg acccgaattt tagcatcccc caggcgaatc atagccatag cggcgattat      540
```
cactgcaccg ggaatattgg gtatacgttg tatagcagca agccggttac tatcaccgtg      600
cagggcggcc atcatcatca tcatcat                                          627

<210> SEQ ID NO 17
<211> LENGTH: 627
<212> TYPE: DNA
<213> ORGANISM: Artificial Sequence
<220> FEATURE:
<223> OTHER INFORMATION: DNA encoding MalE signal - FcgRIIb-m3 - 6His

<400> SEQUENCE: 17
atgaaaataa aaacaggtgc acgcatcctc gcattatccg cattaacgac gatgatgttt      60
tccgcctcgg ctctcgccat gggaactccc gcagcgcctc caaaggcggt tctgaaactg     120
gagccgcagt ggattaatgt gttgcaggaa gatagcgtga cgctgacctg ccgtggaacc     180
catagcccgg aatcagacag cgtacagtgg tttcacaacg gcaatttgat ccccactcat     240
acgcagccga cgtaccgttt caaagccaac aataacgatt cgggcgaata tacctgccag     300
acaggccaga ccagcctgtc ggatccagtg cacctgaccg tgctgtcaga atggctggtg     360
ctgcaaaccc cgcgtctgga atttcaggaa ggcgaaacca tagtgctgcg ttgccacagc     420
tggaaagata aaccgctggt gaaggtcacg ttcttccaga acgggaagag caagaagttc     480
tcccgtagcg acccgaattt tagcatcccc caggcgaatc atagccatag cggcgattat     540
cactgcaccg ggaatattgg gtatacgttg tatagcagca agccggttac tatcaccgtg     600
cagggcggcc atcatcatca tcatcat                                          627

<210> SEQ ID NO 18
<211> LENGTH: 627
<212> TYPE: DNA
<213> ORGANISM: Artificial Sequence
<220> FEATURE:
<223> OTHER INFORMATION: DNA encoding MalE signal - FcgRIIb-d10D5 - 6His

<400> SEQUENCE: 18
atgaaaataa aaacaggtgc acgcatcctc gcattatccg cattaacgac gatgatgttt      60
tccgcctcgg ctctcgccat gggaactccc gcagcgcctc caaaggcggt tctgaaactg     120
gagccgcagt ggattaatgt gttgcaggaa gatagcgtga cgctgacctg ccgtggaacc     180
catagcccgg aatcagacag cgtacagtgg tttcacaacg gcaatttgat ccccactcat     240
acgcagccga cgtaccgttt caaagccaac agtaacgatt cgggcgaata tacctgccag     300
acaggccaga ccagcctgtc ggatccagtg cacctgaccg tgctgtcaga atggctggtg     360
ctgcaaaccc cgcgtctgga atttcaggaa ggcgaaacca tagtgctgcg ttgccacagc     420
tggaaagata aaccgctggt gaaggtcacg ttcttccaga acgggaagag caagaagttc     480
tcccgtagcg acccgaattt tagcatcccc caggcgaatc atagccatag cggcgattat     540
cactgcaccg ggaatattgg gtatacgttg tatagcagca agccggttac tatcaccgtg     600
cagggcggcc atcatcatca tcatcat                                          627

<210> SEQ ID NO 19
<211> LENGTH: 627
<212> TYPE: DNA
<213> ORGANISM: Artificial Sequence
<220> FEATURE:
<223> OTHER INFORMATION: DNA encoding MalE signal - FcgRIIb-d11D7 - 6His

<400> SEQUENCE: 19
atgaaaataa aaacaggtgc acgcatcctc gcattatccg cattaacgac gatgatgttt      60

```
tccgcctcgg ctctcgccat gggaactccc gcagcgcctc caaaggcggt tctgaaactg    120
gagccgcagt ggattaatgt gttgcaggaa gatagcgtga cgctgacctg ccgtggaacc    180
catagcccgg aatcagacag cgtacagtgg tttcacaacg gcaatttgat ccccactcat    240
acgcagccga cgtatcgttt caaagccacc aataacgatt cgggcgaata tacctgccag    300
acaggccaga ccagcctgtc ggatccagtg cacctgaccg tgctgtcaga atggctggtg    360
ctgcaaaccc cgcgtctgga atttcaggaa ggcgaaacca tagtgctgcg ttgccacagc    420
tggaaagata aaccgctggt gaaggtcacg ttcttccaga acgggaagag caagaagttc    480
tcccgtagcg acccgaattt tagcatcccc caggcgaatc atagccatag cggcgattat    540
cactgcaccg ggaatattgg gtatacgttg tatagcagca agccggttac tatcaccgtg    600
cagggcggcc atcatcatca tcatcat                                       627
```

<210> SEQ ID NO 20
<211> LENGTH: 627
<212> TYPE: DNA
<213> ORGANISM: Artificial Sequence
<220> FEATURE:
<223> OTHER INFORMATION: DNA encoding MalE signal - FcgRIIb-d11D7 - 6His

<400> SEQUENCE: 20

```
atgaaaataa aaacaggtgc acgcatcctc gcattatccg cattaacgac gatgatgttt     60
tccgcctcgg ctctcgccat gggaactccc gcagcgcctc caaaggcggt tctgaaactg    120
gagccgcagt ggattaatgt gttgcaggaa gatagcgtga cgctgacctg ccgtggaacc    180
catagcccgg aatcagacag cgtacagtgg tttcacaacg gcaatttgat ccccactcaa    240
acgcagccga cgtaccgttt caaagccaac aataacgatt cgggcgaata tacctgccag    300
acaggccaga ccagcctgtc ggatccagtg cacctgaccg tgctgtcaga atggctggtg    360
ctgcaaaccc cgcgtctgga atttcaggaa ggcgaaacca tagtgctgcg ttgccacagc    420
tggaaagata aaccgctggt gaaggtcacg ttcttccaga acgggaagag caagaagttc    480
tcccgtagcg acccgaattt tagcatcccc caggcgaatc atagccatag cggcgattat    540
cactgcaccg ggaatattgg gtatacgttg tatagcagca agccggttac tatcaccgtg    600
cagggcggcc atcatcatca tcatcat                                       627
```

<210> SEQ ID NO 21
<211> LENGTH: 627
<212> TYPE: DNA
<213> ORGANISM: Artificial Sequence
<220> FEATURE:
<223> OTHER INFORMATION: DNA encoding MalE signal - FcgRIIb-m5b - 6His

<400> SEQUENCE: 21

```
atgaaaataa aaacaggtgc acgcatcctc gcattatccg cattaacgac gatgatgttt     60
tccgcctcgg ctctcgccat gggaactccc gcagcgcctc caaaggcggt tctgaaactg    120
gagccgcagt ggattaatgt gttgcaggaa gatagcgtga cgctgacctg ccgtggaacc    180
catagcccgg aatcagacag cgtacagtgg tttcacaacg gcaatttgat ccccactcaa    240
acgcagccga cgtaccgttt caaagccaac agtaacgatt cgggcgaata tacctgccag    300
acaggccaga ccagcctgtc ggatccagtg cacctgaccg tgctgtcaga atggctggtg    360
ctgcaaaccc cgcgtctgga atttcaggaa ggcgaaacca tagtgctgcg ttgccacagc    420
tggaaagata aaccgctggt gaaggtcacg ttcttccaga acgggaagag caagaagttc    480
```

| tcccgtagcg acccgaattt tagcatcccc caggcgaatc atagccatag cggcgattat | 540 |
| cactgcaccg ggaatattgg gtatacgttg tatagcagca agccggttac tatcaccgtg | 600 |
| cagggcggcc atcatcatca tcatcat | 627 |

```
<210> SEQ ID NO 22
<211> LENGTH: 627
<212> TYPE: DNA
<213> ORGANISM: Artificial Sequence
<220> FEATURE:
<223> OTHER INFORMATION: DNA encoding MalE signal - FcgRIIb-m5c - 6His

<400> SEQUENCE: 22
```

| atgaaaataa aaacaggtgc acgcatcctc gcattatccg cattaacgac gatgatgttt | 60 |
| tccgcctcgg ctctcgccat gggaactccc gcagcgcctc caaaggcggt tctgaaactg | 120 |
| gagccgcagt ggattaatgt gttgcaggaa gatagcgtga cgctgacctg ccgtggaacc | 180 |
| catagcccgg aatcagacag cgtacagtgg tttcacaacg gcaatttgat ccccactcat | 240 |
| acgcagccga cgtaccgttt caaagccacc agtaacgatt cgggcgaata tacctgccag | 300 |
| acaggccaga ccagcctgtc ggatccagtg cacctgaccg tgctgtcaga atggctggtg | 360 |
| ctgcaaaccc cgcgtctgga atttcaggaa ggcgaaacca tagtgctgcg ttgccacagc | 420 |
| tggaaagata aaccgctggt gaaggtcacg ttcttccaga cgggaagag caagaagttc | 480 |
| tcccgtagcg acccgaattt tagcatcccc caggcgaatc atagccatag cggcgattat | 540 |
| cactgcaccg ggaatattgg gtatacgttg tatagcagca agccggttac tatcaccgtg | 600 |
| cagggcggcc atcatcatca tcatcat | 627 |

```
<210> SEQ ID NO 23
<211> LENGTH: 627
<212> TYPE: DNA
<213> ORGANISM: Artificial Sequence
<220> FEATURE:
<223> OTHER INFORMATION: DNA encoding MalE signal - FcgRIIb-m6b - 6His

<400> SEQUENCE: 23
```

| atgaaaataa aaacaggtgc acgcatcctc gcattatccg cattaacgac gatgatgttt | 60 |
| tccgcctcgg ctctcgccat gggaactccc gcagcgcctc caaaggcggt tctgaaactg | 120 |
| gagccgcagt ggattaatgt gttgcaggaa gatagcgtga cgctgacctg ccgtggaacc | 180 |
| catagcccgg aatcagacag cgtacagtgg tttcacaacg gcaatttgat ccccactcaa | 240 |
| acgcagccga cgtaccgttt caaagccacc agtaacgatt cgggcgaata tacctgccag | 300 |
| acaggccaga ccagcctgtc ggatccagtg cacctgaccg tgctgtcaga atggctggtg | 360 |
| ctgcaaaccc cgcgtctgga atttcaggaa ggcgaaacca tagtgctgcg ttgccacagc | 420 |
| tggaaagata aaccgctggt gaaggtcacg ttcttccaga cgggaagag caagaagttc | 480 |
| tcccgtagcg acccgaattt tagcatcccc caggcgaatc atagccatag cggcgattat | 540 |
| cactgcaccg ggaatattgg gtatacgttg tatagcagca agccggttac tatcaccgtg | 600 |
| cagggcggcc atcatcatca tcatcat | 627 |

```
<210> SEQ ID NO 24
<211> LENGTH: 930
<212> TYPE: DNA
<213> ORGANISM: Artificial Sequence
<220> FEATURE:
<223> OTHER INFORMATION: DNA encoding FcgRIIb

<400> SEQUENCE: 24
```

```
atggggatat tgagctttct tccggtgtta gccaccgaaa gcgattgggc ggattgcaaa      60
agcccccagc cctggggcca tatgctgctg tggacagcgg tcctgtttct ggctccggtt     120
gcggggactc ccgcagcgcc tccaaaggcg gttctgaaac tggagccgca gtggattaat     180
gtgttgcagg aagatagcgt gacgctgacc tgccgtggaa cccatagccc ggaatcagac     240
agcatacagt ggtttcacaa cggcaatttg atccccactc atacgcagcc gtcgtaccgt     300
ttcaaagcca acaataacga ttcgggcgaa tatacctgcc agacaggcca gaccagcctg     360
agcgatccag tgcacctgac cgtgctgtca gaatggctgg tgctgcaaac cccgcatctg     420
gaatttcagg aaggcgaaac catagtgctg cgttgccaca gctggaaaga taaaccgctg     480
gtgaaggtca cgttcttcca gaacgggaag agcaagaagt tctcccgtag cgacccgaat     540
tttagcatcc cccaggcgaa tcatagccat agcggcgatt atcactgcac cgggaatatt     600
gggtatacgt tgtatagcag caagccggtt actatcaccg tgcaggcgcc gagctcatcg     660
ccgatgggca ttattgtggc ggtagttacc ggcatcgcgg tggccgccat tgtcgcggct     720
gtggtagccc tgatttactg ccgcaaaaaa cgtatcagtg ctttaccggg ttaccctgaa     780
tgccgtgaaa tgggcgagac cctgcccgaa aaaccggcga cccgaccaa tcccgatgaa      840 gcggataagg tgggcgcaga aaacaccatc acctatagcc tgctgatgca cccggatgcg     900
ctggaggaac cggatgatca aaatcgtatt                                      930
```

<210> SEQ ID NO 25
<211> LENGTH: 38
<212> TYPE: DNA
<213> ORGANISM: Artificial Sequence
<220> FEATURE:
<223> OTHER INFORMATION: Oligonucleotide

<400> SEQUENCE: 25

```
atggggatat tgagctttct tccggtgtta gccaccga                              38
```

<210> SEQ ID NO 26
<211> LENGTH: 40
<212> TYPE: DNA
<213> ORGANISM: Artificial Sequence
<220> FEATURE:
<223> OTHER INFORMATION: Oligonucleotide

<400> SEQUENCE: 26

```
ttttgcaatc cgcccaatcg ctttcggtgg ctaacaccgg                            40
```

<210> SEQ ID NO 27
<211> LENGTH: 40
<212> TYPE: DNA
<213> ORGANISM: Artificial Sequence
<220> FEATURE:
<223> OTHER INFORMATION: Oligonucleotide

<400> SEQUENCE: 27

```
gattgggcgg attgcaaaag cccccagccc tggggccata                            40
```

<210> SEQ ID NO 28
<211> LENGTH: 40
<212> TYPE: DNA
<213> ORGANISM: Artificial Sequence
<220> FEATURE:
<223> OTHER INFORMATION: Oligonucleotide

<400> SEQUENCE: 28
acaggaccgc tgtccacagc agcatatggc cccagggctg                                40

<210> SEQ ID NO 29
<211> LENGTH: 40
<212> TYPE: DNA
<213> ORGANISM: Artificial Sequence
<220> FEATURE:
<223> OTHER INFORMATION: Oligonucleotide

<400> SEQUENCE: 29
gtggacagcg gtcctgtttc tggctccggt tgcggggact                                40

<210> SEQ ID NO 30
<211> LENGTH: 40
<212> TYPE: DNA
<213> ORGANISM: Artificial Sequence
<220> FEATURE:
<223> OTHER INFORMATION: Oligonucleotide

<400> SEQUENCE: 30
gaaccgcctt tggaggcgct gcgggagtcc ccgcaaccgg                                40

<210> SEQ ID NO 31
<211> LENGTH: 40
<212> TYPE: DNA
<213> ORGANISM: Artificial Sequence
<220> FEATURE:
<223> OTHER INFORMATION: Oligonucleotide

<400> SEQUENCE: 31
gcctccaaag gcggttctga aactggagcc gcagtggatt                                40

<210> SEQ ID NO 32
<211> LENGTH: 40
<212> TYPE: DNA
<213> ORGANISM: Artificial Sequence
<220> FEATURE:
<223> OTHER INFORMATION: Oligonucleotide

<400> SEQUENCE: 32
acgctatctt cctgcaacac attaatccac tgcggctcca                                40

<210> SEQ ID NO 33
<211> LENGTH: 40
<212> TYPE: DNA
<213> ORGANISM: Artificial Sequence
<220> FEATURE:
<223> OTHER INFORMATION: Oligonucleotide

<400> SEQUENCE: 33
gtgttgcagg aagatagcgt gacgctgacc tgccgtggaa                                40

<210> SEQ ID NO 34
<211> LENGTH: 40
<212> TYPE: DNA
<213> ORGANISM: Artificial Sequence
<220> FEATURE:
<223> OTHER INFORMATION: Oligonucleotide

<400> SEQUENCE: 34
gctgtctgat tccgggctat gggttccacg gcaggtcagc                                40

<210> SEQ ID NO 35
<211> LENGTH: 40
<212> TYPE: DNA
<213> ORGANISM: Artificial Sequence

```
<220> FEATURE:
<223> OTHER INFORMATION: Oligonucleotide

<400> SEQUENCE: 35
gcccggaatc agacagcata cagtggtttc acaacggcaa                              40

<210> SEQ ID NO 36
<211> LENGTH: 40
<212> TYPE: DNA
<213> ORGANISM: Artificial Sequence
<220> FEATURE:
<223> OTHER INFORMATION: Oligonucleotide

<400> SEQUENCE: 36
tgcgtatgag tggggatcaa attgccgttg tgaaaccact                              40

<210> SEQ ID NO 37
<211> LENGTH: 40
<212> TYPE: DNA
<213> ORGANISM: Artificial Sequence
<220> FEATURE:
<223> OTHER INFORMATION: Oligonucleotide

<400> SEQUENCE: 37
tgatccccac tcatacgcag ccgtcgtacc gtttcaaagc                              40

<210> SEQ ID NO 38
<211> LENGTH: 40
<212> TYPE: DNA
<213> ORGANISM: Artificial Sequence
<220> FEATURE:
<223> OTHER INFORMATION: Oligonucleotide

<400> SEQUENCE: 38
tcgcccgaat cgttattgtt ggctttgaaa cggtacgacg                              40

<210> SEQ ID NO 39
<211> LENGTH: 40
<212> TYPE: DNA
<213> ORGANISM: Artificial Sequence
<220> FEATURE:
<223> OTHER INFORMATION: Oligonucleotide

<400> SEQUENCE: 39
aacaataacg attcgggcga atatacctgc cagacaggcc                              40

<210> SEQ ID NO 40
<211> LENGTH: 40
<212> TYPE: DNA
<213> ORGANISM: Artificial Sequence
<220> FEATURE:
<223> OTHER INFORMATION: Oligonucleotide

<400> SEQUENCE: 40
cactggatcg ctcaggctgg tctggcctgt ctggcaggta                              40

<210> SEQ ID NO 41
<211> LENGTH: 40
<212> TYPE: DNA
<213> ORGANISM: Artificial Sequence
<220> FEATURE:
<223> OTHER INFORMATION: Oligonucleotide

<400> SEQUENCE: 41
agcctgagcg atccagtgca cctgaccgtg ctgtcagaat                              40
```

<210> SEQ ID NO 42
<211> LENGTH: 40
<212> TYPE: DNA
<213> ORGANISM: Artificial Sequence
<220> FEATURE:
<223> OTHER INFORMATION: Oligonucleotide

<400> SEQUENCE: 42
gcggggtttg cagcaccagc cattctgaca gcacggtcag        40

<210> SEQ ID NO 43
<211> LENGTH: 40
<212> TYPE: DNA
<213> ORGANISM: Artificial Sequence
<220> FEATURE:
<223> OTHER INFORMATION: Oligonucleotide

<400> SEQUENCE: 43
gtgctgcaaa ccccgcatct ggaatttcag gaaggcgaaa        40

<210> SEQ ID NO 44
<211> LENGTH: 40
<212> TYPE: DNA
<213> ORGANISM: Artificial Sequence
<220> FEATURE:
<223> OTHER INFORMATION: Oligonucleotide

<400> SEQUENCE: 44
tggcaacgca gcactatggt ttcgccttcc tgaaattcca        40

<210> SEQ ID NO 45
<211> LENGTH: 40
<212> TYPE: DNA
<213> ORGANISM: Artificial Sequence
<220> FEATURE:
<223> OTHER INFORMATION: Oligonucleotide

<400> SEQUENCE: 45
catagtgctg cgttgccaca gctggaaaga taaaccgctg        40

<210> SEQ ID NO 46
<211> LENGTH: 40
<212> TYPE: DNA
<213> ORGANISM: Artificial Sequence
<220> FEATURE:
<223> OTHER INFORMATION: Oligonucleotide

<400> SEQUENCE: 46
tggaagaacg tgaccttcac cagcggttta tctttccagc        40

<210> SEQ ID NO 47
<211> LENGTH: 40
<212> TYPE: DNA
<213> ORGANISM: Artificial Sequence
<220> FEATURE:
<223> OTHER INFORMATION: Oligonucleotide

<400> SEQUENCE: 47
gtgaaggtca cgttcttcca gaacgggaag agcaagaagt        40

<210> SEQ ID NO 48
<211> LENGTH: 40
<212> TYPE: DNA
<213> ORGANISM: Artificial Sequence
<220> FEATURE:
<223> OTHER INFORMATION: Oligonucleotide

<400> SEQUENCE: 48
attcgggtcg ctacgggaga acttcttgct cttcccgttc         40

<210> SEQ ID NO 49
<211> LENGTH: 40
<212> TYPE: DNA
<213> ORGANISM: Artificial Sequence
<220> FEATURE:
<223> OTHER INFORMATION: Oligonucleotide

<400> SEQUENCE: 49
cccgtagcga cccgaattt agcatccccc aggcgaatca          40

<210> SEQ ID NO 50
<211> LENGTH: 40
<212> TYPE: DNA
<213> ORGANISM: Artificial Sequence
<220> FEATURE:
<223> OTHER INFORMATION: Oligonucleotide

<400> SEQUENCE: 50
agtgataatc gccgctatgg ctatgattcg cctgggggat         40

<210> SEQ ID NO 51
<211> LENGTH: 40
<212> TYPE: DNA
<213> ORGANISM: Artificial Sequence
<220> FEATURE:
<223> OTHER INFORMATION: Oligonucleotide

<400> SEQUENCE: 51
ccatagcggc gattatcact gcaccgggaa tattgggtat         40

<210> SEQ ID NO 52
<211> LENGTH: 40
<212> TYPE: DNA
<213> ORGANISM: Artificial Sequence
<220> FEATURE:
<223> OTHER INFORMATION: Oligonucleotide

<400> SEQUENCE: 52
ggcttgctgc tatacaacgt atacccaata ttcccggtgc         40

<210> SEQ ID NO 53
<211> LENGTH: 40
<212> TYPE: DNA
<213> ORGANISM: Artificial Sequence
<220> FEATURE:
<223> OTHER INFORMATION: Oligonucleotide

<400> SEQUENCE: 53
acgttgtata gcagcaagcc ggttactatc accgtgcagg         40

<210> SEQ ID NO 54
<211> LENGTH: 40
<212> TYPE: DNA
<213> ORGANISM: Artificial Sequence
<220> FEATURE:
<223> OTHER INFORMATION: Oligonucleotide

<400> SEQUENCE: 54
catcggcgat gagctcggcg cctgcacggt gatagtaacc         40

<210> SEQ ID NO 55

<210> SEQ ID NO 55
<211> LENGTH: 40
<212> TYPE: DNA
<213> ORGANISM: Artificial Sequence
<220> FEATURE:
<223> OTHER INFORMATION: Oligonucleotide

<400> SEQUENCE: 55
cgagctcatc gccgatgggc attattgtgg cggtagttac                        40

<210> SEQ ID NO 56
<211> LENGTH: 40
<212> TYPE: DNA
<213> ORGANISM: Artificial Sequence
<220> FEATURE:
<223> OTHER INFORMATION: Oligonucleotide

<400> SEQUENCE: 56
gcggccaccg cgatgccggt aactaccgcc acaataatgc                        40

<210> SEQ ID NO 57
<211> LENGTH: 40
<212> TYPE: DNA
<213> ORGANISM: Artificial Sequence
<220> FEATURE:
<223> OTHER INFORMATION: Oligonucleotide

<400> SEQUENCE: 57
atcgcggtgg ccgccattgt cgcggctgtg gtagccctga                        40

<210> SEQ ID NO 58
<211> LENGTH: 40
<212> TYPE: DNA
<213> ORGANISM: Artificial Sequence
<220> FEATURE:
<223> OTHER INFORMATION: Oligonucleotide

<400> SEQUENCE: 58
gatacgtttt ttgcggcagt aaatcagggc taccacagcc                        40

<210> SEQ ID NO 59
<211> LENGTH: 40
<212> TYPE: DNA
<213> ORGANISM: Artificial Sequence
<220> FEATURE:
<223> OTHER INFORMATION: Oligonucleotide

<400> SEQUENCE: 59
tactgccgca aaaacgtat cagtgcttta ccgggttacc                         40

<210> SEQ ID NO 60
<211> LENGTH: 40
<212> TYPE: DNA
<213> ORGANISM: Artificial Sequence
<220> FEATURE:
<223> OTHER INFORMATION: Oligonucleotide

<400> SEQUENCE: 60
cgcccatttc acggcattca gggtaacccg gtaaagcact                        40

<210> SEQ ID NO 61
<211> LENGTH: 40
<212> TYPE: DNA
<213> ORGANISM: Artificial Sequence
<220> FEATURE:
<223> OTHER INFORMATION: Oligonucleotide

<400> SEQUENCE: 61
atgccgtgaa atgggcgaga ccctgcccga aaaaccggcg    40

<210> SEQ ID NO 62
<211> LENGTH: 40
<212> TYPE: DNA
<213> ORGANISM: Artificial Sequence
<220> FEATURE:
<223> OTHER INFORMATION: Oligonucleotide

<400> SEQUENCE: 62
cgcttcatcg ggattggtcg ggttcgccgg ttttcgggc    40

<210> SEQ ID NO 63
<211> LENGTH: 40
<212> TYPE: DNA
<213> ORGANISM: Artificial Sequence
<220> FEATURE:
<223> OTHER INFORMATION: Oligonucleotide

<400> SEQUENCE: 63
gaccaatccc gatgaagcgg ataaggtggg cgcagaaaac    40

<210> SEQ ID NO 64
<211> LENGTH: 40
<212> TYPE: DNA
<213> ORGANISM: Artificial Sequence
<220> FEATURE:
<223> OTHER INFORMATION: Oligonucleotide

<400> SEQUENCE: 64
atcagcaggc tataggtgat ggtgttttct gcgcccacct    40

<210> SEQ ID NO 65
<211> LENGTH: 40
<212> TYPE: DNA
<213> ORGANISM: Artificial Sequence
<220> FEATURE:
<223> OTHER INFORMATION: Oligonucleotide

<400> SEQUENCE: 65
catcacctat agcctgctga tgcacccgga tgcgctggag    40

<210> SEQ ID NO 66
<211> LENGTH: 40
<212> TYPE: DNA
<213> ORGANISM: Artificial Sequence
<220> FEATURE:
<223> OTHER INFORMATION: Oligonucleotide

<400> SEQUENCE: 66
aatacgattt tgatcatccg gttcctccag cgcatccggg    40

<210> SEQ ID NO 67
<211> LENGTH: 37
<212> TYPE: DNA
<213> ORGANISM: Artificial Sequence
<220> FEATURE:
<223> OTHER INFORMATION: Oligonucleotide

<400> SEQUENCE: 67
ctagccatgg gaactcccgc agcgcctcca aaggcgg    37

<210> SEQ ID NO 68
<211> LENGTH: 72
<212> TYPE: DNA

```
<213> ORGANISM: Artificial Sequence
<220> FEATURE:
<223> OTHER INFORMATION: Oligonucleotide

<400> SEQUENCE: 68
cccaagctta atgatgatga tgatgatggc cgccctgcac ggtgatagta accggcttgc     60
tgctatacaa cg                                                        72

<210> SEQ ID NO 69
<211> LENGTH: 683
<212> TYPE: DNA
<213> ORGANISM: Artificial Sequence
<220> FEATURE:
<223> OTHER INFORMATION: pET-rhFcgRIIb sequence between XbaI and HindIII

<400> SEQUENCE: 69
tctagaaata attttgttta actttaagaa ggagatatac ataatacata tgaaaataaa     60
aacaggtgca cgcatcctcg cattatccgc attaacgacg atgatgtttt ccgcctcggc    120
tctcgccatg gaactcccg cagcgcctcc aaaggcggtt ctgaaactgg agccgcagtg    180
gattaatgtg ttgcaggaag atagcgtgac gctgacctgc cgtggaaccc atagcccgga    240
atcagacagc atacagtggt ttcacaacgg caatttgatc cccactcata cgcagccgtc    300
gtaccgtttc aaagccaaca ataacgattc gggcgaatat acctgccaga caggccagac    360
cagcctgagc gatccagtgc acctgaccgt gctgtcagaa tggctggtgc tgcaaaccccc   420 gcatctggaa tttcaggaag gcgaaaccat agtgctgcgt tgccacagct ggaaagataa    480
accgctggtg aaggtcacgt tcttccagaa cgggaagagc aagaagttct cccgtagcga    540
cccgaatttt agcatccccc aggcgaatca tagccatagc ggcgattatc actgcaccgg    600
gaatattggg tatacgttgt atagcagcaa gccggttact atcaccgtgc agggcggcca    660
tcatcatcat catcattaag ctt                                            683

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide

<400> SEQUENCE: 70
taatacgact cactataggg                                                20

<210> SEQ ID NO 71
<211> LENGTH: 19
<212> TYPE: DNA
<213> ORGANISM: Artificial Sequence
<220> FEATURE:
<223> OTHER INFORMATION: Oligonucleotide

<400> SEQUENCE: 71
tatgctagtt attgctcag                                                 19

<210> SEQ ID NO 72
<211> LENGTH: 28
<212> TYPE: DNA
<213> ORGANISM: Artificial Sequence
<220> FEATURE:
<223> OTHER INFORMATION: Oligonucleotide

<400> SEQUENCE: 72
ttgtgaaacc actgtacgct gtctgatt                                       28
```

<210> SEQ ID NO 73
<211> LENGTH: 28
<212> TYPE: DNA
<213> ORGANISM: Artificial Sequence
<220> FEATURE:
<223> OTHER INFORMATION: Oligonucleotide

<400> SEQUENCE: 73
aatcagacag cgtacagtgg tttcacaa                               28

<210> SEQ ID NO 74
<211> LENGTH: 25
<212> TYPE: DNA
<213> ORGANISM: Artificial Sequence
<220> FEATURE:
<223> OTHER INFORMATION: Oligonucleotide

<400> SEQUENCE: 74
tgaaattcca gacgcggggt ttgca                                  25

<210> SEQ ID NO 75
<211> LENGTH: 25
<212> TYPE: DNA
<213> ORGANISM: Artificial Sequence
<220> FEATURE:
<223> OTHER INFORMATION: Oligonucleotide

<400> SEQUENCE: 75
tgcaaacccc gcgtctggaa tttca                                  25

<210> SEQ ID NO 76
<211> LENGTH: 33
<212> TYPE: DNA
<213> ORGANISM: Artificial Sequence
<220> FEATURE:
<223> OTHER INFORMATION: Oligonucleotide

<400> SEQUENCE: 76
ggtcaggtgc actggatccg acaggctggt ctg                         33

<210> SEQ ID NO 77
<211> LENGTH: 33
<212> TYPE: DNA
<213> ORGANISM: Artificial Sequence
<220> FEATURE:
<223> OTHER INFORMATION: Oligonucleotide

<400> SEQUENCE: 77
cagaccagcc tgtcggatcc agtgcacctg acc                         33

<210> SEQ ID NO 78
<211> LENGTH: 32
<212> TYPE: DNA
<213> ORGANISM: Artificial Sequence
<220> FEATURE:
<223> OTHER INFORMATION: Oligonucleotide

<400> SEQUENCE: 78
tacgtcggct gcgtttgagt ggggatcaaa tt                          32

<210> SEQ ID NO 79
<211> LENGTH: 32
<212> TYPE: DNA
<213> ORGANISM: Artificial Sequence
<220> FEATURE:

<223> OTHER INFORMATION: Oligonucleotide

<400> SEQUENCE: 79
aatttgatcc ccactcaaac gcagccgacg ta                                    32

<210> SEQ ID NO 80
<211> LENGTH: 35
<212> TYPE: DNA
<213> ORGANISM: Artificial Sequence
<220> FEATURE:
<223> OTHER INFORMATION: Oligonucleotide

<400> SEQUENCE: 80
tcgcccgaat cgttactggt ggctttgaaa cggta                                 35

<210> SEQ ID NO 81
<211> LENGTH: 35
<212> TYPE: DNA
<213> ORGANISM: Artificial Sequence
<220> FEATURE:
<223> OTHER INFORMATION: Oligonucleotide

<400> SEQUENCE: 81
taccgtttca agccaccag taacgattcg ggcga                                  35

<210> SEQ ID NO 82
<211> LENGTH: 37
<212> TYPE: DNA
<213> ORGANISM: Artificial Sequence
<220> FEATURE:
<223> OTHER INFORMATION: Oligonucleotide

<400> SEQUENCE: 82
tagccatggg catgcgtacc gaagatctgc cgaaagc                               37

<210> SEQ ID NO 83
<211> LENGTH: 67
<212> TYPE: DNA
<213> ORGANISM: Artificial Sequence
<220> FEATURE:
<223> OTHER INFORMATION: Oligonucleotide

<400> SEQUENCE: 83
cccaagctta tccgcaggta tcgttgcggc agccctgcac ggtgatagta accggcttgc      60
tgctata                                                                67

<210> SEQ ID NO 84
<211> LENGTH: 19
<212> TYPE: DNA
<213> ORGANISM: Artificial Sequence
<220> FEATURE:
<223> OTHER INFORMATION: Oligonucleotide

<400> SEQUENCE: 84
tgtggtatgg ctgtgcagg                                                   19

<210> SEQ ID NO 85
<211> LENGTH: 18
<212> TYPE: DNA
<213> ORGANISM: Artificial Sequence
<220> FEATURE:
<223> OTHER INFORMATION: Oligonucleotide

<400> SEQUENCE: 85
tcggcatggg gtcaggtg                                                    18

<210> SEQ ID NO 86
<211> LENGTH: 205
<212> TYPE: PRT
<213> ORGANISM: Artificial Sequence
<220> FEATURE:
<223> OTHER INFORMATION: pTrc-m6b_Cys

<400> SEQUENCE: 86

```
Met Lys Tyr Leu Leu Ser Thr Ala Ala Ala Gly Leu Leu Leu Ala
1               5                   10                  15

Ala Gln Pro Ala Met Ala Met Gly Thr Pro Ala Ala Pro Pro Lys Ala
            20                  25                  30

Val Leu Lys Leu Glu Pro Gln Trp Ile Asn Val Leu Gln Glu Asp Ser
        35                  40                  45

Val Thr Leu Thr Cys Arg Gly Thr His Ser Pro Glu Ser Asp Ser Val
    50                  55                  60

Gln Trp Phe His Asn Gly Asn Leu Ile Pro Thr Gln Thr Gln Pro Thr
65                  70                  75                  80

Tyr Arg Phe Lys Ala Thr Ser Asn Asp Ser Gly Glu Tyr Thr Cys Gln
                85                  90                  95

Thr Gly Gln Thr Ser Leu Ser Asp Pro Val His Leu Thr Val Leu Ser
            100                 105                 110

Glu Trp Leu Val Leu Gln Thr Pro Arg Leu Glu Phe Gln Glu Gly Glu
        115                 120                 125

Thr Ile Val Leu Arg Cys His Ser Trp Lys Asp Lys Pro Leu Val Lys
    130                 135                 140

Val Thr Phe Phe Gln Asn Gly Lys Ser Lys Lys Phe Ser Arg Ser Asp
145                 150                 155                 160

Pro Asn Phe Ser Ile Pro Gln Ala Asn His Ser His Ser Gly Asp Tyr
                165                 170                 175

His Cys Thr Gly Asn Ile Gly Tyr Thr Leu Tyr Ser Ser Lys Pro Val
            180                 185                 190

Thr Ile Thr Val Gln Gly Cys Arg Asn Asp Thr Cys Gly
    195                 200                 205
```

<210> SEQ ID NO 87
<211> LENGTH: 615
<212> TYPE: DNA
<213> ORGANISM: Artificial Sequence
<220> FEATURE:
<223> OTHER INFORMATION: Oligonucleotide

<400> SEQUENCE: 87

```
atgaaatacc tgctgtcgac cgctgctgct ggtctgctgc tcctcgctgc ccagccggcg      60
atggccatgg gcactcccgc agcgcctcca aaggcggttc tgaaactgga gccgcagtgg     120
attaatgtgt tgcaggaaga tagcgtgacg ctgacctgcc gtggaaccca tagcccggaa     180
tcagacagcg tacagtggtt tcacaacggc aatttgatcc ccactcaaac gcagccgacg     240
taccgtttca agccaccagt aacgattcg ggcgaatata cctgccagac aggccagacc     300
agcctgtcgg atccagtgca cctgaccgtg ctgtcagaat ggctggtgct gcaaacccg      360 cgtctggaat tcaggaagg cgaaaccata gtgctgcgtt gccacagctg aaagataaa      420 ccgctggtga aggtcacgtt cttccagaac gggaagagca agaagttctc ccgtagcgac     480
ccgaatttta gcatccccca ggcgaatcat agccatagcg gcgattatca ctgcaccggg     540
aatattgggt atacgttgta tagcagcaag ccggttacta tcaccgtgca gggctgccgc     600
```
aacgatacct gcgga 615

<210> SEQ ID NO 88
<211> LENGTH: 209
<212> TYPE: PRT
<213> ORGANISM: Artificial Sequence
<220> FEATURE:
<223> OTHER INFORMATION: MalE signal - FcgRIIa - 6His

<400> SEQUENCE: 88

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Ile Gln Trp Phe His Asn Gly Asn Leu Ile Pro Thr His
65                  70                  75                  80

Thr Gln Pro Ser Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Leu Phe Ser
            180                 185                 190

Ser Lys Pro Val Thr Ile Thr Val Gln Gly Gly His His His His His
        195                 200                 205

His

<210> SEQ ID NO 89
<211> LENGTH: 209
<212> TYPE: PRT
<213> ORGANISM: Artificial Sequence
<220> FEATURE:
<223> OTHER INFORMATION: MalE signal - FcgRIIa-m6 - 6His

<400> SEQUENCE: 89

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Val Gln Trp Phe His Asn Gly Asn Leu Ile Pro Thr Gln
65                  70                  75                  80

```
Thr Gln Pro Thr Tyr Arg Phe Lys Ala Thr Ser Asn Asp Ser Gly Glu
            85                  90                  95

Tyr Thr Cys Gln Thr Gly Gln Thr Ser Leu Ser Asp Pro Val His Leu
        100                 105                 110

Thr Val Leu Ser Glu Trp Leu Val Leu Gln Thr Pro Arg Leu Glu Phe
            115                 120                 125

Gln Glu Gly Glu Thr Ile Met Leu Arg Cys His Ser Trp Lys Asp Lys
130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
            165                 170                 175

Ser Gly Asp Tyr His Cys Thr Gly Asn Ile Gly Tyr Thr Leu Phe Ser
            180                 185                 190

Ser Lys Pro Val Thr Ile Thr Val Gln Gly Gly His His His His His
            195                 200                 205
His

<210> SEQ ID NO 90
<211> LENGTH: 317
<212> TYPE: PRT
<213> ORGANISM: Homo sapiens
<300> PUBLICATION INFORMATION:
<308> DATABASE ACCESSION NUMBER: UniProt P12318-1
<309> DATABASE ENTRY DATE: 2007-11-13
<313> RELEVANT RESIDUES IN SEQ ID NO: (1)..(317)

<400> SEQUENCE: 90

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
            85                  90                  95

Asn Asp Ser Gly Glu Tyr Thr Cys Gln Thr Gly Gln Thr Ser Leu Ser
        100                 105                 110

Asp Pro Val His Leu Thr Val Leu Ser Glu Trp Leu Val Leu Gln Thr
    115                 120                 125

Pro His Leu Glu Phe Gln Glu Gly Glu Thr Ile Met Leu Arg Cys His
130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
            165                 170                 175

Ala Asn His Ser His Ser Gly Asp Tyr His Cys Thr Gly Asn Ile Gly
        180                 185                 190

Tyr Thr Leu Phe Ser Ser Lys Pro Val Thr Ile Thr Val Gln Val Pro
    195                 200                 205

Ser Met Gly Ser Ser Ser Pro Met Gly Ile Ile Val Ala Val Val Ile
210                 215                 220
```

Ala Thr Ala Val Ala Ala Ile Val Ala Val Val Ala Leu Ile Tyr
225                 230                 235                 240

Cys Arg Lys Lys Arg Ile Ser Ala Asn Ser Thr Asp Pro Val Lys Ala
            245                 250                 255

Ala Gln Phe Glu Pro Pro Gly Arg Gln Met Ile Ala Ile Arg Lys Arg
        260                 265                 270

Gln Leu Glu Glu Thr Asn Asn Asp Tyr Glu Thr Ala Asp Gly Gly Tyr
    275                 280                 285

Met Thr Leu Asn Pro Arg Ala Pro Thr Asp Asp Lys Asn Ile Tyr
290                 295                 300

Leu Thr Leu Pro Pro Asn Asp His Val Asn Ser Asn Asn
305                 310                 315

<210> SEQ ID NO 91
<211> LENGTH: 627
<212> TYPE: DNA
<213> ORGANISM: Artificial Sequence
<220> FEATURE:
<223> OTHER INFORMATION: DNA encoding MalE signal - FcgRIIa-m6 - 6His

<400> SEQUENCE: 91
atgaaaataa aaacaggtgc acgcatcctc gcattatccg cattaacgac gatgatgttt      60
tccgcctcgg ctctcgccat gggacaagcc gcagcgcctc caaaggcggt tctgaaactg     120
gagccgccgt ggattaatgt gttgcaggaa gatagcgtga cgctgacctg ccagggagcc     180
cgtagcccgg aatcagacag cgtacagtgg tttcacaacg gcaatttgat ccccactcaa     240
acgcagccga cgtaccgttt caaagccacc agtaacgatt cgggcgaata tacctgccag     300
acaggccaga ccagcctgtc ggatccagtg cacctgaccg tgctgtcaga atggctggtg     360
ctgcaaaccc cgcgtctgga atttcaggaa ggcgaaacca atgctgcg ttgccacagc       420 tggaaagata aaccgctggt gaaggtcacg ttcttccaga acgggaagag ccagaagttc     480
tcccatctcg acccgacttt tagcatcccc caggcgaatc atagccatag cggcgattat     540
cactgcaccg ggaatattgg gtatacgttg tttagcagca agccggttac tatcaccgtg     600
cagggcggcc atcatcatca tcatcat                                         627

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide

<400> SEQUENCE: 92
taatacgact cactataggg                                                 20

<210> SEQ ID NO 93
<211> LENGTH: 26
<212> TYPE: DNA
<213> ORGANISM: Artificial Sequence
<220> FEATURE:
<223> OTHER INFORMATION: Oligonucleotide

<400> SEQUENCE: 93
acattaatcc acggcggctc cagttt                                          26

<210> SEQ ID NO 94
<211> LENGTH: 26
<212> TYPE: DNA

```
<213> ORGANISM: Artificial Sequence
<220> FEATURE:
<223> OTHER INFORMATION: Oligonucleotide

<400> SEQUENCE: 94
aaactggagc cgccgtggat taatgt                                              26

<210> SEQ ID NO 95
<211> LENGTH: 37
<212> TYPE: DNA
<213> ORGANISM: Artificial Sequence
<220> FEATURE:
<223> OTHER INFORMATION: Oligonucleotide

<400> SEQUENCE: 95
taaaagtcgg gtcgagatgg gagaacttct ggctctt                                  37

<210> SEQ ID NO 96
<211> LENGTH: 37
<212> TYPE: DNA
<213> ORGANISM: Artificial Sequence
<220> FEATURE:
<223> OTHER INFORMATION: Oligonucleotide

<400> SEQUENCE: 96
aagagccaga agttctccca tctcgacccg actttta                                  37

<210> SEQ ID NO 97
<211> LENGTH: 19
<212> TYPE: DNA
<213> ORGANISM: Artificial Sequence
<220> FEATURE:
<223> OTHER INFORMATION: Oligonucleotide

<400> SEQUENCE: 97
tatgctagtt attgctcag                                                      19

<210> SEQ ID NO 98
<211> LENGTH: 29
<212> TYPE: DNA
<213> ORGANISM: Artificial Sequence
<220> FEATURE:
<223> OTHER INFORMATION: Oligonucleotide

<400> SEQUENCE: 98
ttccgggcta cgggctccct ggcaggtca                                           29

<210> SEQ ID NO 99
<211> LENGTH: 29
<212> TYPE: DNA
<213> ORGANISM: Artificial Sequence
<220> FEATURE:
<223> OTHER INFORMATION: Oligonucleotide

<400> SEQUENCE: 99
tgacctgcca gggagcccgt agcccggaa                                           29

<210> SEQ ID NO 100
<211> LENGTH: 31
<212> TYPE: DNA
<213> ORGANISM: Artificial Sequence
<220> FEATURE:
<223> OTHER INFORMATION: Oligonucleotide

<400> SEQUENCE: 100
aaccggcttg ctgctaaaca acgtataccc a                                        31
```

<210> SEQ ID NO 101
<211> LENGTH: 31
<212> TYPE: DNA
<213> ORGANISM: Artificial Sequence
<220> FEATURE:
<223> OTHER INFORMATION: Oligonucleotide

<400> SEQUENCE: 101
tgggtatacg ttgtttagca gcaagccggt t                              31

<210> SEQ ID NO 102
<211> LENGTH: 31
<212> TYPE: DNA
<213> ORGANISM: Artificial Sequence
<220> FEATURE:
<223> OTHER INFORMATION: Oligonucleotide

<400> SEQUENCE: 102
tcgccatggg acaagccgca gcgcctccaa a                              31

<210> SEQ ID NO 103
<211> LENGTH: 27
<212> TYPE: DNA
<213> ORGANISM: Artificial Sequence
<220> FEATURE:
<223> OTHER INFORMATION: Oligonucleotide

<400> SEQUENCE: 103
tggcaacgca gcattatggt ttcgcct                                   27

<210> SEQ ID NO 104
<211> LENGTH: 27
<212> TYPE: DNA
<213> ORGANISM: Artificial Sequence
<220> FEATURE:
<223> OTHER INFORMATION: Oligonucleotide

<400> SEQUENCE: 104
aggcgaaacc ataatgctgc gttgcca                                   27

<210> SEQ ID NO 105
<211> LENGTH: 627
<212> TYPE: DNA
<213> ORGANISM: Artificial Sequence
<220> FEATURE:
<223> OTHER INFORMATION: DNA encoding MalE signal - FcgRIIa - 6His

<400> SEQUENCE: 105
atgaaaataa aaacaggtgc acgcatcctc gcattatccg cattaacgac gatgatgttt    60
tccgcctcgg ctctcgccat gggacaagcc gcagcgcctc caaaggcggt tctgaaactg   120
gagccgccgt ggattaatgt gttgcaggaa gatagcgtga cgctgacctg ccagggagcc   180
cgtagcccgg aatcagacag catacagtgg tttcacaacg gcaatttgat ccccactcat   240
acgcagccgt cgtaccgttt caaagccaac aataacgatt cgggcgaata cacctgccag   300
acaggccaga ccagcctgag cgatccagtg cacctgaccg tgctgtcaga atggctggtg   360
ctgcaaaccc cgcatctgga atttcaggaa ggcgaaacca taatgctgcg ttgccacagc   420
tggaaagata aaccgctggt gaaggtcacg ttcttccaga acgggaagag ccagaagttc   480
tcccatctcg acccgacttt tagcatcccc caggcgaatc atagccatag cggcgattat   540
cactgcaccg ggaatattgg gtatacgttg tttagcagca agccggttac tatcaccgtg   600 caggcggcc atcatcatca tcatcat                                          627

<210> SEQ ID NO 106
<211> LENGTH: 209
<212> TYPE: PRT
<213> ORGANISM: Artificial Sequence
<220> FEATURE:
<223> OTHER INFORMATION: MalE signal - FcgRIIb - 6His

<400> SEQUENCE: 106

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Ile Gln Trp Phe His Asn Gly Asn Leu Ile Pro Thr His
65                  70                  75                  80

Thr Gln Pro Ser Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His

<210> SEQ ID NO 107
<211> LENGTH: 310
<212> TYPE: PRT
<213> ORGANISM: Homo sapiens
<300> PUBLICATION INFORMATION:
<308> DATABASE ACCESSION NUMBER: UniProt P31994
<309> DATABASE ENTRY DATE: 2000-05-30
<313> RELEVANT RESIDUES IN SEQ ID NO: (1)..(310)

<400> SEQUENCE: 107

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Leu Pro
                245                 250                 255

Gly Tyr Pro Glu Cys Arg Glu Met Gly Glu Thr Leu Pro Glu Lys Pro
            260                 265                 270

Ala Asn Pro Thr Asn Pro Asp Glu Ala Asp Lys Val Gly Ala Glu Asn
        275                 280                 285

Thr Ile Thr Tyr Ser Leu Leu Met His Pro Asp Ala Leu Glu Glu Pro
    290                 295                 300

Asp Asp Gln Asn Arg Ile
305                 310

<210> SEQ ID NO 108
<211> LENGTH: 930
<212> TYPE: DNA
<213> ORGANISM: Artificial Sequence
<220> FEATURE:
<223> OTHER INFORMATION: DNA encoding FcgRIIb

<400> SEQUENCE: 108
atggggatat tgagctttct tccggtgtta gccaccgaaa gcgattgggc ggattgcaaa      60
agcccccagc cctggggcca tatgctgctg tggacagcgg tcctgtttct ggctccggtt     120
gcggggactc ccgcagcgcc tccaaaggcg gttctgaaac tggagccgca gtggattaat     180
gtgttgcagg aagatagcgt gacgctgacc tgccgtggaa cccatagccc ggaatcagac     240
agcatacagt ggtttcacaa cggcaatttg atccccactc atacgcagcc gtcgtaccgt     300
ttcaaagcca acaataacga ttcgggcgaa tatacctgcc agacaggcca gaccagcctg     360
agcgatccag tgcacctgac cgtgctgtca gaatggctgg tgctgcaaac cccgcatctg     420
gaatttcagg aaggcgaaac catagtgctg cgttgccaca gctggaaaga taaaccgctg     480
gtgaaggtca cgttcttcca gaacgggaag agcaagaagt tctcccgtag cgacccgaat     540
tttagcatcc cccaggcgaa tcatagccat agcggcgatt atcactgcac cgggaatatt     600
gggtatacgt tgtatagcag caagccggtt actatcaccg tgcaggcgcc gagctcatcg     660
ccgatgggca ttattgtggc ggtagttacc ggcatcgcgg tggccgccat tgtcgcggct     720

```
gtggtagccc tgatttactg ccgcaaaaaa cgtatcagtg ctttaccggg ttaccctgaa      780
tgccgtgaaa tgggcgagac cctgcccgaa aaaccggcga acccgaccaa tcccgatgaa      840
gcggataagg tgggcgcaga aaacaccatc acctatagcc tgctgatgca cccggatgcg      900
ctggaggaac cggatgatca aaatcgtatt                                       930
```

<210> SEQ ID NO 109
<211> LENGTH: 38
<212> TYPE: DNA
<213> ORGANISM: Artificial Sequence
<220> FEATURE:
<223> OTHER INFORMATION: Oligonucleotide

<400> SEQUENCE: 109

```
atggggatat tgagctttct tccggtgtta gccaccga                              38
```

<210> SEQ ID NO 110
<211> LENGTH: 40
<212> TYPE: DNA
<213> ORGANISM: Artificial Sequence
<220> FEATURE:
<223> OTHER INFORMATION: Oligonucleotide

<400> SEQUENCE: 110

```
ttttgcaatc cgcccaatcg ctttcggtgg ctaacaccgg                            40
```

<210> SEQ ID NO 111
<211> LENGTH: 40
<212> TYPE: DNA
<213> ORGANISM: Artificial Sequence
<220> FEATURE:
<223> OTHER INFORMATION: Oligonucleotide

<400> SEQUENCE: 111

```
gattgggcgg attgcaaaag cccccagccc tggggccata                            40
```

<210> SEQ ID NO 112
<211> LENGTH: 40
<212> TYPE: DNA
<213> ORGANISM: Artificial Sequence
<220> FEATURE:
<223> OTHER INFORMATION: Oligonucleotide

<400> SEQUENCE: 112

```
acaggaccgc tgtccacagc agcatatggc cccagggctg                            40
```

<210> SEQ ID NO 113
<211> LENGTH: 40
<212> TYPE: DNA
<213> ORGANISM: Artificial Sequence
<220> FEATURE:
<223> OTHER INFORMATION: Oligonucleotide

<400> SEQUENCE: 113

```
gtggacagcg gtcctgtttc tggctccggt tgcggggact                            40
```

<210> SEQ ID NO 114
<211> LENGTH: 40
<212> TYPE: DNA
<213> ORGANISM: Artificial Sequence
<220> FEATURE:
<223> OTHER INFORMATION: Oligonucleotide

<400> SEQUENCE: 114

```
gaaccgcctt tggaggcgct gcgggagtcc ccgcaaccgg                                40

<210> SEQ ID NO 115
<211> LENGTH: 40
<212> TYPE: DNA
<213> ORGANISM: Artificial Sequence
<220> FEATURE:
<223> OTHER INFORMATION: Oligonucleotide

<400> SEQUENCE: 115
gcctccaaag gcggttctga aactggagcc gcagtggatt                                40

<210> SEQ ID NO 116
<211> LENGTH: 40
<212> TYPE: DNA
<213> ORGANISM: Artificial Sequence
<220> FEATURE:
<223> OTHER INFORMATION: Oligonucleotide

<400> SEQUENCE: 116
acgctatctt cctgcaacac attaatccac tgcggctcca                                40

<210> SEQ ID NO 117
<211> LENGTH: 40
<212> TYPE: DNA
<213> ORGANISM: Artificial Sequence
<220> FEATURE:
<223> OTHER INFORMATION: Oligonucleotide

<400> SEQUENCE: 117
gtgttgcagg aagatagcgt gacgctgacc tgccgtggaa                                40

<210> SEQ ID NO 118
<211> LENGTH: 40
<212> TYPE: DNA
<213> ORGANISM: Artificial Sequence
<220> FEATURE:
<223> OTHER INFORMATION: Oligonucleotide

<400> SEQUENCE: 118
gctgtctgat tccgggctat gggttccacg gcaggtcagc                                40

<210> SEQ ID NO 119
<211> LENGTH: 40
<212> TYPE: DNA
<213> ORGANISM: Artificial Sequence
<220> FEATURE:
<223> OTHER INFORMATION: Oligonucleotide

<400> SEQUENCE: 119
gcccggaatc agacagcata cagtggtttc acaacggcaa                                40

<210> SEQ ID NO 120
<211> LENGTH: 40
<212> TYPE: DNA
<213> ORGANISM: Artificial Sequence
<220> FEATURE:
<223> OTHER INFORMATION: Oligonucleotide

<400> SEQUENCE: 120
tgcgtatgag tggggatcaa attgccgttg tgaaaccact                                40

<210> SEQ ID NO 121
<211> LENGTH: 40
<212> TYPE: DNA
<213> ORGANISM: Artificial Sequence
```

```
<220> FEATURE:
<223> OTHER INFORMATION: Oligonucleotide

<400> SEQUENCE: 121
tgatccccac tcatacgcag ccgtcgtacc gtttcaaagc                              40

<210> SEQ ID NO 122
<211> LENGTH: 40
<212> TYPE: DNA
<213> ORGANISM: Artificial Sequence
<220> FEATURE:
<223> OTHER INFORMATION: Oligonucleotide

<400> SEQUENCE: 122
tcgcccgaat cgttattgtt ggctttgaaa cggtacgacg                              40

<210> SEQ ID NO 123
<211> LENGTH: 40
<212> TYPE: DNA
<213> ORGANISM: Artificial Sequence
<220> FEATURE:
<223> OTHER INFORMATION: Oligonucleotide

<400> SEQUENCE: 123
aacaataacg attcgggcga atatacctgc cagacaggcc                              40

<210> SEQ ID NO 124
<211> LENGTH: 40
<212> TYPE: DNA
<213> ORGANISM: Artificial Sequence
<220> FEATURE:
<223> OTHER INFORMATION: Oligonucleotide

<400> SEQUENCE: 124
cactggatcg ctcaggctgg tctggcctgt ctggcaggta                              40

<210> SEQ ID NO 125
<211> LENGTH: 40
<212> TYPE: DNA
<213> ORGANISM: Artificial Sequence
<220> FEATURE:
<223> OTHER INFORMATION: Oligonucleotide

<400> SEQUENCE: 125
agcctgagcg atccagtgca cctgaccgtg ctgtcagaat                              40

<210> SEQ ID NO 126
<211> LENGTH: 40
<212> TYPE: DNA
<213> ORGANISM: Artificial Sequence
<220> FEATURE:
<223> OTHER INFORMATION: Oligonucleotide

<400> SEQUENCE: 126
gcggggtttg cagcaccagc cattctgaca gcacggtcag                              40

<210> SEQ ID NO 127
<211> LENGTH: 40
<212> TYPE: DNA
<213> ORGANISM: Artificial Sequence
<220> FEATURE:
<223> OTHER INFORMATION: Oligonucleotide

<400> SEQUENCE: 127
gtgctgcaaa ccccgcatct ggaatttcag gaaggcgaaa                              40
```

<210> SEQ ID NO 128
<211> LENGTH: 40
<212> TYPE: DNA
<213> ORGANISM: Artificial Sequence
<220> FEATURE:
<223> OTHER INFORMATION: Oligonucleotide

<400> SEQUENCE: 128
tggcaacgca gcactatggt ttcgccttcc tgaaattcca         40

<210> SEQ ID NO 129
<211> LENGTH: 40
<212> TYPE: DNA
<213> ORGANISM: Artificial Sequence
<220> FEATURE:
<223> OTHER INFORMATION: Oligonucleotide

<400> SEQUENCE: 129
catagtgctg cgttgccaca gctggaaaga taaaccgctg         40

<210> SEQ ID NO 130
<211> LENGTH: 40
<212> TYPE: DNA
<213> ORGANISM: Artificial Sequence
<220> FEATURE:
<223> OTHER INFORMATION: Oligonucleotide

<400> SEQUENCE: 130
tggaagaacg tgaccttcac cagcggttta tctttccagc         40

<210> SEQ ID NO 131
<211> LENGTH: 40
<212> TYPE: DNA
<213> ORGANISM: Artificial Sequence
<220> FEATURE:
<223> OTHER INFORMATION: Oligonucleotide

<400> SEQUENCE: 131
gtgaaggtca cgttcttcca gaacgggaag agcaagaagt         40

<210> SEQ ID NO 132
<211> LENGTH: 40
<212> TYPE: DNA
<213> ORGANISM: Artificial Sequence
<220> FEATURE:
<223> OTHER INFORMATION: Oligonucleotide

<400> SEQUENCE: 132
attcgggtcg ctacgggaga acttcttgct cttcccgttc         40

<210> SEQ ID NO 133
<211> LENGTH: 40
<212> TYPE: DNA
<213> ORGANISM: Artificial Sequence
<220> FEATURE:
<223> OTHER INFORMATION: Oligonucleotide

<400> SEQUENCE: 133
cccgtagcga cccgaatttt agcatccccc aggcgaatca         40

<210> SEQ ID NO 134
<211> LENGTH: 40
<212> TYPE: DNA
<213> ORGANISM: Artificial Sequence
<220> FEATURE:
<223> OTHER INFORMATION: Oligonucleotide

<400> SEQUENCE: 134
agtgataatc gccgctatgg ctatgattcg cctgggggat					40

<210> SEQ ID NO 135
<211> LENGTH: 40
<212> TYPE: DNA
<213> ORGANISM: Artificial Sequence
<220> FEATURE:
<223> OTHER INFORMATION: Oligonucleotide

<400> SEQUENCE: 135
ccatagcggc gattatcact gcaccgggaa tattgggtat					40

<210> SEQ ID NO 136
<211> LENGTH: 40
<212> TYPE: DNA
<213> ORGANISM: Artificial Sequence
<220> FEATURE:
<223> OTHER INFORMATION: Oligonucleotide

<400> SEQUENCE: 136
ggcttgctgc tatacaacgt atacccaata ttcccggtgc					40

<210> SEQ ID NO 137
<211> LENGTH: 40
<212> TYPE: DNA
<213> ORGANISM: Artificial Sequence
<220> FEATURE:
<223> OTHER INFORMATION: Oligonucleotide

<400> SEQUENCE: 137
acgttgtata gcagcaagcc ggttactatc accgtgcagg					40

<210> SEQ ID NO 138
<211> LENGTH: 40
<212> TYPE: DNA
<213> ORGANISM: Artificial Sequence
<220> FEATURE:
<223> OTHER INFORMATION: Oligonucleotide

<400> SEQUENCE: 138
catcggcgat gagctcggcg cctgcacggt gatagtaacc					40

<210> SEQ ID NO 139
<211> LENGTH: 40
<212> TYPE: DNA
<213> ORGANISM: Artificial Sequence
<220> FEATURE:
<223> OTHER INFORMATION: Oligonucleotide

<400> SEQUENCE: 139
cgagctcatc gccgatgggc attattgtgg cggtagttac					40

<210> SEQ ID NO 140
<211> LENGTH: 40
<212> TYPE: DNA
<213> ORGANISM: Artificial Sequence
<220> FEATURE:
<223> OTHER INFORMATION: Oligonucleotide

<400> SEQUENCE: 140
gcggccaccg cgatgccggt aactaccgcc acaataatgc					40

<210> SEQ ID NO 141

<210> SEQ ID NO 141
<211> LENGTH: 40
<212> TYPE: DNA
<213> ORGANISM: Artificial Sequence
<220> FEATURE:
<223> OTHER INFORMATION: Oligonucleotide

<400> SEQUENCE: 141
atcgcggtgg ccgccattgt cgcggctgtg gtagccctga                                40

<210> SEQ ID NO 142
<211> LENGTH: 40
<212> TYPE: DNA
<213> ORGANISM: Artificial Sequence
<220> FEATURE:
<223> OTHER INFORMATION: Oligonucleotide

<400> SEQUENCE: 142
gatacgtttt ttgcggcagt aaatcagggc taccacagcc                                40

<210> SEQ ID NO 143
<211> LENGTH: 40
<212> TYPE: DNA
<213> ORGANISM: Artificial Sequence
<220> FEATURE:
<223> OTHER INFORMATION: Oligonucleotide

<400> SEQUENCE: 143
tactgccgca aaaaacgtat cagtgcttta ccgggttacc                                40

<210> SEQ ID NO 144
<211> LENGTH: 40
<212> TYPE: DNA
<213> ORGANISM: Artificial Sequence
<220> FEATURE:
<223> OTHER INFORMATION: Oligonucleotide

<400> SEQUENCE: 144
cgcccatttc acggcattca gggtaacccg gtaaagcact                                40

<210> SEQ ID NO 145
<211> LENGTH: 40
<212> TYPE: DNA
<213> ORGANISM: Artificial Sequence
<220> FEATURE:
<223> OTHER INFORMATION: Oligonucleotide

<400> SEQUENCE: 145
atgccgtgaa atgggcgaga ccctgcccga aaaccggcg                                 40

<210> SEQ ID NO 146
<211> LENGTH: 40
<212> TYPE: DNA
<213> ORGANISM: Artificial Sequence
<220> FEATURE:
<223> OTHER INFORMATION: Oligonucleotide

<400> SEQUENCE: 146
cgcttcatcg ggattggtcg ggttcgccgg ttttcgggc                                 40

<210> SEQ ID NO 147
<211> LENGTH: 40
<212> TYPE: DNA
<213> ORGANISM: Artificial Sequence
<220> FEATURE:
<223> OTHER INFORMATION: Oligonucleotide

<400> SEQUENCE: 147
gaccaatccc gatgaagcgg ataaggtggg cgcagaaaac        40

<210> SEQ ID NO 148
<211> LENGTH: 40
<212> TYPE: DNA
<213> ORGANISM: Artificial Sequence
<220> FEATURE:
<223> OTHER INFORMATION: Oligonucleotide

<400> SEQUENCE: 148
atcagcaggc tataggtgat ggtgttttct gcgcccacct        40

<210> SEQ ID NO 149
<211> LENGTH: 40
<212> TYPE: DNA
<213> ORGANISM: Artificial Sequence
<220> FEATURE:
<223> OTHER INFORMATION: Oligonucleotide

<400> SEQUENCE: 149
catcacctat agcctgctga tgcacccgga tgcgctggag        40

<210> SEQ ID NO 150
<211> LENGTH: 40
<212> TYPE: DNA
<213> ORGANISM: Artificial Sequence
<220> FEATURE:
<223> OTHER INFORMATION: Oligonucleotide

<400> SEQUENCE: 150
aatacgattt tgatcatccg gttcctccag cgcatccggg        40

<210> SEQ ID NO 151
<211> LENGTH: 37
<212> TYPE: DNA
<213> ORGANISM: Artificial Sequence
<220> FEATURE:
<223> OTHER INFORMATION: Oligonucleotide

<400> SEQUENCE: 151
ctagccatgg gaactcccgc agcgcctcca aaggcgg        37

<210> SEQ ID NO 152
<211> LENGTH: 72
<212> TYPE: DNA
<213> ORGANISM: Artificial Sequence
<220> FEATURE:
<223> OTHER INFORMATION: Oligonucleotide

<400> SEQUENCE: 152
cccaagctta atgatgatga tgatgatggc cgccctgcac ggtgatagta accggcttgc        60
tgctatacaa cg        72

<210> SEQ ID NO 153
<211> LENGTH: 683
<212> TYPE: DNA
<213> ORGANISM: Artificial Sequence
<220> FEATURE:
<223> OTHER INFORMATION: pET - rhFcgRIIb sequence between XbaI and
      HindIII

<400> SEQUENCE: 153
tctagaaata attttgttta actttaagaa ggagatatac ataatacata tgaaaataaa        60
aacaggtgca cgcatcctcg cattatccgc attaacgacg atgatgtttt ccgcctcggc       120

```
tctcgccatg ggaactcccg cagcgcctcc aaaggcggtt ctgaaactgg agccgcagtg      180
gattaatgtg ttgcaggaag atagcgtgac gctgacctgc cgtggaaccc atagcccgga      240
atcagacagc atacagtggt ttcacaacgg caatttgatc cccactcata cgcagccgtc      300
gtaccgtttc aaagccaaca ataacgattc gggcgaatat acctgccaga caggccagac      360
cagcctgagc gatccagtgc acctgaccgt gctgtcagaa tggctggtgc tgcaaacccc      420
gcatctggaa tttcaggaag cgaaaccat agtgctgcgt tgccacagct ggaaagataa      480
accgctggtg aaggtcacgt tcttccagaa cgggaagagc aagaagttct cccgtagcga      540
cccgaatttt agcatccccc aggcgaatca tagccatagc ggcgattatc actgcaccgg      600
gaatattggg tatacgttgt atagcagcaa gccggttact atcaccgtgc agggcggcca      660
tcatcatcat catcattaag ctt                                               683
```

<210> SEQ ID NO 154
<211> LENGTH: 209
<212> TYPE: PRT
<213> ORGANISM: Artificial Sequence
<220> FEATURE:
<223> OTHER INFORMATION: MalE signal - FcgRIIb-a4F3 - 6His

<400> SEQUENCE: 154

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
            20                  25                  30

Pro Pro Lys Ala Val Leu Lys Leu Glu Pro Gln Trp Ile Asn Val Leu
        35                  40                  45

Gln Glu Asp Ser Val Thr Leu Thr Cys Arg Gly Thr His Ser Pro Glu
    50                  55                  60

Ser Asp Ser Ile Gln Trp Phe His Asn Gly Asn Leu Ile Pro Thr His
65                  70                  75                  80

Thr Gln Pro Thr Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Val Leu Arg Cys His Ser Trp Lys Asp Lys
    130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His
```

<210> SEQ ID NO 155
<211> LENGTH: 627
<212> TYPE: DNA
<213> ORGANISM: Artificial Sequence
<220> FEATURE:
<223> OTHER INFORMATION: DNA encoding MalE signal - FcgRIIb-a4F3 - 6His

<400> SEQUENCE: 155

```
atgaaaataa aaacaggtgc acgcatcctc gcattatccg cattaacgac gatgatgttt      60
tccgcctcgg ctctcgccat gggaactccc gcagcgcctc caaaggcggt tctgaaactg     120
gagccgcagt ggattaatgt gttgcaggaa gatagcgtga cgctgacctg ccgtggaacc     180
catagcccgg aatcagacag catacagtgg tttcacaacg gcaatttgat ccccactcat     240
acgcagccga cgtaccgttt caaagccaac aataacgatt cgggcgaata tacctgccag     300
acaggccaga ccagcctgag cgatccagtg cacctgaccg tgctgtcaga atggctggtg     360
ctgcaaaccc cgcatctgga atttcaggaa ggcgaaacca tagtgctgcg ttgccacagc     420
tggaaagata aaccgctggt gaaggtcacg ttcttccaga acgggaagag caagaagttc     480
tcccgtagcg acccgaattt tagcatcccc caggcgaatc atagccatag cggcgattat     540
cactgcaccg ggaatattgg gtatacgttg tatagcagca agccggttac tatcaccgtg     600
cagggcggcc atcatcatca tcatcat                                         627
```

<210> SEQ ID NO 156
<211> LENGTH: 209
<212> TYPE: PRT
<213> ORGANISM: Artificial Sequence
<220> FEATURE:
<223> OTHER INFORMATION: MalE signal - FcgRIIb-m3 - 6His

<400> SEQUENCE: 156

```
Met Lys Ile Lys Thr Gly Ala Arg Ile Leu Ala Leu Ser Ala Leu Thr
1               5                   10                  15
Thr Met Met Phe Ser Ala Ser Ala Leu Ala Met Gly Thr Pro Ala Ala
                20                  25                  30
Pro Pro Lys Ala Val Leu Lys Leu Glu Pro Gln Trp Ile Asn Val Leu
            35                  40                  45
Gln Glu Asp Ser Val Thr Leu Thr Cys Arg Gly Thr His Ser Pro Glu
        50                  55                  60
Ser Asp Ser Val Gln Trp Phe His Asn Gly Asn Leu Ile Pro Thr His
65                  70                  75                  80
Thr Gln Pro Thr Tyr Arg Phe Lys Ala Asn Asn Asn Asp Ser Gly Glu
                85                  90                  95
Tyr Thr Cys Gln Thr Gly Gln Thr Ser Leu Ser Asp Pro Val His Leu
            100                 105                 110
Thr Val Leu Ser Glu Trp Leu Val Leu Gln Thr Pro Arg Leu Glu Phe
        115                 120                 125
Gln Glu Gly Glu Thr Ile Val Leu Arg Cys His Ser Trp Lys Asp Lys
    130                 135                 140
Pro Leu Val Lys Val Thr Phe Phe Gln Asn Gly Lys Ser Lys Lys Phe
145                 150                 155                 160
Ser Arg Ser Asp Pro Asn Phe Ser Ile Pro Gln Ala Asn His Ser His
                165                 170                 175
Ser Gly Asp Tyr His Cys Thr Gly Asn Ile Gly Tyr Thr Leu Tyr Ser
            180                 185                 190
Ser Lys Pro Val Thr Ile Thr Val Gln Gly Gly His His His His His
        195                 200                 205
His
```

<210> SEQ ID NO 157
<211> LENGTH: 28

```
<212> TYPE: DNA
<213> ORGANISM: Artificial Sequence
<220> FEATURE:
<223> OTHER INFORMATION: Oligonucleotide

<400> SEQUENCE: 157
ttgtgaaacc actgtacgct gtctgatt                                        28

<210> SEQ ID NO 158
<211> LENGTH: 28
<212> TYPE: DNA
<213> ORGANISM: Artificial Sequence
<220> FEATURE:
<223> OTHER INFORMATION: Oligonucleotide

<400> SEQUENCE: 158
aatcagacag cgtacagtgg tttcacaa                                        28

<210> SEQ ID NO 159
<211> LENGTH: 25
<212> TYPE: DNA
<213> ORGANISM: Artificial Sequence
<220> FEATURE:
<223> OTHER INFORMATION: Oligonucleotide

<400> SEQUENCE: 159
tgaaattcca gacgcggggt ttgca                                           25

<210> SEQ ID NO 160
<211> LENGTH: 25
<212> TYPE: DNA
<213> ORGANISM: Artificial Sequence
<220> FEATURE:
<223> OTHER INFORMATION: Oligonucleotide

<400> SEQUENCE: 160
tgcaaacccc gcgtctggaa tttca                                           25

<210> SEQ ID NO 161
<211> LENGTH: 627
<212> TYPE: DNA
<213> ORGANISM: Artificial Sequence
<220> FEATURE:
<223> OTHER INFORMATION: DNA encoding MalE signal - FcgRIIb-m3 - 6His

<400> SEQUENCE: 161
atgaaaataa aaacaggtgc acgcatcctc gcattatccg cattaacgac gatgatgttt     60
tccgcctcgg ctctcgccat gggaactccc gcagcgcctc caaaggcggt tctgaaactg    120
gagccgcagt ggattaatgt gttgcaggaa gatagcgtga cgctgacctg ccgtggaacc    180
catagcccgg aatcagacag cgtacagtgg tttcacaacg gcaatttgat ccccactcat    240
acgcagccga cgtaccgttt caaagccaac aataacgatt cgggcgaata tacctgccag    300
acaggccaga ccagcctgag cgatccagtg cacctgaccg tgctgtcaga atggctggtg    360
ctgcaaaccc cgcgtctgga atttcaggaa ggcgaaacca tagtgctgcg ttgccacagc    420
tggaaagata aaccgctggt gaaggtcacg ttcttccaga acgggaagag caagaagttc    480
tcccgtagcg acccgaattt tagcatcccc caggcgaatc atagccatag cggcgattat    540
cactgcaccg ggaatattgg gtatacgttg tatagcagca agccggttac tatcaccgtg    600
cagggcggcc atcatcatca tcatcat                                        627

<210> SEQ ID NO 162
```

-continued

<210> SEQ ID NO 162
<211> LENGTH: 33
<212> TYPE: DNA
<213> ORGANISM: Artificial Sequence
<220> FEATURE:
<223> OTHER INFORMATION: Oligonucleotide

<400> SEQUENCE: 162
ggtcaggtgc actggatccg acaggctggt ctg          33

<210> SEQ ID NO 163
<211> LENGTH: 33
<212> TYPE: DNA
<213> ORGANISM: Artificial Sequence
<220> FEATURE:
<223> OTHER INFORMATION: Oligonucleotide

<400> SEQUENCE: 163
cagaccagcc tgtcggatcc agtgcacctg acc          33

<210> SEQ ID NO 164
<211> LENGTH: 627
<212> TYPE: DNA
<213> ORGANISM: Artificial Sequence
<220> FEATURE:
<223> OTHER INFORMATION: DNA encoding MalE signal - FcgRIIb-m3 - 6His

<400> SEQUENCE: 164
atgaaaataa aaacaggtgc acgcatcctc gcattatccg cattaacgac gatgatgttt          60
tccgcctcgg ctctcgccat gggaactccc gcagcgcctc caaaggcggt tctgaaactg         120
gagccgcagt ggattaatgt gttgcaggaa gatagcgtga cgctgacctg ccgtggaacc         180
catagcccgg aatcagacag cgtacagtgg tttcacaacg gcaatttgat ccccactcat         240
acgcagccga cgtaccgttt caaagccaac aataacgatt cgggcgaata cacctgccag         300
acaggccaga ccagcctgtc ggatccagtg cacctgaccg tgctgtcaga atggctggtg         360
ctgcaaaccc cgcgtctgga atttcaggaa ggcgaaacca tagtgctgcg ttgccacagc         420
tggaaagata aaccgctggt gaaggtcacg ttcttccaga cgggaagag caagaagttc         480
tcccgtagcg acccgaattt tagcatcccc caggcgaatc atagccatag cggcgattat         540
cactgcaccg ggaatattgg gtatacgttg tatagcagca agccggttac tatcaccgtg         600
cagggcggcc atcatcatca tcatcat                                            627

<210> SEQ ID NO 165
<211> LENGTH: 209
<212> TYPE: PRT
<213> ORGANISM: Artificial Sequence
<220> FEATURE:
<223> OTHER INFORMATION: MalE signal - FcgRIIb-m6b - 6His

<400> SEQUENCE: 165

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Thr Pro Ala Ala
                20                  25                  30

Pro Pro Lys Ala Val Leu Lys Leu Glu Pro Gln Trp Ile Asn Val Leu
            35                  40                  45

Gln Glu Asp Ser Val Thr Leu Thr Cys Arg Gly Thr His Ser Pro Glu
        50                  55                  60

Ser Asp Ser Val Gln Trp Phe His Asn Gly Asn Leu Ile Pro Thr Gln
65                  70                  75                  80

```
Thr Gln Pro Thr Tyr Arg Phe Lys Ala Thr Ser Asn Asp Ser Gly Glu
             85                  90                  95

Tyr Thr Cys Gln Thr Gly Gln Thr Ser Leu Ser Asp Pro Val His Leu
        100                 105                 110

Thr Val Leu Ser Glu Trp Leu Val Leu Gln Thr Pro Arg Leu Glu Phe
            115                 120                 125

Gln Glu Gly Glu Thr Ile Val Leu Arg Cys His Ser Trp Lys Asp Lys
        130                 135                 140

Pro Leu Val Lys Val Thr Phe Phe Gln Asn Gly Lys Ser Lys Lys Phe
145                 150                 155                 160

Ser Arg Ser Asp Pro Asn Phe Ser Ile Pro Gln Ala Asn His Ser His
                165                 170                 175

Ser Gly Asp Tyr His Cys Thr Gly Asn Ile Gly Tyr Thr Leu Tyr Ser
            180                 185                 190

Ser Lys Pro Val Thr Ile Thr Val Gln Gly Gly His His His His His
        195                 200                 205

His
```

<210> SEQ ID NO 166
<211> LENGTH: 35
<212> TYPE: DNA
<213> ORGANISM: Artificial Sequence
<220> FEATURE:
<223> OTHER INFORMATION: Oligonucleotide

<400> SEQUENCE: 166
tcgcccgaat cgttactggt ggctttgaaa cggta                        35

<210> SEQ ID NO 167
<211> LENGTH: 35
<212> TYPE: DNA
<213> ORGANISM: Artificial Sequence
<220> FEATURE:
<223> OTHER INFORMATION: Oligonucleotide

<400> SEQUENCE: 167
taccgtttca agccaccag taacgattcg ggcga                         35

<210> SEQ ID NO 168
<211> LENGTH: 32
<212> TYPE: DNA
<213> ORGANISM: Artificial Sequence
<220> FEATURE:
<223> OTHER INFORMATION: Oligonucleotide

<400> SEQUENCE: 168
tacgtcggct gcgtttgagt ggggatcaaa tt                           32

<210> SEQ ID NO 169
<211> LENGTH: 32
<212> TYPE: DNA
<213> ORGANISM: Artificial Sequence
<220> FEATURE:
<223> OTHER INFORMATION: Oligonucleotide

<400> SEQUENCE: 169
aatttgatcc ccactcaaac gcagccgacg ta                           32

<210> SEQ ID NO 170
<211> LENGTH: 627
<212> TYPE: DNA
<213> ORGANISM: Artificial Sequence

```
<220> FEATURE:
<223> OTHER INFORMATION: DNA encoding MalE signal - FcgRIIb-m6b - 6His

<400> SEQUENCE: 170
atgaaaataa aaacaggtgc acgcatcctc gcattatccg cattaacgac gatgatgttt      60
tccgcctcgg ctctcgccat gggaactccc gcagcgcctc caaaggcggt tctgaaactg     120
gagccgcagt ggattaatgt gttgcaggaa gatagcgtga cgctgacctg ccgtggaacc     180
catagcccgg aatcagacag cgtacagtgg tttcacaacg gcaatttgat ccccactcaa     240
acgcagccga cgtaccgttt caaagccacc agtaacgatt cgggcgaata tacctgccag     300
acaggccaga ccagcctgtc ggatccagtg cacctgaccg tgctgtcaga atggctggtg     360
ctgcaaaccc cgcgtctgga atttcaggaa ggcgaaacca tagtgctgcg ttgccacagc     420
tggaaagata aaccgctggt gaaggtcacg ttcttccaga acgggaagag caagaagttc     480
tcccgtagcg acccgaattt tagcatcccc caggcgaatc atagccatag cggcgattat     540
cactgcaccg ggaatattgg gtatacgttg tatagcagca agccggttac tatcaccgtg     600
cagggcggcc atcatcatca tcatcat                                         627

<210> SEQ ID NO 171
<211> LENGTH: 37
<212> TYPE: DNA
<213> ORGANISM: Artificial Sequence
<220> FEATURE:
<223> OTHER INFORMATION: Oligonucleotide

<400> SEQUENCE: 171
tagccatggg catgcgtacc gaagatctgc cgaaagc                               37

<210> SEQ ID NO 172
<211> LENGTH: 67
<212> TYPE: DNA
<213> ORGANISM: Artificial Sequence
<220> FEATURE:
<223> OTHER INFORMATION: Oligonucleotide

<400> SEQUENCE: 172
cccaagctta tccgcaggta tcgttgcggc agccctgcac ggtgatagta accggcttgc      60
tgctata                                                                67

<210> SEQ ID NO 173
<211> LENGTH: 19
<212> TYPE: DNA
<213> ORGANISM: Artificial Sequence
<220> FEATURE:
<223> OTHER INFORMATION: Oligonucleotide

<400> SEQUENCE: 173
tgtggtatgg ctgtgcagg                                                   19

<210> SEQ ID NO 174
<211> LENGTH: 18
<212> TYPE: DNA
<213> ORGANISM: Artificial Sequence
<220> FEATURE:
<223> OTHER INFORMATION: Oligonucleotide

<400> SEQUENCE: 174
tcggcatggg gtcaggtg                                                    18

<210> SEQ ID NO 175
```

```
<211> LENGTH: 205
<212> TYPE: PRT
<213> ORGANISM: Artificial Sequence
<220> FEATURE:
<223> OTHER INFORMATION: pTrc-Am6_Cys

<400> SEQUENCE: 175

Met Lys Tyr Leu Leu Ser Thr Ala Ala Ala Gly Leu Leu Leu Leu Ala
1               5                   10                  15

Ala Gln Pro Ala Met Ala Met Gly Gln Ala Ala Pro Pro Lys Ala
            20                  25                  30

Val Leu Lys Leu Glu Pro Pro Trp Ile Asn Val Leu Gln Glu Asp Ser
        35                  40                  45

Val Thr Leu Thr Cys Gln Gly Ala Arg Ser Pro Glu Ser Asp Ser Val
    50                  55                  60

Gln Trp Phe His Asn Gly Asn Leu Ile Pro Thr Gln Thr Gln Pro Thr
65                  70                  75                  80

Tyr Arg Phe Lys Ala Thr Ser Asn Asp Ser Gly Glu Tyr Thr Cys Gln
                85                  90                  95

Thr Gly Gln Thr Ser Leu Ser Asp Pro Val His Leu Thr Val Leu Ser
            100                 105                 110

Glu Trp Leu Val Leu Gln Thr Pro Arg Leu Glu Phe Gln Glu Gly Glu
        115                 120                 125

Thr Ile Met Leu Arg Cys His Ser Trp Lys Asp Lys Pro Leu Val Lys
    130                 135                 140

Val Thr Phe Phe Gln Asn Gly Lys Ser Gln Lys Phe Ser His Leu Asp
145                 150                 155                 160

Pro Thr Phe Ser Ile Pro Gln Ala Asn His Ser His Ser Gly Asp Tyr
                165                 170                 175

His Cys Thr Gly Asn Ile Gly Tyr Thr Leu Phe Ser Ser Lys Pro Val
            180                 185                 190

Thr Ile Thr Val Gln Gly Cys Arg Asn Asp Thr Cys Gly
    195                 200                 205

<210> SEQ ID NO 176
<211> LENGTH: 615
<212> TYPE: DNA
<213> ORGANISM: Artificial Sequence
<220> FEATURE:
<223> OTHER INFORMATION: Oligonucleotide

<400> SEQUENCE: 176
atgaaatacc tgctgtcgac cgctgctgct ggtctgctgc tcctcgctgc ccagccggcg      60
atggccatgg gacaagccgc agcgcctcca aaggcggttc tgaaactgga gccgccgtgg     120
attaatgtgt tgcaggaaga tagcgtgacg ctgacctgcc agggagcccg tagcccggaa     180
tcagacagcg tacagtggtt tcacaacggc aatttgatcc ccactcaaac gcagccgacg     240
taccgtttca agccaccagt aacgattcgg gcgaatatat cctgccagac aggccagacc     300
agcctgtcgg atccagtgca cctgaccgtg ctgtcagaat ggctggtgct gcaaaccccg     360
cgtctggaat tccaggaagg cgaaaccata atgctgcgtt gccacagctg aaagataaa     420 ccgctggtga aggtcacgtt cttccagaac gggaagagcc agaagttctc ccatctcgac     480 ccgacttta gcatccccca ggcgaatcat agccatagcg gcgattatca ctgcaccggg     540
aatattgggt atacgttgtt tagcagcaag ccggttacta tcaccgtgca gggctgccgc     600
aacgatacct gcgga                                                     615
```

RECOMBINANT FCγRII

FIELD

The present invention relates to improved recombinant FcγRIIb and improved recombinant FcγRIIa having increased productivity and thermal stability, derived from human Fcγ receptor (hereunder, "FcγR") IIb (CD32b) and FcγRIIa (CD32a), which have binding affinity for immunoglobulin G (IgG).

BACKGROUND

FcγR is a receptor group that mediates intracellular signal transduction by binding to IgG immune complexes, which are conjugates of antigen and IgG (NPL 1). Human FcγR can be classified into subtypes, of which FcγRI (CD64), FcγRIIa (CD32a), FcγRIIb (CD32b), FcγRIIc (CD32c), FcγRIIIa (CD16a) and FcγRIIIb (CD16b) have been reported (NPLs 1 to 3).

Binding between an IgG immune complex and FcγR occurs by binding of the FcγR to the Fc region of the IgG. Individual FcγR molecular species have an IgG Fc region-recognizing domain that recognizes a single IgG belonging to the same subtype. This determines which accessory cells will be recruited for each individual immune response (NPLs 1 to 3). Among the FcγR subtypes, FcγRIIb mediates signal transduction that inhibits cell activation, thus differing from other FcγR subtypes that mediate cell-activating signal transduction (NPLs 1 to 3). FcγRIIa is one of the activating FcγR, which is expressed by macrophages, platelets, neutrophils, monocytes and dendritic cells. FcγRIIc is also an activating FcγR, which is expressed by natural killer cells.

Mature FcγR protein is composed of an extracellular domain that binds with the Fc region of IgG, a transmembrane domain, and an intracellular domain involved in signal transduction. The amino acid sequences of the extracellular domains of FcγRIIb and FcγRIIc are identical. The amino acid sequences of the extracellular domains of FcγRIIa and FcγRIIb are also highly homologous.

Recombinant protein from human FcγRIIb (hereunder referred to as "recombinant FcγRIIb") has potential applications in diagnosis, medicine and crystal structure analysis, as well as for chromatography materials for use in antibody separation and concentration (PTLs 1 to 4). Some research has already been carried out for preparation of recombinant FcγRIIb using *Escherichia coli* (*E. coli*) hosts, and PTLs 1 to 4 report on preparation methods for regeneration (refolding) of recombinant FcγRIIb expressed as inclusion bodies (insoluble form) by *E. coli* hosts.

Recombinant protein from human FcγRIIa (hereunder referred to as "recombinant FcγRIIa") also has potential applications in diagnosis, medicine and crystal structure analysis, as well as for chromatography materials for use in antibody separation and concentration. Some research has already been carried out for preparation of recombinant FcγRIIa using *E. coli* hosts, and NPLs 4 and 5 report on preparation methods for regeneration (refolding) of recombinant FcγRIIa expressed as inclusion bodies (insoluble form) by *E. coli* hosts.

However, refolding usually requires a complex procedure and long operating time, and therefore its efficiency is low (NPL 6).

For industrial application of recombinant FcγRIIb and FcγRIIa, it is preferred for the recombinant FcγRIIb and FcγRIIa to exhibit high stability under various conditions (heat, acidity, alkalinity, etc.), from the viewpoint of their use and storage. However, increased stabilization of recombinant FcγRIIb and FcγRIIa has not yet been achieved.

CITATION LIST

Patent Literature

[PTL 1] JP2002-531086A
[PTL 2] JP2005-515981A
[PTL 3] JP2011-105716A
[PTL 4] JP2012-188456A

Non Patent Literature

[NPL 1] T. Takai, Jpn. J. Clin. Immunol., 28, 318-326, 2005
[NPL 2] J. V. Ravetch et al., Annu. Rev. Immunol., 9, 457-492, 1991
[NPL 3] P. Bruhns, BLOOD, 119, 5640-5649, 2012
[NPL 4] P. Sondermann et al., J. Mol. Biol., 309, 737-749, 2001
[NPL 5] S. T. Jung et al., Biotechnol. Bioeng., 107, 21-30, 2010
[NPL 6] H. Yamaguchi & M. Miyazaki, Biomolecules, 4, 235-251, 2014

SUMMARY

Technical Problem

It is an object of the invention to provide improved recombinant FcγRIIb and FcγRIIa that do not require refolding and that have high productivity and thermal stability, as well as a method for producing them.

Solution to Problem

As a result of avid research, the present inventors have found that by replacing specific amino acids of the constituent amino acids of recombinant FcγRIIb and FcγRIIa with other specific amino acids and expressing them with an *E. coli* host in soluble form, it is possible to provide improved recombinant FcγRIIb and FcγRIIa that do not require refolding and that have high productivity and thermal stability, and the invention has been completed upon this finding.

Specifically, the present invention can be exemplified by the following.

[1] An improved recombinant FcγRII selected from the following (i) to (iii):

(i) Improved recombinant FcγRIIb comprising at least the amino acid residues from position 29 to position 201 of the amino acid sequence set forth in SEQ ID NO: 1, wherein at least one of the following amino acid substitutions (1) to (6) is included in the amino acid residues from position 29 to position 201:

(1) A substitution of valine for isoleucine at position 68 of SEQ ID NO: 1;
(2) A substitution of glutamine for histidine at position 80 of SEQ ID NO: 1;
(3) A substitution of threonine for serine at position 84 of SEQ ID NO: 1;
(4) A substitution of threonine for asparagine at position 90 of SEQ ID NO: 1;
(5) A substitution of serine for asparagine at position 91 of SEQ ID NO: 1;
(6) A substitution of arginine for histidine at position 125 of SEQ ID NO: 1;

(ii) Improved recombinant FcγRIIa comprising at least the amino acid residues from position 29 to position 201 of the amino acid sequence set forth in SEQ ID NO: 88, wherein at least one of the following amino acid substitutions (7) to (12) are included in the amino acid residues from position 29 to position 201:

(7) A substitution of valine for isoleucine at position 68 of SEQ ID NO: 88;

(8) A substitution of glutamine for histidine at position 80 of SEQ ID NO: 88;

(9) A substitution of threonine for senile at position 84 of SEQ ID NO: 88;

(10) A substitution of threonine for asparagine at position 90 of SEQ ID NO: 88;

(11) A substitution of serine for asparagine at position 91 of SEQ ID NO: 88;

(12) A substitution of arginine for histidine at position 125 of SEQ ID NO: 88;

(iii) Improved recombinant FcγRII consisting of an amino acid sequence of the improved recombinant FcγRII of the above (i) or (ii) in which one or more amino acid residues in a region other than positions substituted by the substitutions (1) to (12) have been deleted, substituted or added, and having affinity for IgG.

[2] The improved recombinant FcγRII according to [1], which is the improved recombinant FcγRII selected from the following (iv) to (vi):

(iv) Improved recombinant FcγRIIb comprising at least the amino acid residues from position 29 to position 201 of the amino acid sequence set forth in SEQ ID NO: 1, wherein at least the following amino acid substitution (1) is included in the amino acid residues from position 29 to position 201:

(1) A substitution of valine for isoleucine at position 68 of SEQ ID NO: 1;

(v) Improved recombinant FcγRIIa comprising at least the amino acid residues from position 29 to position 201 of the amino acid sequence set forth in SEQ ID NO: 88, wherein at least the following amino acid substitution (7) is included in the amino acid residues from position 29 to position 201:

(7) A substitution of valine for isoleucine at position 68 of SEQ ID NO: 88;

(vi) Improved recombinant FcγRII consisting of an amino acid sequence of the improved recombinant FcγRII of the above (iv) or (v) in which one or more amino acid residues in a region other than the position substituted by the substitution of the above (1) or (7) have been deleted, substituted or added, and having affinity for IgG.

[3] The improved recombinant FcγRII according to [1], which is selected from the following (vii) to (ix):

(vii) Improved recombinant FcγRIIb comprising at least the amino acid residues from position 29 to position 201 of the amino acid sequence set forth in any one of SEQ ID NOs: 2 to 11;

(viii) Improved recombinant FcγRIIa comprising at least the amino acid residues from position 29 to position 201 of the amino acid sequence set forth in SEQ ID NO: 89;

(ix) Improved recombinant FcγRII consisting of an amino acid sequence of the improved recombinant FcγRII of the above (vii) or (viii) in which one or more amino acid residues in a region other than positions substituted by the substitutions (1) to (12) have been deleted, substituted or added, and having affinity for IgG.

[4] DNA encoding the improved recombinant FcγRII according to any one of [1] to [3].

[5] A recombinant vector comprising the DNA according to [4].

[6] A transformant capable of producing an improved recombinant FcγRII, obtained by transforming a host with the recombinant vector according to [5].

[7] The transformant according to [6], wherein the host is E. coli.

[8] A method for producing an improved recombinant FcγRII, comprising two steps of: culturing a transformant according to [6] or [7] to produce improved recombinant FcγRII; and collecting the improved recombinant FcγRII that is produced from the obtained cultured product.

[9] An adsorbent obtained by immobilizing the improved recombinant FcγRII according to any one of [1] to [3] on an insoluble support.

[10] A method for separating an antibody, comprising two steps of: adding an antibody-containing solution to a column packed with an adsorbent according to [9], thereby adsorbing the antibody onto the adsorbent; and eluting the adsorbed antibody by use of an eluent.

The present invention will now be explained in greater detail.

1. Improved Recombinant FcγRIIb of the Invention

The improved recombinant FcγRIIb of the invention will now be described.

The improved recombinant FcγRIIb of the first invention is (a) the improved recombinant FcγRIIb comprising at least the amino acid residues from position 29 to position 201 of the amino acid sequence set forth in SEQ ID NO: 1, wherein at least one of the substitutions (1) to (6) is included in the amino acid residues from position 29 to position 201; or (b) the improved recombinant FcγRIIb consisting of an amino acid sequence of the above (a) in which one or more amino acid residues in a region other than positions substituted by the substitutions (1) to (6) have been deleted, substituted or added.

The amino acid sequence set forth in SEQ ID NO: 1 will now be explained. The amino acid sequence set forth in SEQ ID NO: 1 is the amino acid sequence of a recombinant protein (recombinant FcγRIIb) derived from the extracellular domain of human FcγRIIb (SEQ ID NO: 12, UniProt No. P31994). The amino acid sequence from the methionine at position 1 to alanine at position 26 at the N-terminal end of SEQ ID NO: 1 is a signal sequence (MalE signal sequence) for secretory expression into the periplasm of E. coli, the amino acid sequence from methionine at position 27 to glycine at position 28 is a linker sequence, the amino acid sequence from threonine at position 29 to glutamine at position 201 is a sequence derived from the amino acid sequence of the extracellular domain of human FcγRIIb (SEQ ID NO: 12) (threonine at position 43 to glutamine at position 215 at the N-terminal end of the amino acid sequence set forth in SEQ ID NO: 12), the amino acid sequence from glycine at position 202 to glycine at position 203 is a linker sequence, and the amino acid sequence from histidine at position 204 to histidine at position 209 is a polyhistidine sequence.

Substitutions (1) to (6) have the effect of increasing productivity (expression level) by transformants in the production of improved recombinant FcγRIIb according to the first invention. Productivity of the improved recombinant FcγRIIb according to the first invention is therefore higher productivity than recombinant FcγRIIb consisting of the amino acid sequence set forth in SEQ ID NO: 1. In order to further increase productivity of improved recombinant FcγRIIb according to the first invention by transformants, it preferably has multiple substitutions among substitutions (1) to (6), and more preferably it has all of them.

Substitutions (1) to (6) also have the effect of increasing the thermal stability of the improved recombinant FcγRIIb according to the first invention. Thermal stability of the improved recombinant FcγRIIb according to the first invention is therefore higher thermal stability than recombinant FcγRIIb consisting of the amino acid sequence set forth in SEQ ID NO: 1. In order to further increase the thermal stability of improved recombinant FcγRIIb according to the first invention, it preferably has multiple substitutions among substitutions (1) to (6), and more preferably it has all of them.

A preferred example of the improved recombinant FcγRIIb according to the first invention is improved FcγRIIb according to the second invention, i.e. (a'): improved recombinant FcγRIIb comprising at least the amino acid residues from position 29 to position 201 of the amino acid sequence set forth in SEQ ID NO: 1, wherein at least the substitution (1) is included in the amino acid residues from position 29 to position 201, or (b'): improved recombinant FcγRIIb consisting of an amino acid sequence of the improved recombinant FcγRIIb of the above (a') in which one or more amino acid residues in a region other than the position substituted by the substitution (1) have been deleted, substituted or added, and having affinity for IgG.

As another preferred example of improved recombinant FcγRIIb according to the first invention, is improved recombinant FcγRIIb according to the third invention, i.e. (c): improved recombinant FcγRIIb comprising at least the amino acid residues from position 29 to position 201 of the amino acid sequence represented by any of:

SEQ ID NO: 2 (including substitution (3)),
SEQ ID NO: 3 (including substitution (6)),
SEQ ID NO: 4 (including substitution (1)),
SEQ ID NO: 5 (including substitution (1), substitution (3) and substitution (6)),
SEQ ID NO: 6 (including substitution (1), substitution (3), substitution (5) and substitution (6)),
SEQ ID NO: 7 (including substitution (1), substitution (3), substitution (4) and substitution (6)),
SEQ ID NO: 8 (including substitution (1), substitution (2), substitution (3) and substitution (6)),
SEQ ID NO: 9 (including substitution (1), substitution (2), substitution (3), substitution (5) and substitution (6)),
SEQ ID NO: 10 (including substitution (1), substitution (3), substitution (4), substitution (5) and substitution (6)), and
SEQ ID NO: 11 (including substitution (1), substitution (2), substitution (3), substitution (4), substitution (5) and substitution (6));
or (d): improved recombinant FcγRIIb consisting of an amino acid sequence of the improved recombinant FcγRIIb of the above (c) in which one or more amino acid residues in a region other than positions substituted by the substitutions (1) to (6) have been deleted, substituted or added, and having affinity for IgG.

The improved recombinant FcγRIIb according to the first to third inventions preferably has a signal sequence at the N-terminal end that promotes soluble expression in an expression host. When the host is *E. coli*, for example, it preferably has a signal sequence for secretory expression into the periplasm of *E. coli*. The signal sequence for secretory expression into the periplasm of *E. coli* may be one that is publicly known from the literature, such as MalE signal sequence (for example, S. H. Yoon et al., Recent Pat. Biotechnol., 4, 23-29, 2010). However, if only an effect of increasing thermal stability by substitutions (1) to (6) is desired, then the improved recombinant FcγRIIb according to the first to third inventions does not need to have a signal sequence at the N-terminal end that promotes soluble expression in the expression host.

As long as affinity for IgG is maintained, the improved recombinant FcγRIIb according to the first to third inventions may have a deletion, substitution or addition of one or more amino acids in a region other than a position substituted by substitutions (1) to (6) (or in other words, additionally, while retaining the substitutions (1) to (6)). For example, the portion of the amino acid sequence set forth in SEQ ID NO: 1 corresponding to the MalE signal sequence, which is a signal for secretory expression into the periplasm of *E. coli* (sometimes also including an adjacent linker sequence), may be substituted by another signal sequence such as PelB, DsbA or TorT (S. H. Yoon et al., Recent Pat. Biotechnol., 4, 23-29, 2010), or the portion corresponding to the MalE signal sequence may be deleted. Alternatively, for example, the portion of the amino acid sequence set forth in SEQ ID NO: 1 corresponding to the polyhistidine sequence (sometimes including an adjacent linker sequence) may be substituted by another sequence (for example, an oligopeptide such as polylysine, polyarginine, polyglutamic acid, polyaspartic acid, or a cysteine tag comprising the amino acid residues from arginine at position 200 to glycine at position 205 of SEQ ID NO: 86), or the portion corresponding to the polyhistidine sequence may be deleted. In addition, the amino acid sequence of a protein with another function such as glutathione S-transferase or maltose-binding protein may be added to the improved recombinant FcγRIIb according to the first to third inventions, to form a fusion protein. The number of amino acid residues that may be deleted, substituted or added in the portion corresponding to the amino acid residues from threonine at position 29 to glutamine at position 201 of the amino acid sequence set forth in SEQ ID NO: 1 is preferably 1 to 10 and more preferably 1 to 5. The amino acid deletion, substitution or addition may be carried out using a genetic engineering method known to those skilled in the art.

The affinity for IgG of the improved recombinant FcγRIIb according to the first to third inventions can be evaluated by Enzyme-Linked ImmunoSorbent Assay (ELISA) (for example, ELISA method 1 described below), or a surface plasmon resonance method (P. Bruhns et al., Blood, 113, 3716-3725, 2009).

ELISA method 1 will now be described. In ELISA method 1, IgG (product of Kaketsuken) is prepared to a concentration of 10 μg/mL with 50 mM Tris-HCl buffer (pH 8.0), and then added into each well of a 96-well microplate (MaxiSorp, Nunc) at 100 μL/well, and the IgG is immobilized (at 4° C. for 18 hours). After immobilization is complete, the solution in each well is discarded and TBS-B buffer (20 mM Tris-HCl (pH 8.0) containing 137 mM NaCl, 2.68 mM KCl and 0.5% (w/v) bovine serum albumin) is added to each well for blocking (at 30° C. for 2 hours). After rinsing each well with rinsing buffer (20 mM Tris-HCl buffer (pH 7.5) containing 0.05% (w/v) Tween 20 and 150 mM NaCl), sample solution containing the improved recombinant FcγRIIb is added to the wells and reaction with the immobilized IgG is conducted (at 30° C. for 1.5 hours). Upon completion of the reaction, each well is rinsed with rinsing buffer, horseradish peroxidase-labeled anti-His-Tag antibody reagent (product of Bethyl) (diluted with 50 mM Tris-HCl buffer (pH 8.0)) is added to each well, and reaction is conducted at 30° C. for 1.5 hours. After the reaction, each well is rinsed with rinsing buffer, TMB Peroxidase Substrate (product of KPL) is added to each well, and the absorbance at 450 nm is measured.

The fourth to eighth inventions will now be explained. DNA according to the fourth invention can be obtained by a method of modifying cDNAs of human FcγRIIb or other FcγR (such as FcγRIIa or FcγRIIc) utilizing a DNA amplification method such as Polymerase Chain Reaction (PCR), a method of converting the amino acid sequences of human FcγRIIb or other FcγR (such as FcγRIIa or FcγRIIc) to base sequences, artificially preparing DNA including the base sequences, and using a DNA amplification method for further modifying preparation, or a method of converting the amino acid sequences set forth in SEQ ID NO: 2 to SEQ ID NO: 11 to base sequences and artificially preparing DNA that includes the base sequences. When converting amino acid sequences to base sequences in these methods, it is preferred to take into account the frequency of use of the codons of the microorganisms and cells (host) utilized for production of the improved recombinant FcγRIIb according to the first to third inventions. As an example, when the host used is $E.\ coli$, the usage frequencies of AGA, AGG, CGG or CGA for arginine (Arg), ATA for isoleucine (Ile), CTA for leucine (Leu), GGA for glycine (Gly) and CCC for proline (Pro) are low, i.e. they are rare codons, and therefore codons other than these codons are preferably selected for the conversion. Incidentally, analysis of codon usage frequency may be made utilizing the Codon Usage Database http://www.kazusa.or.jp/codon/, access date: Jun. 21, 2016) at the home page of the Kazusa DNA Research Institute, for example.

When preparing DNA for the fourth invention using a DNA amplification method, a mutagenesis method using an error-prone PCR method may be employed. The reaction conditions for the error-prone PCR method are not particularly restricted so long as they are conditions allowing introduction of the desired mutation into the DNA, and for example, PCR may be carried out in which non-homogeneous concentrations of the four different deoxynucleotides (dATP/dTTP/dCTP/dGTP) as substrates are prepared, and $MnCl_2$ is added to the PCR reaction mixture at concentrations from 0.01 to 10 mM and preferably 0.1 to 1 mM.

Specific examples of DNA according to the fourth invention include:

DNA consisting of the base sequence set forth in SEQ ID NO: 13 encoding the amino acid sequence set forth in SEQ ID NO: 2, DNA consisting of the base sequence set forth in SEQ ID NO: 14 encoding the amino acid sequence set forth in SEQ ID NO: 3, DNA consisting of the base sequence set forth in SEQ ID NO: 15 encoding the amino acid sequence set forth in SEQ ID NO: 4, DNA consisting of the base sequences of SEQ ID NO: 16 and 17 encoding the amino acid sequence set forth in SEQ ID NO: 5, DNA consisting of the base sequence set forth in SEQ ID NO: 18 encoding the amino acid sequence set forth in SEQ ID NO: 6, DNA consisting of the base sequence set forth in SEQ ID NO: 19 encoding the amino acid sequence set forth in SEQ ID NO: 7, DNA consisting of the base sequence set forth in SEQ ID NO: 20 encoding the amino acid sequence set forth in SEQ ID NO: 8, DNA consisting of the base sequence set forth in SEQ ID NO: 21 encoding the amino acid sequence set forth in SEQ ID NO: 9, DNA consisting of the base sequence set forth in SEQ ID NO: 22 encoding the amino acid sequence set forth in SEQ ID NO: 10, and DNA consisting of the base sequence set forth in SEQ ID NO: 23 encoding the amino acid sequence set forth in SEQ ID NO: 11.

For transformation of a host using DNA according to the fourth invention, transformation may be carried out using the actual DNA of the invention, but from the viewpoint of allowing stable transformation to be carried out, preferably the DNA of the fourth invention is inserted at an appropriate position in a vector based on a bacteriophage, cosmid or plasmid commonly used for transformation of prokaryotic cells or eukaryotic cells to prepare a recombinant vector according to the fifth invention, which is used for transformation. The "appropriate location" is a location where the replicating function of the recombinant vector, the desired antibiotic marker and the transfer-associated regions are not destroyed. When the DNA of the fourth invention is inserted into the vector, preferably it is inserted into the vector in a state linked to functional DNA such as a promoter necessary for expression.

The vector used for the fifth invention is not particularly restricted so long as it is stably present and can replicate in the host, and when $E.\ coli$ is used as the host, it may be a pET vector, pUC vector, pTrc vector, pCDF vector or pBBR vector, for example. Promoters to be used for the invention include, for $E.\ coli$ as the host for example, trp promoter, tac promoter, trc promoter, lac promoter, T7 promoter, recA promoter and lpp promoter, as well as the λ phage λPL promoter and λPR promoter.

Transformants according to the sixth invention or seventh invention may be obtained by transforming the host using a recombinant vector according to the fifth invention. A transformant according to the sixth invention or seventh invention includes a recombinant vector according to the fifth invention.

There are no particular restrictions on the host to be used for the sixth invention, but $E.\ coli$ (a mode of the seventh invention) is preferred from the viewpoint of facilitating experimentation for genetic engineering. Transformation of a host using a recombinant vector of the fifth invention may be carried out by any method commonly used by those skilled in the art, and for example, when $E.\ coli$ ($E.\ coli$ JM109, $E.\ coli$ BL21(DE3), $E.\ coli$ NiCo21(DE3), $E.\ coli$ W3110 or the like) is selected as the host, a method described in the published literature may be used (for example, Molecular Cloning, Cold Spring Harbor Laboratory, 256, 1992). A recombinant vector according to fifth invention may be extracted from the transformant of the sixth invention or seventh invention using an appropriate extraction method or commercially available kit. When the host is $E.\ coli$, for example, an alkaline extraction method or a commercially available extraction kit such as a QIAprep Spin Miniprep kit (trade name of Qiagen Inc.) may be used.

The eighth invention is a method of producing improved recombinant FcγRIIb according to the first to third inventions using a transformant according to the sixth invention or seventh invention, and it includes two steps of: culturing the transformant to produce improved recombinant FcγRIIb according to the first to third inventions (hereunder referred to as the "first step"); and collecting the improved recombinant FcγRIIb according to the first to third inventions from the obtained cultured product (hereunder referred to as the "second step"). Throughout the present specification, the term "cultured product" includes the cultured transformants themselves and their cellular secretion products, as well as the culture medium used for culturing.

In the first step of the eighth invention, culturing of the transformant may be carried out in medium suited for its culturing. For example, when *E. coli* is used as the host (that is, the mode of the seventh invention), it is preferred to use Luria-Bertani (LB) culture medium supplemented with the necessary nutrients. When the recombinant vector of the fifth invention includes an antibiotic resistance gene, the antibiotic corresponding to the gene may be added to the culture medium and the first step carried out to allow selective growth of the transformant, a preferred example being, when the recombinant vector includes a kanamycin resistance gene, addition of kanamycin to the culture medium.

A carbon, nitrogen and inorganic salt source, as well as appropriate nutrients, are added to the culture medium, but a reagent such as glycine may also be added to promote secretion of protein from the transformant of the sixth invention or seventh invention into the culture solution. When the host is *E. coli* (a transformant of the seventh invention is used), the added glycine concentration may be in a range that does not affect growth, and it is preferably no greater than 10% (w/v) and more preferably 0.1% (w/v) to 2% (w/v), with respect to the culture medium. The culturing temperature may be a temperature commonly known for the host used, and when the host is *E. coli* (a transformant of the seventh invention is used), for example, it is 10° C. to 40° C. and preferably 20° C. to 37° C., being appropriately set in consideration of the desired amount of production of the improved recombinant FcγRIIb according to the first to third inventions. The medium pH may be any pH range commonly known for the host used, and when the host is *E. coli* (a transformant of the seventh invention is used), for example, it is in the range of pH 6.8 to pH 7.4 and preferably about pH 7.0, being appropriately set in consideration of the desired amount of production of the improved recombinant FcγRIIb according to the first to third inventions.

When an inducible promoter has been introduced into a recombinant vector of the fifth invention, an inducer may be added to the culture medium to induce expression under conditions allowing satisfactory production by the first to third inventions. An example of a preferred inducer is isopropyl-β-D-thiogalactopyranoside (IPTG), added to a concentration in the range of 0.005 to 1.0 mM and preferably the range of 0.01 to 0.5 mM. Expression induction by IPTG addition may be carried out under conditions commonly known for the host used.

In the second step of the eighth invention, the improved recombinant FcγRIIb according to the first to third inventions is collected from the cultured product obtained by the first step by a commonly known collection method. For example, when the improved recombinant FcγRIIb according to the first to third inventions is produced by secretion in the culture solution, the cells may be separated by a centrifugal separation procedure and the improved recombinant FcγRIIb according to the first to third inventions may be collected from the obtained culture supernatant, or when it is expressed intracellularly (including in the periplasm for prokaryotes), the cells may be collected by a centrifugal separation procedure, after which an enzymatic treatment agent or surfactant may be added to disrupt the cells, and the product collected from the cell disruptate.

The improved recombinant FcγRIIb according to the first to third inventions may be collected from the cultured product of the host according to the eighth invention, in the manner described above. When the collected improved recombinant FcγRIIb according to the first to third inventions is to be further increased in purity, a commonly known purification method may be used. Isolation and purification using liquid chromatography may be mentioned, in which case it is preferred to use ion-exchange chromatography, hydrophobic interaction chromatography, gel filtration chromatography or affinity chromatography, and more preferably these chromatography methods are combined for purification.

An adsorbent according to the ninth invention can be produced by immobilizing the improved FcγRIIb of the first invention to third invention to an insoluble support. There are no particular restrictions on the insoluble support, and examples include supports where the starting material is a polysaccharide such as agarose, alginate, carrageenan, chitin, cellulose, dextrin, dextran or starch, supports where the starting material is a synthetic polymer such as polyvinyl alcohol polymethacrylate, poly(2-hydroxyethyl methacrylate) or polyurethane, and supports where the starting material is a ceramic such as silica. Preferred among these as the insoluble support are supports where the starting material is a polysaccharide and supports where the starting material is a synthetic polymer. Examples of preferred supports include hydroxyl-introduced polymethacrylate gels such as TOYOPEARL (by Tosoh Corp.), agarose gels such as Sepharose (by GE Healthcare), and cellulose gels such as CELLUFINE (by JNC). There are no particular restrictions on the form of the insoluble support, and it may be granular, non-granular, porous or non-porous.

For immobilization of the improved FcγRIIb of the first invention to third invention on the insoluble support, the insoluble support may be provided with active groups such as N-hydroxysuccinic acid imide (NHS) activated ester groups, epoxy, carboxyl, maleimide, haloacetyl, tresyl, formyl and haloacetamide groups, immobilization being accomplished by covalent bonding between the human Fc-binding protein and insoluble support through the active groups. The support with the active groups may be a commercially available support used as is, or it may be prepared by introducing active groups onto the support surface under appropriate reaction conditions. Examples of commercially available supports with active groups include TOYOPEARL AF-Epoxy-650M and TOYOPEARL AF-Tresyl-650M (both by Tosoh Corp.), HiTrap NHS-activated HP Columns, NHS-activated Sepharose 4 Fast Flow and Epoxy-activated Sepharose 6B (all by GE Healthcare), and SulfoLink Coupling Resin (by Thermo Fisher Scientific).

Examples of methods for introducing active groups onto the support surface, on the other hand, include methods in which one site of a compound with two or more active sites is reacted with hydroxyl, epoxy, carboxyl and amino groups present on the support surface. Compounds having epoxy groups introduced onto hydroxyl or amino groups on the support surface, as examples of such compounds, include epichlorhydrin, ethanediol diglycidyl ether, butanediol diglycidyl ether and hexanediol diglycidyl ether. Compounds that introduce carboxyl groups onto the support surface after epoxy groups have been introduced onto the support surface by the compound, include 2-mercaptoacetic acid, 3-mercaptopropionic acid, 4-mercaptobutyric acid, 6-mercaptobutyric acid, glycine, 3-aminopropionic acid, 4-aminobutyric acid and 6-aminohexanoic acid.

Examples of compounds that introduce maleimide groups onto hydroxyl or epoxy, carboxyl or amino groups present on the support surface include N-(ε-maleimidecaproic acid) hydrazide, N-(ε-maleimidepropionic acid)hydrazide, 4-(4-

N-maleimidephenyl)acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimide)phenylisocyanato, 2-maleimideacetic acid, 3-maleimidepropionic acid, 4-maleimidebutyric acid, 6-maleimidehexanoic acid, (N-[α-maleimideacetoxy])succinimide ester, (m-maleimidebenzoyl) N-hydroxysuccinimide ester, (succinimidyl-4-[maleimidemethyl])cyclohexane-1-carbonyl-[6-aminohexanoic acid], (succinimidyl-4-[maleimidemethyl]) cyclohexane-1-carboxylic acid, (p-maleimidebenzoyl)N-hydroxysuccinimide ester and (m-maleimidebenzoyl)N-hydroxysuccinimide ester.

Examples of compounds that introduce haloacetyl groups onto hydroxyl or amino groups present on the support surface include chloroacetic acid, bromoacetic acid, iodoacetic acid, chloroacetic acid chloride, bromoacetic acid chloride, bromoacetic acid bromide, chloroacetic anhydride, bromoacetic anhydride, iodoacetic anhydride, 2-(iodoacetamide)acetic acid-N-hydroxysuccinimide ester, 3-(bromoacetamide)propionic acid-N-hydroxysuccinimide ester and 4-(iodoacetyl)aminobenzoic acid-N-hydroxysuccinimide ester. There may also be mentioned methods in which an ω-alkenylalkaneglycidyl ether is reacted with hydroxyl or amino groups present on the support surface, and then the ω-alkenyl site is halogenated with a halogenating agent and activated. Examples of ω-alkenylalkaneglycidyl ethers include allyl glycidyl ether, 3-butenyl glycidyl ether and 4-pentenyl glycidyl ether, and examples of halogenating agents include N-chlorosuccinimide, N-bromosuccinimide and N-iodosuccinimide.

A different example of a method for introducing active groups onto the support surface, is a method in which activated groups are introduced onto the carboxyl groups present on the support surface, using a condensation agent and an additive. Examples of condensation agents include 1-ethyl-3-(3-dimethylaminopropyl)carbodiimide (EDC), dicyclohexylcarbodiamide and carbonyldiimidazole. Examples of additives include N-hydroxysuccinic acid imide (NHS), 4-nitrophenol and 1-hydroxybenzotriazole.

Examples for the buffering solution to be used during immobilization of the improved FcγRIIb of the first invention to third invention on the insoluble support include acetate buffer, phosphate buffer, MES (2-Morpholinoethanesulfonic acid) buffer, HEPES (4-(2-hydroxyethyl)-1-piperazine-ethanesulfonic acid) buffer, Tris buffer and borate buffer. The reaction temperature for immobilization may be appropriately set in a temperature range from 5° C. to 50° C., and is preferably in the range of 10° C. to 35° C., from the viewpoint of the reactivity of the active groups and the stability of the Fc-binding protein of the invention.

For isolation of the antibody using the adsorbent of the ninth invention (carrying out the tenth invention), delivery means such as a pump may be used to add buffer containing an antibody to a column packed with the adsorbent of the ninth invention, to specifically adsorb the antibody onto the adsorbent of the ninth invention, after which a suitable eluent may be added to the column to elute out the antibody. Incidentally, before adding the buffering solution containing the antibody with sugar chains to the column, the column is preferably equilibrated using an appropriate buffering solution to allow isolation of the antibody to a higher purity. Examples for the buffering solution include buffering solutions with inorganic salts as components, such as phosphate buffer. The pH of the buffer is pH 3 to 10 and preferably pH 6 to 9. For elution of the antibody that has been adsorbed onto the adsorbent of the ninth invention, it is sufficient to weaken the interaction between the antibody with sugar chains and the ligand (the Fc-binding protein of the invention), and specifically, this may be by changing the pH with the buffering solution, or using a counter peptide, changing the temperature or changing the salt concentration. A specific example of an eluent for elution of the antibody that has been adsorbed on the adsorbent of the ninth invention is a buffering solution that is more toward the acidic condition than the solution used for adsorption of the antibody onto the adsorbent of the ninth invention. Examples of types of buffering solutions include citrate buffer, glycine hydrochloride buffer and acetate buffer, having buffer capacity at the acidic condition. The pH of the buffering solution may be set within a range that does not impair the function of the antibody, and it is preferably pH 2.5 to 6.0, more preferably pH 3.0 to 5.0 and even more preferably pH 3.3 to 4.0.

2. Improved Recombinant FcγRIIa of the Invention

The improved recombinant FcγRIIa of the invention will now be described.

The improved recombinant FcγRIIa of the first invention is (a) the improved recombinant FcγRIIa comprising at least the amino acid residues from position 29 to position 201 of the amino acid sequence set forth in SEQ ID NO: 88, wherein at least one of the substitutions (7) to (12) are included in the amino acid residues from position 29 to position 201, or (b) the improved recombinant FcγRIIa consisting of an amino acid sequence of the above (a) in which one or more amino acid residues in a region other than positions substituted by the substitutions (7) to (12) have been deleted, substituted or added.

The amino acid sequence set forth in SEQ ID NO: 88 will now be explained. The amino acid sequence set forth in SEQ ID NO: 88 is the amino acid sequence of a recombinant protein (recombinant FcγRIIa) derived from the extracellular domain of human FcγRIIa (SEQ ID NO: 90, UniProt No. P12318-1). The amino acid sequence from the methionine at position 1 to alanine at position 26 at the N-terminal end of SEQ ID NO: 88 is a signal sequence (MalE signal sequence) for secretory expression into the periplasm of E. coli, the amino acid sequence from methionine at position 27 to glycine at position 28 is a linker sequence, the amino acid sequence from glutamine at position 29 to glutamine at position 201 is a sequence derived from the amino acid sequence of the extracellular domain of human FcγRIIa (SEQ ID NO: 90) (glutamine at position 34 to glutamine at position 206 at the N-terminal end of the amino acid sequence set forth in SEQ ID NO: 90), the amino acid sequence from glycine at position 202 to glycine at position 203 is a linker sequence, and the amino acid sequence from histidine at position 204 to histidine at position 209 is a polyhistidine sequence.

Incidentally, the amino acid sequence from glutamine at position 29 to glutamine at position 201 of the amino acid sequence set forth in SEQ ID NO: 88, and the amino acid sequence from threonine at position 29 to glutamine at position 201 of the amino acid sequence set forth in SEQ ID NO: 1 are highly homologous, with a difference of only 12 amino acid residues. The specific differing locations are shown in FIG. 4. The amino acid sequences of human FcγRIIa and human FcγRIIb are highly conserved.

Substitutions (7) to (12) have the effect of increasing productivity (expression level) by transformants in the production of improved recombinant FcγRIIa according to the first invention. Productivity of the improved recombinant FcγRIIa according to the first invention is therefore higher productivity than recombinant FcγRIIa consisting of the amino acid sequence set forth in SEQ ID NO: 88. In order to further increase productivity of improved recombinant FcγRIIa according to the first invention by transformants, it preferably has multiple substitutions among substitutions (7) to (12), and more preferably it has all of them.

Substitutions (7) to (12) also have the effect of increasing the thermal stability of the improved recombinant FcγRIIa according to the first invention. Thermal stability of the improved recombinant FcγRIIa according to the first invention is therefore higher thermal stability than recombinant FcγRIIa consisting of the amino acid sequence set forth in SEQ ID NO: 88. In order to further increase the thermal stability of improved recombinant FcγRIIa according to the first invention, it preferably has multiple substitutions among substitutions (7) to (12), and more preferably it has all of them.

A preferred example of the improved recombinant FcγRIIa according to the first invention is improved FcγRIIa according to the second invention, i.e. (v): improved recombinant FcγRIIa comprising at least the amino acid residues from position 29 to position 201 of the amino acid sequence set forth in SEQ ID NO: 88, wherein at least the substitution (7) is included in the amino acid residues from position 29 to position 201, or (vi): improved recombinant FcγRIIa consisting of an amino acid sequence of the improved recombinant FcγRIIa of the above (v) in which one or more amino acid residues in a region other than the position substituted by the substitution (7) have been deleted, substituted or added, and having affinity for IgG.

Another preferred example of the improved recombinant FcγRIIa of the first invention is improved recombinant FcγRIIa according to the third invention, i.e. improved recombinant FcγRIIa comprising at least the amino acid residues from position 29 to position 201 of the amino acid sequence set forth in SEQ ID NO: 89, which is improved recombinant FcγRIIa including substitution (7), substitution (8), substitution (9), substitution (10), substitution (11) and substitution (12).

The improved recombinant FcγRIIa according to the first to third inventions preferably has a signal sequence at the N-terminal end, that promotes soluble expression in an expression host. When the host is E. coli, for example, it preferably has a signal sequence for secretory expression into the periplasm of E. coli. The signal sequence for secretory expression into the periplasm of E. coli may be one that is publicly known from the literature on MalE signal sequences (for example, S. H. Yoon et al., Recent Pat. Biotechnol., 4, 23-29, 2010). However, if only an effect of increasing thermal stability by substitutions (7) to (12) is desired, then the improved recombinant FcγRIIa according to the first to third inventions does not need to have a signal sequence at the N-terminal end that promotes soluble expression in the expression host.

As long as affinity for IgG is maintained, the improved recombinant FcγRIIa according to the first to third inventions may have a deletion, substitution or addition of one or more amino acids in a region other than positions substituted by substitutions (7) to (12) (or in other words, additionally, while retaining substitutions (7) to (12)). For example, the portion of the amino acid sequence set forth in SEQ ID NO: 88 corresponding to the MalE signal sequence, which is a signal for secretory expression into the periplasm of E. coli (sometimes also including an adjacent linker sequence), may be substituted by another signal sequence such as PelB, DsbA or TorT (S. H. Yoon et al., Recent Pat. Biotechnol., 4, 23-29, 2010), or the portion corresponding to the MalE signal sequence may be deleted. Alternatively, for example, the portion of the amino acid sequence set forth in SEQ ID NO: 88 corresponding to the polyhistidine sequence (sometimes including an adjacent linker sequence) may be substituted by another sequence (for example, an oligopeptide such as polylysine, polyarginine, polyglutamic acid, polyaspartic acid, or a cysteine tag comprising the amino acid residues from arginine at position 200 to glycine at position 205 of SEQ ID NO: 175), or the portion corresponding to the polyhistidine sequence may be deleted. In addition, the amino acid sequence of a protein with another function such as glutathione S-transferase or maltose-binding protein may be added to the improved recombinant FcγRIIa according to the first to third inventions, to form a fusion protein. The number of amino acid residues that may be deleted, substituted or added in the portion corresponding to the amino acid residues from glutamine at position 29 to glutamine at position 201 of the amino acid sequence set forth in SEQ ID NO: 88 is preferably 1 to 10 and more preferably 1 to 5. The amino acid deletion, substitution or addition may be carried out using a genetic engineering method known to those skilled in the art.

The affinity for IgG of the improved recombinant FcγRIIa according to the invention can be evaluated by Enzyme-linked immunosorbent assay (ELISA) (for example, ELISA method 1 described below), or a surface plasmon resonance method (P. Bruhns et al., Blood, 113, 3716-3725, 2009).

ELISA method 1 will now be described. In ELISA method 1, IgG (product of Kaketsuken) is prepared to a concentration of 10 μg/mL with 50 mM Tris-HCl buffer (pH 8.0), and then added into each well of a 96-well microplate (MaxiSorp, Nunc) at 100 μL/well, and the IgG is immobilized (at 4° C. for 18 hours). After immobilization is complete, the solution in each well is discarded and TBS-B buffer (20 mM Tris-HCl (pH 8.0) containing 137 mM NaCl, 2.68 mM KCl and 0.5% (w/v) bovine serum albumin) is added to each well for blocking (at 30° C. for 2 hours). After rinsing each well with rinsing buffer (20 mM Tris-HCl buffer (pH 7.5) containing 0.05% (w/v) Tween 20 and 150 mM NaCl), sample solution containing the improved recombinant FcγRIIa is added to the wells and reaction with the immobilized IgG is conducted (at 30° C. for 1.5 hours). Upon completion of the reaction, each well is rinsed with rinsing buffer, horseradish peroxidase-labeled anti-His-Tag antibody reagent (product of Bethyl) (diluted with 50 mM Tris-HCl buffer (pH 8.0)) is added to each well, and reaction is conducted at 30° C. for 1.5 hours. After the reaction, each well is rinsed with rinsing buffer, TMB Peroxidase Substrate (product of KPL) is added to each well, and the absorbance at 450 nm is measured.

The fourth to eighth inventions will now be explained. DNA according to the fourth invention can be obtained by a method of modifying cDNAs of human FcγRIIa or other FcγR (such as human FcγRIIb or FcγRIIc) utilizing a DNA amplification method such as Polymerase Chain Reaction (PCR), a method of converting the amino acid sequences of human FcγRIIa or other FcγR (such as FcγRIIb or FcγRIIc) to base sequences, artificially preparing DNA including the base sequences, and using a DNA amplification method for further modifying preparation, or a method of converting the amino acid sequence set forth in SEQ ID NO: 89 to a base sequence and artificially preparing DNA that includes the base sequences. When converting amino acid sequences to base sequences in these methods, it is preferred to take into account the frequency of use of codons by the microorganisms and cells (host) utilized for production of the improved recombinant FcγRIIa according to the first to third inventions. As an example, when the host used is E. coli, the usage frequencies of AGA, AGG, CGG or CGA for arginine (Arg), ATA for isoleucine (Ile), CTA for leucine (Leu), GGA for glycine (Gly) and CCC for proline (Pro) are low, i.e. they are rare codons, and therefore codons other than these codons are preferably selected for the conversion. Incidentally, analysis of codon usage frequency may be made utilizing the Codon Usage Database http://www.kazusa.or.jp/codon/, access date: Jun. 21, 2016) at the home page of the Kazusa DNA Research Institute, for example.

When preparing DNA for the fourth invention using a DNA amplification method, a mutagenesis method using an error-prone PCR method may be employed. The reaction conditions for the error-prone PCR method are not particularly restricted so long as they are conditions allowing introduction of the desired mutation into the DNA, and for example, PCR may be carried out in which non-homogeneous concentrations of the four different deoxynucleotides (dATP/dTTP/dCTP/dGTP) as substrates are prepared, and $MnCl_2$ is added to the PCR reaction mixture at concentrations from 0.01 to 10 mM and preferably 0.1 to 1 mM.

A specific example of DNA for the fourth invention is DNA consisting of the base sequence set forth in SEQ ID NO: 91 encoding the amino acid sequence set forth in SEQ ID NO: 89.

For transformation of a host using DNA according to the fourth invention, transformation may be carried out using the actual DNA of the invention, but from the viewpoint of allowing stable transformation to be carried out, preferably the DNA of the fourth invention is inserted at an appropriate position in a vector based on a bacteriophage, cosmid or plasmid commonly used for transformation of prokaryotic cells or eukaryotic cells to prepare a recombinant vector according to the fifth invention, which is used for transformation. The "appropriate location" is a location where the replicating function of the recombinant vector, the desired antibiotic marker and the transfer-associated regions are not destroyed. When the DNA of the fourth invention is inserted into the vector, preferably it is inserted into the vector in a state linked to functional DNA such as a promoter necessary for expression.

The vector used for the fifth invention is not particularly restricted so long as it is stably present and can replicate in the host, and when E. coli is used as the host, it may be a pET vector, pUC vector, pTrc vector, pCDF vector or pBBR vector, for example. Promoters to be used for the invention include, for E. coli as the host for example, trp promoter, tac promoter, trc promoter, lac promoter, T7 promoter, recA promoter and lpp promoter, as well as the λ phage λPL promoter and λPR promoter.

Transformants according to the sixth invention or seventh invention may be obtained by transforming the host using a recombinant vector according to the fifth invention. A transformant according to the sixth invention or seventh invention includes a recombinant vector according to the fifth invention.

There are no particular restrictions on the host to be used for the sixth invention, but E. coli (a mode of the seventh invention) is preferred from the viewpoint of facilitating experimentation for genetic engineering. Transformation of a host using a recombinant vector of the fourth invention may be carried out by any method commonly used by those skilled in the art, and for example, when E. coli (E. coli JM109, E. coli BL21(DE3), E. coli NiCo21(DE3), E. coli W3110 or the like) is selected as the host, a method described in the published literature may be used (for example, Molecular Cloning, Cold Spring Harbor Laboratory, 256, 1992). A recombinant vector according to fifth invention may be extracted from the transformant of the sixth invention or seventh invention using an appropriate extraction method or commercially available kit. When the host is E. coli, for example, an alkaline extraction method or a commercially available extraction kit such as a QIAprep Spin Miniprep kit (trade name of Qiagen Inc.) may be used.

The eighth invention is a method of producing improved recombinant FcγRIIa according to the first to third inventions using a transformant according to the sixth invention or seventh invention, and it includes two steps of: culturing the transformant to produce improved recombinant FcγRIIa according to the first to third inventions (hereunder referred to as the "first step"); and collecting the improved recombinant FcγRIIa according to the first to third inventions from the obtained cultured product (hereunder referred to as the "second step"). Throughout the present specification, the term "cultured product" includes the cultured transformants themselves and their cellular secretion products, as well as the culture medium used for culturing.

In the first step of the eighth invention, culturing of the transformant may be carried out in medium suited for its culturing. For example, when E. coli is used as the host (that is, the mode of the seventh invention), it is preferred to use Luria-Bertani (LB) culture medium supplemented with the necessary nutrients. When the recombinant vector of the fifth invention includes an antibiotic resistance gene, the antibiotic corresponding to the gene may be added to the culture medium and the first step carried out to allow selective growth of the transformant, a preferred example being, when the recombinant vector includes a kanamycin resistance gene, addition of kanamycin to the culture medium.

A carbon, nitrogen and inorganic salt source, as well as appropriate nutrients, are added to the culture medium, but a reagent such as glycine may also be added to promote secretion of protein from the transformant of the sixth invention or seventh invention into the culture solution. When the host is E. coli (a transformant of the seventh invention is used), the added glycine concentration may be in a range that does not affect growth, and it is preferably no greater than 10% (w/v) and more preferably 0.1% (w/v) to 2% (w/v), with respect to the culture medium. The culturing temperature may be a temperature commonly known for the host used, and when the host is E. coli, for example, it is 10° C. to 40° C. and preferably 20° C. to 37° C., being appropriately set in consideration of the desired amount of production according to the first to third inventions. The medium pH may be any pH range commonly known for the host used, and when the host is E. coli (a transformant of the seventh invention is used), for example, it is in the range of pH 6.8 to pH 7.4 and preferably about pH 7.0, being appropriately set in consideration of the desired amount of production according to the first to third inventions.

When an inducible promoter has been introduced into a recombinant vector of the fifth invention, an inducer may be added to the culture medium to induce expression under conditions allowing satisfactory production by the first to third inventions. An example of a preferred inducer is isopropyl-β-D-thiogalactopyranoside (IPTG), added to a concentration in the range of 0.005 to 1.0 mM and preferably the range of 0.01 to 0.5 mM. Expression induction by IPTG addition may be carried out under conditions commonly known for the host used.

In the second step of the eighth invention, the improved recombinant FcγRIIa according to the first to third inventions is collected from the cultured product obtained by the first step by a commonly known collection method. For example, when the improved recombinant FcγRIIa according to the first to third inventions is produced by secretion in the culture solution, the cells may be separated by a centrifugal separation procedure and the improved recombinant FcγRIIa according to the first to third inventions may be collected from the obtained culture supernatant, or when it is expressed intracellularly (including in the periplasm for prokaryotes), the cells may be collected by a centrifugal separation procedure, after which an enzymatic treatment agent or surfactant may be added to disrupt the cells, and the product collected from the cell disruptate.

The improved recombinant FcγRIIa according to the first to third inventions may be collected from the cultured product of the host according to the eighth invention, in the manner described above. When the collected improved recombinant FcγRIIa according to the first to third inventions is to be further increased in purity, a commonly known purification method may be used. Isolation and purification using liquid chromatography may be mentioned, in which case it is preferred to use ion-exchange chromatography, hydrophobic interaction chromatography, gel filtration chromatography or affinity chromatography, and more preferably these chromatography methods are combined for purification.

An adsorbent according to the ninth invention can be produced by immobilizing the improved FcγRIIa of the first to third inventions to an insoluble support. There are no particular restrictions on the insoluble support, and examples include supports where the starting material is a polysaccharide such as agarose, alginate, carrageenan, chitin, cellulose, dextrin, dextran or starch, supports where the starting material is a synthetic polymer such as polyvinyl alcohol polymethacrylate, poly(2-hydroxyethyl methacrylate) or polyurethane, and supports where the starting material is a ceramic such as silica. Preferred among these as the insoluble support are supports where the starting material is a polysaccharide and supports where the starting material is a synthetic polymer. Examples of preferred supports include hydroxyl-introduced polymethacrylate gels such as TOYOPEARL (by Tosoh Corp.), agarose gels such as Sepharose (by GE Healthcare), and cellulose gels such as CELLUFINE (by JNC). There are no particular restrictions on the form of the insoluble support, and it may be granular, non-granular, porous or non-porous.

For immobilization of the improved FcγRIIa of the first to third inventions on the insoluble support, the insoluble support may be provided with active groups such as N-hydroxysuccinic acid imide (NHS) activated ester groups, epoxy, carboxyl, maleimide, haloacetyl, tresyl, formyl and haloacetamide groups, immobilization being accomplished by covalent bonding between the human Fc-binding protein and insoluble support through the active groups. The support with the active groups may be a commercially available support used as is, or it may be prepared by introducing active groups onto the support surface under appropriate reaction conditions. Examples of commercially available supports with active groups include TOYOPEARL AF-Epoxy-650M and TOYOPEARL AF-Tresyl-650M (both by Tosoh Corp.), HiTrap NHS-activated HP Columns, NHS-activated Sepharose 4 Fast Flow and Epoxy-activated Sepharose 6B (all by GE Healthcare), and SulfoLink Coupling Resin (by Thermo Scientific).

Examples of methods for introducing active groups onto the support surface, on the other hand, include methods in which one site of a compound with two or more active sites is reacted with hydroxyl, epoxy, carboxyl and amino groups present on the support surface. Compounds having epoxy groups introduced onto hydroxyl or amino groups on the support surface, as examples of such compounds, include epichlorhydrin, ethanediol diglycidyl ether, butanediol diglycidyl ether and hexanediol diglycidyl ether. Compounds that introduce carboxyl groups onto the support surface after epoxy groups have been introduced onto the support surface by the compound, include 2-mercaptoacetic acid, 3-mercaptopropionic acid, 4-mercaptobutyric acid, 6-mercaptobutyric acid, glycine, 3-aminopropionic acid, 4-aminobutyric acid and 6-aminohexanoic acid.

Examples of compounds that introduce maleimide groups onto hydroxyl or epoxy, carboxyl or amino groups present on the support surface include N-(ε-maleimidecaproic acid) hydrazide, N-(ε-maleimidepropionic acid)hydrazide, 4-(4-N-maleimidephenyl)acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimide)phenylisocyanato, 2-maleimideacetic acid, 3-maleimidepropionic acid, 4-maleimidebutyric acid, 6-maleimidehexanoic acid, (N-[α-maleimideacetoxy])succinimide ester, (m-maleimidebenzoyl)N-hydroxysuccinimide ester, (succinimidyl-4-[maleimidemethyl])cyclohexane-1-carbonyl-[6-aminohexanoic acid], (succinimidyl-4-[maleimidemethyl]) cyclohexane-1-carboxylic acid, (p-maleimidebenzoyl)N-hydroxysuccinimide ester and (m-maleimidebenzoyl)N-hydroxysuccinimide ester.

Examples of compounds that introduce haloacetyl groups onto hydroxyl or amino groups present on the support surface include chloroacetic acid, bromoacetic acid, iodoacetic acid, chloroacetic acid chloride, bromoacetic acid chloride, bromoacetic acid bromide, chloroacetic anhydride, bromoacetic anhydride, iodoacetic anhydride, 2-(iodoacetamide)acetic acid-N-hydroxysuccinimide ester, 3-(bromoacetamide)propionic acid-N-hydroxysuccinimide ester and 4-(iodoacetyl)aminobenzoic acid-N-hydroxysuccinimide ester. There may also be mentioned methods in which an ω-alkenylalkaneglycidyl ether is reacted with hydroxyl or amino groups present on the support surface, and then the ω-alkenyl site is halogenated with a halogenating agent and activated. Examples of ω-alkenylalkaneglycidyl ethers include allyl glycidyl ether, 3-butenyl glycidyl ether and 4-pentenyl glycidyl ether, and examples of halogenating agents include N-chlorosuccinimide, N-bromosuccinimide and N-iodosuccinimide.

A different example of a method for introducing active groups onto the support surface, is a method in which activated groups are introduced onto the carboxyl groups present on the support surface using a condensation agent and an additive. Examples of condensation agents include 1-ethyl-3-(3-dimethylaminopropyl)carbodiimide (EDC), dicyclohexylcarbodiamide and carbonyldiimidazole. Examples of additives include N-hydroxysuccinic acid imide (NHS), 4-nitrophenol and 1-hydroxybenzotriazole.

Examples for the buffering solution to be used during immobilization of the improved FcγRIIa of the first to third inventions on the insoluble support include acetate buffer, phosphate buffer, MES (2-Morpholinoethanesulfonic acid) buffer, HEPES (4-(2-hydroxyethyl)-1-piperazine-ethane-sulfonic acid) buffer, Tris buffer and borate buffer. The reaction temperature for immobilization may be appropriately set in a temperature range from 5° C. to 50° C., and is preferably in the range of 10° C. to 35° C., from the viewpoint of the reactivity of the active groups and the stability of the Fc-binding protein of the invention.

For isolation of the antibody using the adsorbent of the ninth invention (carrying out the tenth invention), delivery means such as a pump may be used to add buffer containing an antibody to a column packed with the adsorbent of the ninth invention, to specifically adsorb the antibody onto the adsorbent of the ninth invention, after which a suitable eluent may be added to the column to elute out the antibody. Incidentally, before adding the buffering solution containing the antibody with sugar chains to the column, the column is preferably equilibrated using an appropriate buffering solution to allow isolation of the antibody to a higher purity. Examples for the buffering solution include buffering solutions with inorganic salts as components, such as phosphate buffer. The pH of the buffer is pH 3 to 10 and preferably pH 6 to 9. For elution of the antibody that has been adsorbed onto the adsorbent of the ninth invention, it is sufficient to weaken the interaction between the antibody with sugar chains and the ligand (the Fc-binding protein of the invention), and specifically, this may be by changing the pH with the buffering solution, or using a counter peptide, changing the temperature or changing the salt concentration. A specific example of an eluent for elution of the antibody that has been adsorbed on the adsorbent of the ninth invention is a buffering solution that is more toward the acidic condition than the solution used for adsorption of the antibody onto the adsorbent of the ninth invention. Examples of types of buffering solutions include citrate buffer, glycine hydrochloride buffer and acetate buffer, having buffer capacity at the acidic condition. The pH of the buffering solution may be set within a range that does not impair the function of the antibody, and it is preferably pH 2.5 to 6.0, more preferably pH 3.0 to 5.0 and even more preferably pH 3.3 to 4.0.

Advantageous Effects of Invention

The improved recombinant FcγRIIb and improved FcγRIIa of the invention do not require refolding since they are expressed in soluble form by *E. coli* hosts, and at least one effect is exhibited among high productivity and high thermal stability. According to another mode of the invention, a method for producing the improved recombinant FcγRIIb and improved FcγRIIa is provided.

BRIEF DESCRIPTION OF DRAWINGS

FIG. 4 is a table showing the differences between the amino acid sequence from threonine at position 29 to glutamine at position 201 of the amino acid sequence set forth in SEQ ID NO: 1, and the amino acid sequence from glutamine at position 29 to glutamine at position 201 of the amino acid sequence set forth in SEQ ID NO: 88.

EXAMPLES

Figure 1:
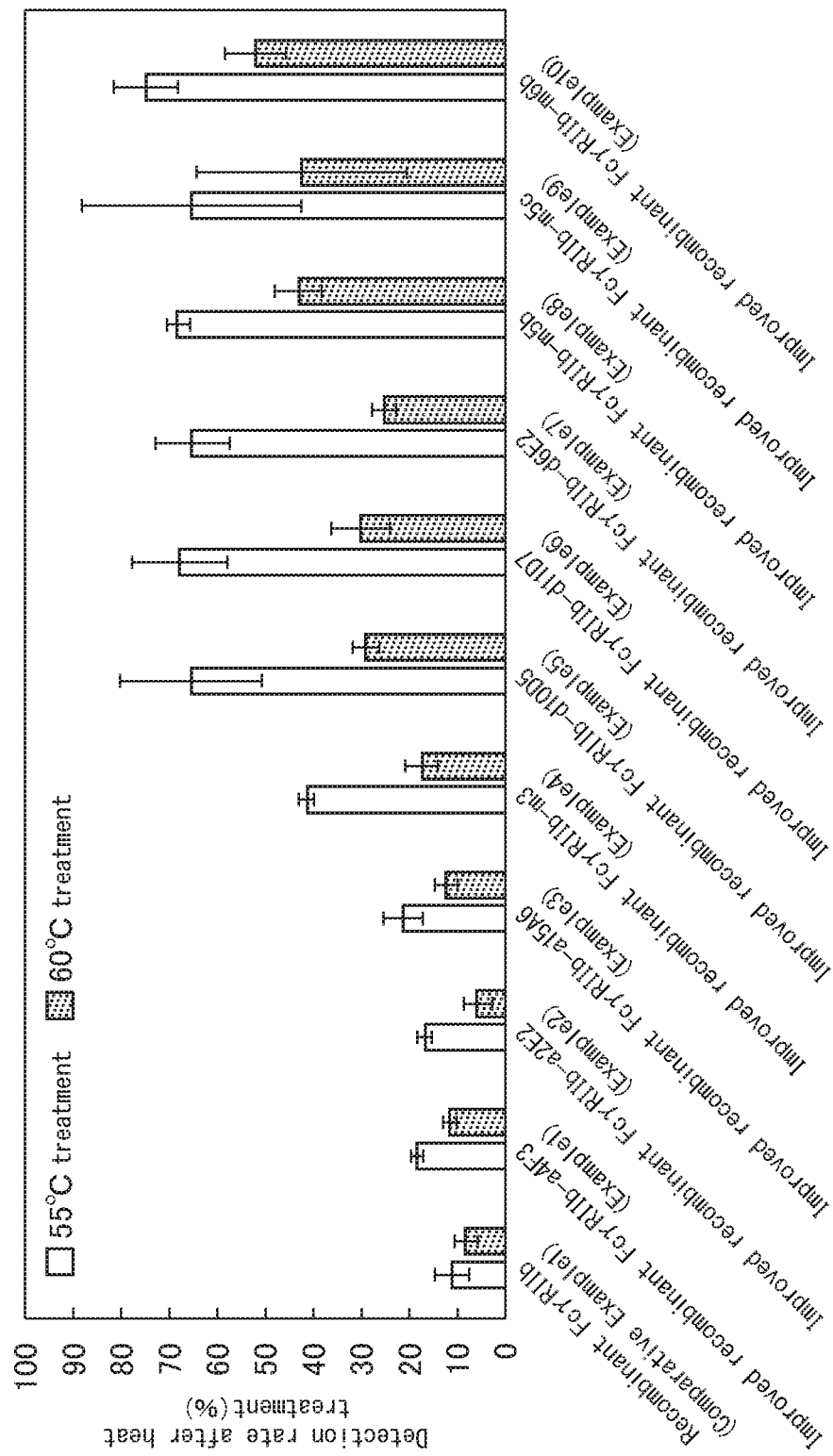
FIG. 1 is a graph showing evaluation of the thermal stability of the improved recombinant FcγRIIb.

Embodiments of the present invention will now be described in detail using examples and comparative examples, with the understanding that these examples serve merely to illustrate modes of the invention and are not intended to restrict the invention in any way.

Example 1 Preparation of Improved Recombinant FcγRIIb-a4F3

(1) Preparation of DNA Including Base Sequence Encoding the Improved Recombinant FcγRIIb-a4F3

DNA including a base sequence (SEQ ID NO: 13) encoding improved recombinant FcγRIIb-a4F3 including substitution (3) (the amino acid sequence set forth in SEQ ID NO: 2) was prepared, as described below ((1-1) to (1-3)), by first converting the amino acid sequence of human FcγRIIb to a base sequence and then preparing DNA including the base sequence, and modifying it by DNA amplification (two stages: PCR and error-prone PCR).

(1-1) Conversion from Amino Acid Sequence of Human FcγRIIb to Base Sequence, and Preparation of DNA Including Base Sequence Based on the amino acid sequence of human FcγRIIb (SEQ ID NO: 12), the codons were converted to *E. coli* codons using the DNA works method (Nucleic Acid Res., 30, ep.43, 2002), to design a base sequence encoding the amino acid sequence of human FcγRIIb set forth in SEQ ID NO: 24.

DNA having a base sequence encoding the amino acid sequence of human FcγRIIb set forth in SEQ ID NO: 24 was prepared by two-stage PCR utilizing 42 different oligonucleotides set forth in SEQ ID NO: 25 to SEQ ID NO: 66.

In the first stage PCR, a reaction mixture with the composition shown in Table 1 was prepared, and then the reaction mixture was heated at 94° C. for 5 minutes, after which 25 cycles of a reaction were repeated, where one cycle consisted of a first step at 94° C. for 30 seconds, a second step at 62° C. for 30 seconds and a third step at 72° C. for 1 minute, and then treatment was carried out at 72° C. for 7 minutes and the mixture was cooled to 4° C. The "DNA mix" in Table 1 is a mixed solution of fixed sampled quantities of the 42 different oligonucleotides set forth in SEQ ID NO: 25 to SEQ ID NO: 66.

TABLE 1

| Composition | Volume |
| --- | --- |
| 10 × Pyrobest buffer II (Takara Bio, Inc.) | 5 μL |
| dNTPs (Takara Bio, Inc.) | 5 μL |
| DNA mix | 1 μL |
| Pyrobest DNA Polymerase (Takara Bio, Inc.) | 0.5 μL |
| H₂O | up to 50 μL |

In the second stage PCR, a reaction mixture with the composition shown in Table 2 was prepared, and then the reaction mixture was heated at 94° C. for 5 minutes, after which 25 cycles of a reaction were repeated, where one cycle consisted of a first step at 94° C. for 30 seconds, a second step at 65° C. for 30 seconds and a third step at 72° C. for 1 minute, and then treatment was carried out at 72° C. for 7 minutes and the mixture was cooled to 4° C.

TABLE 2

| Composition | Volume |
| --- | --- |
| 10 × Pyrobest buffer II (Takara Bio, Inc.) | 5 µL |
| dNTPs (Takara Bio, Inc.) | 5 µL |
| 10 pmol/µL oligonucleotide of SEQ ID NO: 25 | 2 µL |
| 10 pmol/µL oligonucleotide of SEQ ID NO: 66 | 2 µL |
| First stage PCR product | 1 µL |
| Pyrobest DNA Polymerase (Takara Bio, Inc.) | 0.5 µL |
| H$_2$O | up to 50 µL |

The second stage PCR product was electrophoresed using agarose gel, and then the gel portion including the target PCR product was cut out and extracted using a QIAquick Gel extraction kit (product of Qiagen Inc.) for purification (purification by the same method will hereunder be referred to simply as "DNA fragment purification"). The 5'-end of the purified PCR product was phosphorylated (TaKaRa BKL Kit: Takara Bio, Inc.) and linked by ligation to a pUC19 plasmid vector that had been digested with restriction enzyme SmaI, and the vector was used for transformation of E. coli JM109 (Takara Bio, Inc.). The obtained transformants were cultured in LB medium (10 g/L Tryptone, 5 g/L Yeast extract, 5 g/L NaCl) containing added 50 µg/mL ampicillin and a QIAprep Spin Miniprep Kit (Qiagen Inc.) was used for extraction to prepare vector pUC-FcγRIIb.

(1-2) Modification Using DNA Amplification Method (PCR)

PCR was carried out using the vector pUC-FcγRIIb as template DNA and oligonucleotides consisting of the sequences set forth in SEQ ID NO: 67 and SEQ ID NO: 68 as PCR primers. The PCR was carried out by preparing a reaction mixture with the composition shown in Table 3, then heat treating the reaction mixture at 98° C. for 5 minutes, subsequently repeating 30 cycles of a reaction where one cycle consisted of a first step at 98° C. for 10 seconds, a second step at 55° C. for 5 seconds and a third step at 72° C. for 1 minute, and then carrying out treatment at 72° C. for 5 minutes and cooling the mixture to 4° C. The obtained PCR product was designated as rhFcγRIIb-p1.

TABLE 3

| Composition | Volume |
| --- | --- |
| Template DNA | 1 µL |
| 10 pmol/µL PCR primer | 2 µL each |
| 2.5 U/µL PrimeSTAR HS (Takara Bio, Inc.) | 0.25 µL |
| 5 × PrimeSTAR buffer (Takara Bio, Inc.) | 10 µL |
| dNTPs (Takara Bio, Inc.) | 4 µL |
| H$_2$O | up to 50 µL |

After digesting the DNA fragment-purified PCR product rhFcγRIIb-p1 with restriction enzymes NcoI and HindIII, DNA fragment purification was carried out again. The PCR product rhFcγRIIb-p1 that had been digested with restriction enzymes NcoI and HindIII was linked by ligation with pETMalE21 vector that had been previously digested with restriction enzymes NcoI and HindIII (the pETMalE21 vector was prepared by the method reported by Hatayama & Ide (Protein Expr. Purif., 111, 1-8, 2015)), to construct recombinant vector pET-rhFcγRIIb, which was used for transformation of E. coli NiCo21(DE3) (product of New England Biolabs) by the calcium chloride method. The obtained transformant was designated as transformant rhFcγRIIb.

Transformant rhFcγRIIb was cultured in LB medium containing added 50 µg/mL kanamycin, and a QIAprep Spin Miniprep Kit was used for extraction to prepare recombinant vector pET-rhFcγRIIb.

The base sequence of DNA from the restriction enzyme XbaI recognition sequence to the HindIII recognition sequence in recombinant vector pET-rhFcγRIIb is set forth in SEQ ID NO: 69. The region from adenine at position 50 to thymine at position 676 from the 5'-end of SEQ ID NO: 69 encodes recombinant FcγRIIb consisting of the amino acid sequence set forth in SEQ ID NO: 1.

(1-3) Modification Using DNA Amplification Method (Error-Prone PCR Method)

The error-prone PCR method was used to introduce random mutations into DNA encoding the amino acid sequence set forth in SEQ ID NO: 1. The recombinant vector pET-rhFcγRIIb was used as template DNA and oligonucleotides consisting of the sequences set forth in SEQ ID NO: 70 and SEQ ID NO: 71 were used as PCR primers. The error-prone PCR was carried out by preparing a reaction mixture with the composition shown in Table 4, and then heat treating the reaction mixture at 95° C. for 2 minutes, carrying out 30 cycles of reaction where one cycle consisted of a first step at 95° C. for 30 seconds, a second step at 60° C. for 30 seconds and a third step at 72° C. for 90 seconds, and finally conducting heat treatment at 72° C. for 7 minutes. The obtained PCR product (including DNA that included a base sequence encoding the improved recombinant FcγRIIb-a4F3) was designated as EP.

TABLE 4

| Composition | Concentration/Volume |
| --- | --- |
| Template DNA | 0.05 ng/µL |
| Each PCR primer | 0.4 µM |
| MnCl$_2$ | 0.4 mM |
| dATP | 0.2 mM |
| dGTP | 0.2 mM |
| dCTP | 1 mM |
| dTTP | 1 mM |
| Buffer (MgCl$_2$ prepared to 5 mM) | 5 µL |
| GoTaq polymerase (Promega Corp.) | 0.05 U/µL |
| H$_2$O | up to 50 µL |

The DNA fragment-purified PCR product EP was digested with restriction enzymes NcoI and HindIII, and after repeating DNA fragment purification, it was linked by ligation with pETMalE21 vector that had been previously digested with restriction enzymes NcoI and HindIII, and used for transformation of E. coli NiCo21(DE3) by the calcium chloride method. The obtained transformant was used to form colonies in LB agar medium containing 50 µg/mL kanamycin.

(2) Obtaining Transformants with Recombinant Vector Comprising DNA Encoding Improved Recombinant FcγRIIb-a4F3

A transformant (hereunder referred to as "transformant a4F3") transformed by a recombinant vector comprising DNA encoding improved recombinant FcγRIIb-a4F3 (SEQ ID NO: 13) (hereunder referred to as "recombinant vector pET-a4F3") was selected and obtained from among the colony-formed transformants. Specifically, the transformant colonies (approximately 1800) were inoculated into 400 µL of LB medium containing 50 µg/mL kanamycin, and a 96-well deep well plate was used for aerobic shake culturing overnight at 37° C.

After culturing, 20 µL of culture solution was subcultured on 600 µL of LB medium (including 0.05 mM IPTG, 0.3% (w/v) glycine and 50 µg/mL kanamycin), and a 96-well deep well plate was used for aerobic shake culturing for 24 hours at 20° C. After culturing, the culture supernatant obtained by centrifugation was taken as a sample solution.

Next, the amount of soluble improved recombinant FcγRIIb in each 5-fold diluted sample solution was evaluated based on the value measured by ELISA method 1, using 50 mM Tris-HCl buffer (pH 8.0). Transformant a4F3 was selected out and obtained based on the evaluation results of ELISA method 1.

Extraction of recombinant vector pET-a4F3 from transformant a4F3, and confirmation of the base sequences of DNA encoding improved recombinant FcγRIIb-a4F3 and it surrounding region were carried out, respectively, using the recombinant vector extraction and sequence analysis described below.

Recombinant vector extraction: The transformant was cultured (LB medium containing 50 µg/mL kanamycin, overnight at 37° C., aerobic conditions), and a QIAprep Spin Miniprep Kit was used to extract the recombinant vector.

Sequence analysis: DNA encoding improved recombinant FcγRIIb-a4F3 and its surrounding region from the recombinant vector was provided to cycle sequencing reaction using a Big Dye Terminator Cycle Sequencing FS Read Reaction kit (product of PE Applied Biosystems), based on the chain terminator method, and the base sequence was analyzed with a fully automatic DNA sequencer: ABI Prism 3700 DNA analyzer (PE Applied Biosystems). For the analysis, an oligonucleotide consisting of the sequence set forth in SEQ ID NO: 70 or SEQ ID NO: 71 was used as the sequencing primer.

(3) Production of Improved Recombinant FcγRIIb-a4F3

Transformant a4F3 was inoculated into 5 mL of LB medium containing 50 µg/mL kanamycin and precultured by aerobic shake culture overnight at 37° C. After preculturing, 1% (v/v) of the preculturing solution was inoculated into 20 mL of LB medium containing 0.01 mM IPTG and 50 µg/mL kanamycin and aerobically shake cultured at 20° C. for 24 hours, to produce improved recombinant FcγRIIb-a4F3.

A BugBuster Protein extraction kit (Novagen) was used to collect a soluble protein extract containing improved recombinant FcγRIIb-a4F3 from cells harvested by centrifugal separation from the culture solution. The concentration of the improved recombinant FcγRIIb-a4F3 in the soluble protein extract was measured by ELISA method 2 described below. As a result of calculation based on the concentration of the improved recombinant FcγRIIb-a4F3 in the soluble protein extract, the productivity of improved recombinant FcγRIIb-a4F3 per 1 L of culture solution was 1.0±0.1 mg (n=2, collection and measurement of the soluble protein extract conducted twice in series).

ELISA method 2: After preparing anti-FcγRIIB/C antibody (Anti-FcγRIIB/C, Mouse-Mono(190710)) (product of R & D Systems, Catalog No.: BAM18751) to a concentration of 1 µg/mL in 50 mM Tris-HCl buffer (pH 8.0), it was added at 100 µL/well into each well of a 96-well microplate (MaxiSorp, Nunc), and the anti-FcγRIIB/C antibody was immobilized (at 4° C. for 18 hours). After immobilization was complete, the solution in each well was discarded and TBS-B buffer (containing 137 mM NaCl, 2.68 mM KCl and 0.5% (w/v) bovine serum albumin) was added to each well for blocking (at 30° C. for 2 hours). After rinsing each well with rinsing buffer (20 mM Tris-HCl buffer (pH 7.5) containing 0.05% (w/v) Tween 20 and 150 mM NaCl), the prepared soluble protein extract was serially diluted with 50 mM Tris-HCl buffer (pH 8.0), and added to each well for reaction with the immobilized anti-FcγRIIB/C antibody (at 30° C. for 1.5 hours). Upon completion of the reaction, each well was rinsed with rinsing buffer, horseradish peroxidase-labeled anti-His-Tag antibody reagent (product of Bethyl) (diluted with 50 mM Tris-HCl buffer (pH 8.0)) was added to each well, and reaction was conducted at 30° C. for 1.5 hours. After the reaction, each well was rinsed with rinsing buffer, TMB Peroxidase Substrate (product of KPL) was added to each well, and the absorbance at 450 nm was measured. The concentration of the improved recombinant FcγRIIb in the soluble protein extract was determined from the measured absorbance, based on the measurement results for a known concentration of sugar chain-attached recombinant FcγRIIb) (CD32b/c, Human, Recombinant, Carrier-free <FcγRIIB/C>) (prod of R & D Systems, Catalog No.: 1875-CD-050).

Example 2 Preparation of Improved Recombinant FcγRIIb-a2E2

(1) Preparation of DNA Including Base Sequence Encoding Improved Recombinant FcγRIIb-a2E2

DNA including a base sequence (SEQ ID NO: 14) encoding improved recombinant FcγRIIb-a2E2 including substitution (6) (amino acid sequence set forth in SEQ ID NO: 3) was prepared by the same method as described in (1) of Example 1 (the PCR product EP including DNA that included a base sequence encoding improved recombinant FcγRIIb-a2E2).

(2) Obtaining Transformants with Recombinant Vector Comprising DNA Encoding Improved Recombinant FcγRIIb-a2E2

A transformant (hereunder referred to as "transformant a2E2") transformed by a recombinant vector comprising DNA encoding improved recombinant FcγRIIb-a2E2 (SEQ ID NO: 14) (hereunder referred to as "recombinant vector pET-a2E2") was selected and obtained from among the colony-formed transformants described in (1-3) of Example 1. The selection method was the same as described in (2) of Example 1. Extraction of recombinant vector pET-a2E2 from the transformant a2E2 and confirmation of the base sequence of the DNA encoding improved recombinant FcγRIIb-a2E2 and its surrounding region were carried out by the same method as described in (2) of Example 1.

(3) Production of Improved Recombinant FcγRIIb-a2E2

Improved recombinant FcγRIIb-a2E2 was produced using transformant a2E2 by the same method as described in (3) of Example 1. The productivity of improved recombinant FcγRIIb-a2E2 per 1 L of culture solution was 1.3±0.0 mg (n=2).

Example 3 Preparation of Improved Recombinant FcγRIIb-a15A6

(1) Preparation of DNA Including Base Sequence Encoding Improved Recombinant FcγRIIb-a15A6

DNA including a base sequence (SEQ ID NO: 15) encoding improved recombinant FcγRIIb-a15A6 including substitution (1) (amino acid sequence set forth in SEQ ID NO: 4) was prepared by the same method as described in (1) of Example 1 (the PCR product EP including DNA that included a base sequence encoding improved recombinant FcγRIIb-a15A6).

(2) Obtaining Transformants with Recombinant Vector Comprising DNA Encoding Improved Recombinant FcγRIIb-a15A6

A transformant (hereunder referred to as "transformant a15A6") transformed by a recombinant vector comprising DNA encoding improved recombinant FcγRIIb-a15A6 (SEQ ID NO: 15) (hereunder referred to as "recombinant vector pET-a15A6") was selected and obtained from among the colony-formed transformants described in (1-3) of Example 1. The selection method was the same as described in (2) of Example 1. Extraction of recombinant vector pET-a15A6 from the transformant a15A6 and confirmation of the base sequence of the DNA encoding improved recombinant FcγRIIb-a15A6 and its surrounding region were carried out by the same method as described in (2) of Example 1.

(3) Production of Improved Recombinant FcγRIIb-a15A6

Improved recombinant FcγRIIb-a15A6 was produced using transformant a15A6 by the same method as described in (3) of Example 1. The productivity of improved recombinant FcγRIIb-a15A6 per 1 L of culture solution was 1.7±0.0 mg (n=2).

Example 4 Preparation of Improved Recombinant FcγRIIb-m3

(1) Preparation of DNA Including Base Sequence Encoding Improved Recombinant FcγRIIb-m3

DNA including a base sequence (SEQ ID NO: 16) encoding improved recombinant FcγRIIb-m3 including substitution (1), substitution (3) and substitution (6) (the amino acid sequence set forth in SEQ ID NO: 5) was prepared in the following manner.

PCR was carried out using the recombinant vector pET-rhFcγRIIb described in (1-2) of Example 1 as template DNA and oligonucleotides consisting of the sequences set forth in SEQ ID NO: 70 and SEQ ID NO: 72 as PCR primers. PCR was carried out by preparing a reaction mixture with the composition shown in Table 3 and reacting the reaction mixture under the conditions shown in Table 5. The obtained PCR product was designated as m3p1.

TABLE 5

| Reaction temperature (° C.) | Time (sec) | |
|---|---|---|
| 98 | 10 | |
| 50 | 5 | ] 30 cycles |
| 72 | 60 | |

PCR was carried out using the recombinant vector pET-a4F3 described in (2) of Example 1 as template DNA and oligonucleotides consisting of the sequences set forth in SEQ ID NO: 73 and SEQ ID NO: 74 as PCR primers. PCR was carried out by preparing a reaction mixture with the composition shown in Table 3 and reacting the reaction mixture under the conditions shown in Table 5. The obtained PCR product was designated as m3p2.

PCR was carried out using the recombinant vector pET-rhFcγRIIb described in (1-2) of Example 1 as template DNA and oligonucleotides consisting of the sequences set forth in SEQ ID NO: 75 and SEQ ID NO: 71 as PCR primers. PCR was carried out by preparing a reaction mixture with the composition shown in Table 3 and reacting the reaction mixture under the conditions shown in Table 5. The obtained PCR product was designated as m3p3.

PCR was carried out by mixing the DNA fragment-purified PCR products m3p1, m3p2 and m3p3 and then preparing a reaction mixture with the composition shown in Table 6 and reacting the reaction mixture under the conditions shown in Table 7. The obtained PCR product was designated as m3p4.

TABLE 6

| Composition | Volume |
|---|---|
| PCR product | 1 μL each |
| 2.5 U/μL PrimeSTAR HS (Takara Bio, Inc.) | 0.25 μL |
| 5 × PrimeSTAR buffer (Takara Bio, Inc.) | 10 μL |
| 2.5 mM dNTPs | 4 μL |
| H$_2$O | up to 50 μL |

TABLE 7

| Reaction temperature (° C.) | Time (sec) | |
|---|---|---|
| 98 | 10 | |
| 60 | 5 | ] 5 cycles |
| 72 | 60 | |

PCR was carried out using the PCR product m3p4 as template DNA and oligonucleotides consisting of the sequences set forth in SEQ ID NO: 70 and SEQ ID NO: 71 as PCR primers. PCR was carried out by preparing a reaction mixture with the composition shown in Table 3 and reacting the reaction mixture under the conditions shown in Table 5. The obtained PCR product was subjected to DNA fragment purification to obtain DNA including a base sequence (SEQ ID NO: 16) encoding the improved recombinant FcγRIIb-m3.

(2) Preparation of Recombinant Vector Comprising DNA Encoding Improved Recombinant FcγRIIb-m3 and Transformant Comprising it After digesting DNA including a base sequence encoding the improved recombinant FcγRIIb-m3 with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m3"). The recombinant vector pET-m3 was used to transform *E. coli* NiCo21(DE3) by the calcium chloride method. The obtained transformant was designated as transformant m3.

Extraction of recombinant vector pET-m3 from the transformant m3 and confirmation of the base sequence of the DNA encoding improved recombinant FcγRIIb-m3 and its surrounding region were carried out by the same method as described in (2) of Example 1.

(3) Production of Improved Recombinant FcγRIIb-m3

Improved recombinant FcγRIIb-m3 was produced using transformant m3 by the same method as described in (3) of Example 1. The productivity of improved recombinant FcγRIIb-m3 per 1 L of culture solution was 2.3±0.2 mg (n=2).

Example 5 Preparation of Improved Recombinant FcγRIIb-d10D5

(1) Preparation of DNA Including Base Sequence Encoding Improved Recombinant FcγRIIb-d10D5

DNA including a base sequence (SEQ ID NO: 18) encoding improved recombinant FcγRIIb-d10D5 including substitution (1), substitution (3), substitution (5) and substitution (6) (the amino acid sequence set forth in SEQ ID NO: 6) was prepared by modification using a DNA amplification method (two stages: PCR and error-prone PCR) based on DNA encoding improved recombinant FcγRIIb-m3 as described below ((1-1) to (1-2)).

(1-1) Modification Using DNA Amplification Method (PCR)

The region of DNA encoding a portion of the amino acid sequence of improved recombinant FcγRIIb-m3 (from serine at position 107 to proline at position 109 from the N-terminal end of the amino acid sequence set forth in SEQ ID NO: 5) was modified to provide a restriction enzyme BamHI recognition sequence.

PCR was carried out using the recombinant vector pET-m3 described in Example 4 as template DNA and oligonucleotides consisting of the sequences set forth in SEQ ID NO: 70 and SEQ ID NO: 76 as PCR primers. PCR was carried out by preparing a reaction mixture with the composition shown in Table 3 and reacting the reaction mixture under the conditions shown in Table 5. The obtained PCR product was designated as m3(B)p1.

PCR was carried out using the recombinant vector pET-m3 described in Example 4 as template DNA and oligonucleotides consisting of the sequences set forth in SEQ ID NO: 77 and SEQ ID NO: 71 as PCR primers. PCR was carried out by preparing a reaction mixture with the composition shown in Table 3 and reacting the reaction mixture under the conditions shown in Table 5. The obtained PCR product was designated as m3(B)p2.

PCR was carried out by mixing the DNA fragment-purified PCR products m3(B)p1 and m3(B)p2 and then preparing a reaction mixture with the composition shown in Table 6 and reacting the reaction mixture under the conditions shown in Table 7. The obtained PCR product was designated as m3(B)p3.

PCR was carried out using the PCR product m3(B)p3 as template DNA and oligonucleotides consisting of the sequences set forth in SEQ ID NO: 70 and SEQ ID NO: 71 as PCR primers. PCR was carried out by preparing a reaction mixture with the composition shown in Table 3 and reacting the reaction mixture under the conditions shown in Table 5.

The obtained PCR product was subjected to DNA fragment purification to obtain DNA having the restriction enzyme BamHI recognition sequence and including a base sequence (SEQ ID NO: 17) encoding the same amino acid sequence as improved recombinant FcγRIIb-m3 described in Example 4. After digesting this DNA with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m3(B)"). The recombinant vector pET-m3(B) was used to transform *E. coli* NiCo21(DE3) by the calcium chloride method. The obtained transformant was designated as transformant m3(B).

Extraction of recombinant vector pET-m3(B) from the transformant m3(B) and confirmation of the base sequence of the DNA encoding improved recombinant FcγRIIb-m3 and its surrounding region were carried out by the same method as described in (2) of Example 1.

(1-2) Modification Using DNA Amplification Method (Error-Prone PCR)

The error-prone PCR method was used to introduce random mutations into DNA encoding the amino acid sequence of improved recombinant FcγRIIb-m3 (SEQ ID NO: 17). The recombinant vector pET-m3(B) was used as template DNA and oligonucleotides consisting of the sequences set forth in SEQ ID NO: 70 and SEQ ID NO: 71 were used as PCR primers. The error-prone PCR was carried out by preparing a reaction mixture with the composition shown in Table 4, and then heat treating the reaction mixture at 95° C. for 2 minutes, carrying out 30 cycles of reaction where one cycle consisted of a first step at 95° C. for 30 seconds, a second step at 50° C. for 30 seconds and a third step at 72° C. for 90 seconds, and finally conducting heat treatment at 72° C. for 7 minutes. The obtained PCR product (also including DNA that included a base sequence encoding the improved recombinant FcγRIIb-d10D5) was designated as EPm3(B).

The DNA fragment-purified PCR product EPm3(B) was digested with restriction enzymes NcaI and BamHI, and after repeating DNA fragment purification, it was linked by ligation with PET-m3(B) vector that had been previously digested with restriction enzymes NcoI and BamHI, and used for transformation of *E. coli* NiCo21(DE3) by the calcium chloride method. The obtained transformant was used to form colonies in LB agar medium containing 50 μg/mL kanamycin.

(2) Obtaining Transformants with Recombinant Vector Comprising DNA Encoding Improved Recombinant FcγRIIb-d10D5

A transformant (hereunder referred to as "transformant d10D5") transformed by a recombinant vector comprising DNA encoding improved recombinant FcγRIIb-d10D5 (SEQ ID NO: 18) (hereunder referred to as "recombinant vector pET-d10D5") was selected and obtained from among the colony-formed transformants. Specifically, the transformant colonies (approximately 1600) were inoculated into 400 μL of LB medium containing 50 μg/mL kanamycin, and a 96-well deep well plate was used for aerobic shake culturing overnight at 37° C. After culturing, 20 μL of culture solution was subcultured on 600 μL of LB medium (including 0.05 mM IPTG, 0.3% (w/v) glycine and 50 μg/mL kanamycin), and a 96-well deep well plate was used for aerobic shake culturing for 24 hours at 20° C. After culturing, the culture supernatant obtained by centrifugation was taken as a sample solution. Next, the amount of soluble improved recombinant FcγRIIb in each 5-fold diluted sample solution was evaluated based on the value measured by ELISA method 1, using 50 mM Tris-HCl buffer (pH 8.0). Transformant d10D5 was selected out and obtained based on the evaluation results of ELISA method 1. Extraction of recombinant vector pET-d10D5 from the transformant d10D5 and confirmation of the base sequence of the DNA encoding improved recombinant FcγRIIb-d10D5 and its surrounding region were carried out by the same method as described in (2) of Example 1.

(3) Production of Improved Recombinant FcγRIIb-d10D5

Improved recombinant FcγRIIb-d10D5 was produced using transformant d10D5 by the same method as described in (3) of Example 1. The productivity of improved recombinant FcγRIIb-d10D5 per 1 L of culture solution was 2.5±0.1 mg (n=2).

Example 6 Preparation of Improved Recombinant FcγRIIb-d11D7

(1) Preparation of DNA Including Base Sequence Encoding Improved Recombinant FcγRIIb-d11D7

DNA including a base sequence (SEQ ID NO: 19) encoding improved recombinant FcγRIIb-d11D7 including substitution (1), substitution (3), substitution (4) and substitution (6) (the amino acid sequence set forth in SEQ ID NO: 7) was prepared by the same method as described in (1) of Example 5 (the PCR product EPm3(B) including DNA that included a base sequence encoding improved recombinant FcγRIIb-d11D7).

(2) Obtaining Transformants with Recombinant Vector Comprising DNA Encoding Improved Recombinant FcγRIIb-d11D7

A transformant (hereunder referred to as "transformant d11D7") transformed by a recombinant vector comprising DNA encoding improved recombinant FcγRIIb-d11D7 (SEQ ID NO: 19) (hereunder referred to as "recombinant vector pET-d11D7") was selected and obtained from among the colony-formed transformants described in (1-2) of Example 5. The selection method was the same as described in (2) of Example 5. Extraction of recombinant vector pET-d11D7 from the transformant d11D7 and confirmation of the base sequence of the DNA encoding improved recombinant FcγRIIb-d11D7 and its surrounding region were carried out by the same method as described in (2) of Example 1.

(3) Production of Improved Recombinant FcγRIIb-d11D7

Improved recombinant FcγRIIb-d11D7 was produced using transformant d11D7 by the same method as described in (3) of Example 1. The productivity of improved recombinant FcγRIIb-d11D7 per 1 L of culture solution was 3.0±0.3 mg (n=2).

Example 7 Preparation of Improved Recombinant FcγRIIb-d6E2

(1) Preparation of DNA Including Base Sequence Encoding Improved Recombinant FcγRIIb-d6E2

DNA including a base sequence (SEQ ID NO: 20) encoding improved recombinant FcγRIIb-d6E2 including substitution (1), substitution (2), substitution (3) and substitution (6) (the amino acid sequence set forth in SEQ ID NO: 8) was prepared by the same method as described in (1) of Example 5 (the PCR product EPm3(B) including DNA that included a base sequence encoding improved recombinant FcγRIIb-d6E2).

(2) Obtaining Transformants with Recombinant Vector Comprising DNA Encoding Improved Recombinant FcγRIIb-d6E2

A transformant (hereunder referred to as "transformant d6E2") transformed by a recombinant vector comprising DNA encoding improved recombinant FcγRIIb-d6E2 (SEQ ID NO: 20) (hereunder referred to as "recombinant vector pET-d6E2") was selected and obtained from among the colony-formed transformants described in (1-2) of Example 5. The selection method was the same as described in (2) of Example 5. Extraction of recombinant vector pET-d6E2 from the transformant d6E2 and confirmation of the base sequence of the DNA encoding improved recombinant FcγRIIb-d6E2 and its surrounding region were carried out by the same method as described in (2) of Example 1.

(3) Production of Improved Recombinant FcγRIIb-d6E2

Improved recombinant FcγRIIb-d6E2 was produced using transformant d6E2 by the same method as described in (3) of Example 1. The productivity of improved recombinant FcγRIIb-d6E2 per 1 L of culture solution was 3.4±0.0 mg (n=2).

Example 8 Preparation of Improved Recombinant FcγRIIb-m5b (1) Preparation of DNA Including Base Sequence Encoding Improved Recombinant FcγRIIb-m5b DNA including a base sequence (SEQ ID NO: 21) encoding improved recombinant FcγRIIb-m5b including substitution (1), substitution (2), substitution (3), substitution (5) and substitution (6) (the amino acid sequence set forth in SEQ ID NO: 9) was prepared in the following manner.

PCR was carried out using the recombinant vector pET-d10D5 described in Example 5 as template DNA and oligonucleotides consisting of the sequences set forth in SEQ ID NO: 70 and SEQ ID NO: 78 as PCR primers. PCR was carried out by preparing a reaction mixture with the composition shown in Table 3 and reacting the reaction mixture under the conditions shown in Table 5. The obtained PCR product was designated as m5bp 1.

PCR was carried out using the recombinant vector pET-d10D5 described in Example 5 as template DNA and oligonucleotides consisting of the sequences set forth in SEQ ID NO: 79 and SEQ ID NO: 71 as PCR primers. PCR was carried out by preparing a reaction mixture with the composition shown in Table 3 and reacting the reaction mixture under the conditions shown in Table 5. The obtained PCR product was designated as m5bp2.

PCR was carried out by mixing the DNA fragment-purified PCR products m5bp1 and m5bp2 and then preparing a reaction mixture with the composition shown in Table 6 and reacting the reaction mixture under the conditions shown in Table 7. The obtained PCR product was designated as m5bp3.

PCR was carried out using the PCR product m5bp3 as template DNA and oligonucleotides consisting of the sequences set forth in SEQ ID NO: 70 and SEQ ID NO: 71 as PCR primers. PCR was carried out by preparing a reaction mixture with the composition shown in Table 3 and reacting the reaction mixture under the conditions shown in Table 5. The obtained PCR product was subjected to DNA fragment purification to obtain DNA including a base sequence encoding the improved recombinant FcγRIIb-m5b.

(2) Preparation of Recombinant Vector Comprising DNA Encoding Improved Recombinant FcγRIIb-m5b and Transformant Comprising it After digesting DNA including a base sequence encoding the improved recombinant FcγRIIb-m5b with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m5b"). The recombinant vector pET-m5b was used to transform *E. coli* NiCo21(DE3) by the calcium chloride method. The obtained transformant was designated as transformant m5b.

Extraction of recombinant vector pET-m5b from the transformant m5b and confirmation of the base sequence of the DNA encoding improved recombinant FcγRIIb-m5b and its surrounding region were carried out by the same method as described in (2) of Example 1.

(3) Production of Improved Recombinant FcγRIIb-m5b

Improved recombinant FcγRIIb-m5b was produced using transformant m5b by the same method as described in (3) of Example 1. The productivity of improved recombinant FcγRIIb-m5b per 1 L of culture solution was 3.0±0.9 mg (n=2).

Example 9 Preparation of Improved Recombinant FcγRIIb-m5c (1) Preparation of DNA Including Base Sequence Encoding Improved Recombinant FcγRIIb-m5c DNA including a base sequence (SEQ ID NO: 22) encoding improved recombinant FcγRIIb-m5c including substitution (1), substitution (3), substitution (4), substitution (5) and substitution (6) (the amino acid sequence set forth in SEQ ID NO: 10) was prepared in the following manner.

PCR was carried out using the recombinant vector pET-m3(B) described in (1-1) of Example 5 as template DNA and oligonucleotides consisting of the sequences set forth in SEQ ID NO: 70 and SEQ ID NO: 80 as PCR primers. PCR was carried out by preparing a reaction mixture with the composition shown in Table 3 and reacting the reaction mixture under the conditions shown in Table 5. The obtained PCR product was designated as m5cp1.

PCR was carried out using the recombinant vector pET-m3(B) described in (1-1) of Example 5 as template DNA and oligonucleotides consisting of the sequences set forth in SEQ ID NO: 81 and SEQ ID NO: 71 as PCR primers. PCR was carried out by preparing a reaction mixture with the composition shown in Table 3 and reacting the reaction mixture under the conditions shown in Table 5. The obtained PCR product was designated as m5cp2.

PCR was carried out by mixing the DNA fragment-purified PCR products m5cp1 and m5cp2 and then preparing a reaction mixture with the composition shown in Table 6 and reacting the reaction mixture under the conditions shown in Table 7. The obtained PCR product was designated as m5cp3.

PCR was carried out using the PCR product m5cp3 as template DNA and oligonucleotides consisting of the sequences set forth in SEQ ID NO: 70 and SEQ ID NO: 71 as PCR primers. PCR was carried out by preparing a reaction mixture with the composition shown in Table 3 and reacting the reaction mixture under the conditions shown in Table 5. The obtained PCR product was subjected to DNA fragment purification to obtain DNA including a base sequence encoding the improved recombinant FcγRIIb-m5c.

(2) Preparation of Recombinant Vector Comprising DNA Encoding Improved Recombinant FcγRIIb-m5c and Transformant Comprising it After digesting DNA including a base sequence encoding the improved recombinant FcγRIIb-m5c with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m5c"). The recombinant vector pET-m5c was used to transform *E. coli* NiCo21(DE3) by the calcium chloride method. The obtained transformant was designated as transformant m5c.

Extraction of recombinant vector pET-m5c from the transformant m5c and confirmation of the sequence of the DNA encoding improved recombinant FcγRIIb-m5c and its surrounding region were carried out by the same method as described in (2) of Example 1.

(3) Production of Improved Recombinant FcγRIIb-m5c

Improved recombinant FcγRIIb-m5c was produced using transformant m5c by the same method as described in (3) of Example 1. The productivity of improved recombinant FcγRIIb-m5c per 1 L of culture solution was 3.5±0.6 mg (n=2).

Example 10 Preparation of Improved Recombinant FcγRIIb-m6b (1) Preparation of DNA Including Base Sequence Encoding Improved Recombinant FcγRIIb-m6b DNA including a base sequence (SEQ ID NO: 23) encoding improved recombinant FcγRIIb-m6b including substitution (1), substitution (2), substitution (3), substitution (4), substitution (5) and substitution (6) (the amino acid sequence set forth in SEQ ID NO: 11) was prepared by the following method.

PCR was carried out using DNA including a base sequence encoding the improved recombinant FcγRIIb-m5c described in (1) of Example 9 as template DNA, and oligonucleotides consisting of the sequences set forth in SEQ ID NO: 70 and SEQ ID NO: 78 as PCR primers. PCR was carried out by preparing a reaction mixture with the composition shown in Table 3 and reacting the reaction mixture under the conditions shown in Table 5. The obtained PCR product was designated as m6bp 1.

PCR was carried out using DNA including a base sequence encoding the improved recombinant FcγRIIb-m5c described in (1) of Example 9 as template DNA, and oligonucleotides consisting of the sequences set forth in SEQ ID NO: 79 and SEQ ID NO: 71 as PCR primers. PCR was carried out by preparing a reaction mixture with the composition shown in Table 3 and reacting the reaction mixture under the conditions shown in Table 5. The obtained PCR product was designated as m6bp2.

PCR was carried out by mixing the DNA fragment-purified PCR products m6bp1 and m6bp2 and then preparing a reaction mixture with the composition shown in Table 6 and reacting the reaction mixture under the conditions shown in Table 7. The obtained PCR product was designated as m6bp3.

PCR was carried out using the PCR product m6bp3 as template DNA and oligonucleotides consisting of the sequences set forth in SEQ ID NO: 70 and SEQ ID NO: 71 as PCR primers. PCR was carried out by preparing a reaction mixture with the composition shown in Table 3 and reacting the reaction mixture under the conditions shown in Table 5. The obtained PCR product was subjected to DNA fragment purification to obtain DNA including a base sequence encoding the improved recombinant FcγRIIb-m6b.

(2) Preparation of Recombinant Vector Comprising DNA Encoding Improved Recombinant FcγRIIb-m6b and Transformant Comprising it After digesting DNA including a base sequence encoding the improved recombinant FcγRIIb-m6b with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m6b"). The recombinant vector pET-m6b was used to transform *E. coli* NiCo21(DE3) by the calcium chloride method. The obtained transformant was designated as transformant m6b.

Extraction of recombinant vector pET-m6b from the transformant m6b and confirmation of the base sequence of the DNA encoding improved recombinant FcγRIIb-m6b and its surrounding region were carried out by the same method as described in (2) of Example 1.

(3) Production of Improved Recombinant FcγRIIb-m6b

Improved recombinant FcγRIIb-m6b was produced using transformant m6b by the same method as described in (3) of Example 1. The productivity of improved recombinant FcγRIIb-m6b per 1 L of culture solution was 4.1±0.4 mg (n=2).

Example 11 IgG Affinity of Improved Recombinant FcγRIIb

(1) IgG Affinity of Improved Recombinant FcγRIIb-a4F3, Improved Recombinant FcγRIIb-a2E2 and Improved Recombinant FcγRIIb-a15A6

The IgG affinities of the improved recombinant FcγRIIb-a4F3 described in Example 1, the improved recombinant FcγRIIb-a2E2 described in Example 2 and the improved recombinant FcγRIIb-a15A6 described in Example 3 were evaluated.

The affinity for IgG was evaluated using ELISA method 1 described above. Specifically, experimentation was conducted under two conditions: IgG immobilization conditions according to ELISA method 1, and non-IgG immobilization conditions in which ELISA method 1 was altered so that the IgG immobilization procedure was not carried out (each experiment carried out twice in series). The samples used for the experiment were soluble protein extracts including each improved recombinant FcγRIIb described in Example 1 to Example 3, diluted 5-fold with 50 mM Tris-HCl buffer (pH 8.0).

As a control, the same experiment was conducted using a soluble protein extract prepared by the culturing method and soluble protein extract preparation method described in (3) of Example 1, using transformants obtained by transforming *E. coli* NiCo21(DE3) with pETMalE21 vector (hereunder referred to as "sample MalE21") and 50 mM Tris-HCl buffer (pH 8.0) (hereunder referred to as "sample buffer").

The evaluation results for the IgG affinity of each improved recombinant FcγRIIb are shown in Table 8. As shown in Table 8, a high detected value was obtained only when the experiment was conducted by ELISA method 1 using the sample for each improved recombinant FcγRIIb (IgG immobilization conditions). The results confirmed that improved recombinant FcγRIIb-a4F3, improved recombinant FcγRIIb-a2E2 and improved recombinant FcγRIIb-a15A6 have affinity for IgG.

TABLE 8

| | Detected values in ELISA method 1 (absorbance, OD450) (n = 2) | |
|---|---|---|
| Sample name | Conditions with IgG immobilization in ELISA method 1 | Conditions without IgG immobilization in ELISA method 1 |
| Improved recombinant FcγRIIb-a4F3 | 0.33 ± 0.04 | 0.05 ± 0.00 |
| Improved recombinant FcγRIIb-a2E2 | 0.30 ± 0.04 | 0.05 ± 0.00 |
| Improved recombinant FcγRIIb-a15A6 | 0.37 ± 0.04 | 0.05 ± 0.00 |
| Sample MalE21 | 0.07 ± 0.00 | 0.05 ± 0.00 |
| Sample buffer | 0.09 ± 0.01 | 0.05 ± 0.01 |

(2) IgG Affinity of Improved Recombinant FcγRIIb-m3

The IgG affinity of the improved recombinant FcγRIIb-m3 of Example 4 was evaluated. The IgG affinity was evaluated in the same manner as the method described above. The sample used for evaluation of the IgG affinity was a soluble protein extract including the improved recombinant FcγRIIb-m3 of Example 4, diluted 5-fold with 50 mM Tris-HCl buffer (pH 8.0). As a control, the same experiment was conducted using the sample buffer.

The evaluation results for IgG affinity are shown in Table 9. As shown in Table 9, a high detected value was obtained only when ELISA method 1 was conducted using the sample for the improved recombinant FcγRIIb-m3 (IgG immobilization conditions). The results confirmed that the improved recombinant FcγRIIb-m3 has affinity for IgG.

TABLE 9

| Sample name | Detected values in ELISA method 1 (absorbance, OD450) (n = 2) | |
|---|---|---|
| | Conditions with IgG immobilization in ELISA method 1 | Conditions without IgG immobilization in ELISA method 1 |
| Improved recombinant FcγRIIb-m3 | 0.50 ± 0.07 | 0.05 ± 0.00 |
| Sample buffer | 0.07 ± 0.00 | 0.05 ± 0.00 |

(3) IgG Affinities of Improved Recombinant FcγRIIb-d10D5, Improved Recombinant FcγRIIb-d11D7 and Improved Recombinant FcγRIIb-d6E2

The IgG affinities of the improved recombinant FcγRIIb-d10D5 of Example 5, the improved recombinant FcγRIIb-d11D7 of Example 6 and the improved recombinant FcγRIIb-d6E2 of Example 7 were evaluated. The IgG affinity was evaluated in the same manner as the method described above. The samples used for evaluation of IgG affinity were soluble protein extracts including each improved recombinant FcγRIIb described in Example 5 to Example 7, diluted 5-fold with 50 mM Tris-HCl buffer (pH 8.0). As a control, the same experiment was conducted using the sample buffer.

The evaluation results for IgG affinity are shown in Table 10. As shown in Table 10, a high detected value was obtained only when ELISA method 1 was conducted using the sample for each improved recombinant FcγRIIb (IgG immobilization conditions). The results confirmed that the improved recombinant FcγRIIb-d10D5, improved recombinant FcγRIIb-d11D7 and improved recombinant FcγRIIb-d6E2 have affinity for IgG.

TABLE 10

| Sample name | Detected values in ELISA method 1 (absorbance, OD450) (n = 2) | |
|---|---|---|
| | Conditions with IgG immobilization in ELISA method 1 | Conditions without IgG immobilization in ELISA method 1 |
| Improved recombinant FcγRIIb-d10D5 | 0.66 ± 0.13 | 0.05 ± 0.00 |
| Improved recombinant FcγRIIb-d11D7 | 0.76 ± 0.05 | 0.05 ± 0.00 |
| Improved recombinant FcγRIIb-d6E2 | 0.71 ± 0.14 | 0.05 ± 0.00 |
| Sample buffer | 0.07 ± 0.01 | 0.04 ± 0.00 |

(4) IgG Affinities of Improved Recombinant FcγRIIb-m5b, Improved Recombinant FcγRIIb-m5c and Improved Recombinant FcγRIIb-m6b The IgG affinities of the improved recombinant FcγRIIb-m5b of Example 8, the improved recombinant FcγRIIb-m5c of Example 9 and the improved recombinant FcγRIIb-m6b of Example 10 were evaluated. The IgG affinity was evaluated in the same manner as the method described above. The samples used for evaluation of IgG affinity were soluble protein extracts including each improved recombinant FcγRIIb described in Example 8 to Example 10, diluted 5-fold with 50 mM Tris-HCl buffer (pH 8.0). As a control, the same experiment was conducted using the sample buffer.

The evaluation results for IgG affinity are shown in Table 11. As shown in Table 11, a high detected value was obtained only when ELISA method 1 was conducted using the sample for each improved recombinant FcγRIIb (IgG immobilization conditions). The results confirmed that the improved recombinant FcγRIIb-m5b, improved recombinant FcγRIIb-m5c and improved recombinant FcγRIIb-m6b have affinity for IgG.

TABLE 11

| Sample name | Detected values in ELISA method 1 (absorbance, OD450) (n = 2) | |
|---|---|---|
| | Conditions with IgG immobilization in ELISA method 1 | Conditions without IgG immobilization in ELISA method 1 |
| Improved recombinant FcγRIIb-m5b | 0.80 ± 0.02 | 0.04 ± 0.01 |
| Improved recombinant FcγRIIb-m5c | 0.79 ± 0.02 | 0.04 ± 0.01 |
| Improved recombinant FcγRIIb-m6b | 0.84 ± 0.02 | 0.04 ± 0.01 |
| Sample buffer | 0.11 ± 0.01 | 0.05 ± 0.01 |

Example 12 Thermal Stability of Improved Recombinant FcγRIIb

The thermal stability was evaluated for the improved recombinant FcγRIIb-a4F3 of Example 1, the improved recombinant FcγRIIb-a2E2 of Example 2, the improved recombinant FcγRIIb-a15A6 of Example 3, the improved recombinant FcγRIIb-m3 of Example 4, the improved recombinant FcγRIIb-d10D5 of Example 5, the improved recombinant FcγRIIb-d11D7 of Example 6, the improved recombinant FcγRIIb-d6E2 of Example 7, the improved recombinant FcγRIIb-m5b of Example 8, the improved recombinant FcγRIIb-m5c of Example 9 and the improved recombinant FcγRIIb-m6b of Example 10.

The samples used for evaluation of thermal stability were soluble protein extracts including each improved recombinant FcγRIIb of Example 1 to Example 10. Each sample was diluted 200-fold with 50 mM Tris-HCl buffer (pH 8.0), treated at 4° C. for 30 minutes, heat treated at 55° C. for 30 minutes and heat treated at 60° C. for 30 minutes. The improved recombinant FcγRIIb concentration of each treated sample was measured by ELISA method 2 described in (3) of Example 1. The proportions of the improved recombinant FcγRIIb concentration upon heat treatment at 55° C. for 30 minutes and heat treatment at 60° C. for 30 minutes were calculated for each sample, with 100% as the concentration of improved recombinant FcγRIIb upon treatment at 4° C. for 30 minutes, and were recorded as the detection rate after heat treatment (%). The experiment was conducted twice in series.

The evaluation results for the thermal stability of each improved recombinant FcγRIIb are shown in FIG. 1. As shown in FIG. 1, the thermal stability (detection rate after heat treatment) was highest with improved recombinant FcγRIIb-m6b, demonstrating that a larger number of the substitutions (1) to (6) in improved recombinant FcγRIIb tended to increase the thermal stability.

Comparative Example 1 Preparation of Recombinant FcγRIIb

Recombinant FcγRIIb consisting of the amino acid sequence set forth in SEQ ID NO: 1 was prepared.

(1) Preparation of DNA Including Base Sequence Encoding Recombinant FcγRIIb, Recombinant Vector pET-rhFcγRIIb, and Transformant rhFcγRIIb DNA including a base sequence encoding recombinant FcγRIIb (SEQ ID NO: 1), recombinant vector pET-rhFcγRIIb, and transformant rhFcγRIIb were prepared by the methods described in (1-1) and (1-2) of Example 1.

(2) Production of Recombinant FcγRIIb

Recombinant FcγRII was produced using transformant rhFcγRIIb by the same method as described in (3) of Example 1. The productivity of recombinant FcγRIIb per 1 L of culture solution was 0.8±0.0 mg (n=2).

The productivity of recombinant FcγRIIb for Comparative Example 1 and the productivity of each improved recombinant FcγRIIb described in Example 1 to Example 10 are summarized in Table 12. As shown in Table 12, all of the improved recombinant FcγRIIb of Example 1 to Example 10 had higher productivity than recombinant FcγRIIb (Comparative Example 1). As also shown in Table 12, a larger number of the substitutions (1) to (6) in improved recombinant FcγRIIb tended to increase productivity. In addition, since productivity for improved recombinant FcγRIIb including substitution (1) (improved recombinant FcγRIIb of Example 4 to Example 10) was increased by at least 2-fold compared to the recombinant FcγRIIb of Comparative Example 1, this indicates that substitution (1) is particularly useful for increasing productivity.

Comparative Example 2 Thermal Stability of Recombinant FcγRIIb

The recombinant FcγRIIb of Comparative Example 1 was evaluated for thermal stability. The samples used for evaluation of thermal stability were soluble protein extracts including the recombinant FcγIIb of Comparative Example 1. The experiment method was the same as described in Example 12.

The evaluation results for the thermal stability of recombinant FcγRIIb are shown in FIG. 1. As shown in FIG. 1, all of the improved recombinant FcγRIIb of Example 1 to Example 10 had higher thermal stability (detection rate after heat treatment) than recombinant FcγRIIb (Comparative Example 1).

Example 13 Acid Stability of Improved Recombinant FcγRIIb

The acid stability of the improved recombinant FcγRIIb-m6b of Example 10 was evaluated. After diluting a sample solution of the soluble protein extract including the improved recombinant FcγRIIb-m6b of Example 10 with purified water to 30 μg/mL, 100 μL of the diluted sample solution was mixed with 200 μL of 0.1 M glycine hydrochloride buffer (pH 3.0), and allowed to stand at 30° C. for 24 hours, 48 hours or 72 hours.

The antibody binding activity of the protein after acid treatment with glycine hydrochloride buffer (pH 3.0) and the antibody binding activity of the protein without acid treatment were measured by ELISA method 2 described in (3) of Example 1. Next, the antibody binding activity with acid

TABLE 12

| Example or Comp. Example | Sample name | SEQ ID NO: | Amino acid substitution | Sample productivity (mg/L-culture solution) (n = 2) |
| --- | --- | --- | --- | --- |
| Example 1 | Improved recombinant FcγRIIb-a4F3 | 2 | Substitution (3) | 1.0 ± 0.1 |
| Example 2 | Improved recombinant FcγRIIb-a2E2 | 3 | Substitution (6) | 1.3 ± 0.0 |
| Example 3 | Improved recombinant FcγRIIb-a15A6 | 4 | Substitution (1) | 1.7 ± 0.0 |
| Example 4 | Improved recombinant FcγRIIb-m3 | 5 | Substitution (1), substitution (3), substitution (6) | 2.3 ± 0.2 |
| Example 5 | Improved recombinant FcγRIIb-d10D5 | 6 | Substitution (1), substitution (3), substitution (5), substitution (6) | 2.5 ± 0.1 |
| Example 6 | Improved recombinant FcγRIIb-d11D7 | 7 | Substitution (1), substitution (3), substitution (4), substitution (6) | 3.0 ± 0.3 |
| Example 7 | Improved recombinant FcγRIIb-d6E2 | 8 | Substitution (1), substitution (2), substitution (3), substitution (6) | 3.4 ± 0.0 |
| Example 8 | Improved recombinant FcγRIIb-m5b | 9 | Substitution (1), substitution (2), substitution (3), substitution (5), substitution (6) | 3.0 ± 0.9 |
| Example 9 | Improved recombinant FcγRIIb-m5c | 10 | Substitution (1), substitution (3), substitution (4), substitution (5), substitution (6) | 3.5 ± 0.6 |
| Example 10 | Improved recombinant FcγRIIb-m6b | 11 | Substitution (1), substitution (2), substitution (3), substitution (4), substitution (5), substitution (6) | 4.1 ± 0.4 |
| Comp. Example 1 | Recombinant FcγRIIb | 1 | | 0.8 ± 0.0 | treatment was divided by the antibody binding activity without acid treatment, to calculate the residual activity.

Comparative Example 3 Acid Stability of Recombinant FcγRIIb

The recombinant FcγRIIb of Comparative Example 1 was evaluated for acid stability. The acid stability was evaluated by the same method as described in Example 13, except that a soluble protein extract including the recombinant FcγRIIb of Comparative Example 1 was used as the sample.

The evaluation results for the acid stability of improved recombinant FcγRIIb-m6b (Example 10) and recombinant FcγRIIb (Comparative Example 1) are shown in Table 13. As shown in Table 13, the improved recombinant FcγRIIb-m6b of Example 10 had higher acid stability (residual activity after acid treatment) than the recombinant FcγRIIb of Comparative Example 1. This indicates that the improved recombinant FcγRIIb has both increased thermal stability (Example 12 and Comparative Example 2) as well as increased acid stability, compared to recombinant FcγRIIb.

SEQ ID NO: 84 (5'-TGTGGTATGGCTGTGCAGG-3') or SEQ ID NO: 85 (5'-TCGGCATGGGGTCAGGTG-3') was used as the sequencing primer.

The amino acid sequence of polypeptide FcγRIIb-m6b_Cys expressed by expression vector pTrc-m6b_Cys is set forth in SEQ ID NO: 86, and the sequence of the polynucleotide encoding the polypeptide is set forth in SEQ ID NO: 87. In the amino acid sequence set forth in SEQ ID NO: 86, the amino acid residues from methionine at position 1 to alanine at position 22 are the PelB signal peptide, methionine at position 23 and glycine at position 24 are linkers, the amino acid residues from threonine at position 25 to glutamine at position 197 are the improved FcγRIIb extracellular domain (corresponding to the amino acid residues from threonine at position 29 to glutamine at position 201 in the amino acid sequence set forth in SEQ ID NO: 1), glycine at position 198 and cysteine at position 199 are linkers, and the amino acid residues from arginine at position 200 to glycine at position 205 are a cysteine tag. Among the amino acid substitutions in the improved FcγRIIb extra-

TABLE 13

| Example or Comp. | Sample name | SEQ ID NO: | Amino acid substitution | Residual acid resistance activity (%) | | | |
|---|---|---|---|---|---|---|---|
| | | | | 0 hours | 24 hours | 48 hours | 72 hours |
| Example 10 | Improved recombinant FcγRIIb-m6b | 11 | Substitution (1), substitution (2), substitution (3), substitution (4), substitution (5), substitution (6) | 100 | 82.4 | 52.3 | 43.3 |
| Comp. Example 1 | Recombinant FcγRIIb | 1 | | 100 | 8.1 | 0 | 0 |

Example 14 Preparation of Cysteine Tag-Added Improved Recombinant FcγRIIb-m6b_Cys (1) PCR was carried out using as the template an expression vector pET-m6b including the polynucleotide set forth in SEQ ID NO: 23 encoding a protein consisting of the amino acid sequence set forth in SEQ ID NO: 11, prepared in Example 10. The PCR primers used were oligonucleotides consisting of the sequences set forth in SEQ ID NO: 82 (5'-TAGCCATGGGCATGCGTACCGAAGATCTG-CCGAAAGC-3') and SEQ ID NO: 83 (5'-CCCAAGCT-TATCCGCAGGTATCGTTGCGGCAGCCCTGCACGGT-GATAGTAACCGGCT TGCTGCTATA-3'). The PCR was conducted by preparing a reaction mixture with the composition shown in Table 3, and then heat treating the reaction mixture at 98° C. for 5 minutes, and repeating 30 cycles of a reaction where one cycle consisted of a first step at 98° C. for 10 seconds, a second step at 55° C. for 5 seconds and a third step at 72° C. for 1 minute.

(2) The polynucleotide obtained in (1) was purified and digested with restriction enzymes NcoI and HindIII, and then ligated with expression vector pTrc-PelBV3 constructed by the method described in WO2015/199154, which had been previously digested with restriction enzymes NcoI and HindIII, and the ligation product was used to transform *E. coli* W3110.

(3) The obtained transformants were cultured in LB medium containing 100 μg/mL carbenicillin, and then a QIAprep Spin Miniprep kit (product of Qiagen Inc.) was used to obtain expression vector pTrc-m6b_Cys.

(4) The nucleotide sequence of pTrc-m6b_Cys was analyzed in the same manner as (2) of Example 1, except that the oligonucleotide consisting of the sequence set forth in cellular domain, valine at position 68 (substitution (1)) of SEQ ID NO: 11 corresponds to position 64 in SEQ ID NO: 86, glutamine at position 80 (substitution (2)) of SEQ ID NO: 11 corresponds to position 76 in SEQ ID NO: 86, threonine at position 84 (substitution (3)) of SEQ ID NO: 11 corresponds to position 80 in SEQ ID NO: 86, threonine at position 90 (substitution (4)) of SEQ ID NO: 11 corresponds to position 86 in SEQ ID NO: 86, serine at position 91 (substitution (5)) of SEQ ID NO: 11 corresponds to position 87 in SEQ ID NO: 86, and arginine at position 125 (substitution (6)) of SEQ ID NO: 11 corresponds to position 121 in SEQ ID NO: 86.

Example 15 Preparation of Cysteine Tag-Added Improved Recombinant FcγRIIb-m6b_Cys (1) Transformants expressing the cysteine tag-added improved recombinant FcγRIIb-m6b_Cys constructed in Example 14 were inoculated into 400 mL of 2YT liquid medium (16 g/L peptone, 10 g/L yeast extract and 5 g/L sodium chloride) containing 100 μg/mL carbenicillin in a 2 L baffle flask, and aerobically shake cultured overnight at 37° C., as preculturing.

(2) After inoculating 180 mL of the culture solution of (1) into 1.8 L of liquid medium containing 10 g/L glucose, 20 g/L yeast extract, 3 g/L trisodium phosphate dodecahydrate, 9 g/L disodium hydrogenphosphate dodecahydrate, 1 g/L ammonium chloride and 100 mg/L carbenicillin, a 3 L fermenter (product of Biott) was used for main culturing. The conditions were set to a temperature of 30° C., a pH of 6.9 to 7.1, an aeration rate of 1 VVM and a dissolved oxygen concentration at 30% saturated concentration, and main culturing was commenced. For pH regulation, 50% phosphoric acid was used as the acid and 14% (w/v) ammonia water was used as the alkali, the dissolved oxygen was controlled by varying the stirring speed, and the stirring rotational speed was set with a lower limit of 500 rpm and an upper limit of 1000 rpm. After the start of culturing, and when the glucose concentration was no longer measurable, feeding culture medium (248.9 g/L glucose, 83.3 g/L yeast extract, 7.2 g/L magnesium sulfate heptahydrate) was added while controlling the dissolved oxygen (DO).

(3) When the absorbance at 600 nm (OD600 nm) reached about 150 as a measure of the cell mass, the culturing temperature was lowered to 25° C., and upon confirming that the preset temperature had been reached, IPTG was added to a final concentration of 0.5 mM and culturing was continued at 25° C.

(4) Culturing was terminated at about 48 hours after the start of culturing, and the cells were recovered by centrifugation of the culture solution at 8000 rpm for 20 minutes at 4° C.

(5) The collected cells were suspended in 20 mM Tris-HCl buffer (pH 7.0) to 5 mL/1 g-cells, and an ultrasonic generator (INSONATOR 201M, product of Kubota Corp.) was used to disrupt the cells at 4° C. for about 10 minutes, with an output of about 150 W. The cell disruptate was centrifuged twice at 4° C. for 20 minutes, 8000 rpm, and the supernatant was collected.

(6) The supernatant obtained in (5) was applied to a VL32×250 column (Merck, Ltd. Millipore) packed with 140 mL of TOYOPEARL CM-650 M (Tosoh Corp.) that had been previously equilibrated with 20 mM phosphate buffer (8 mM sodium dihydrogenphosphate, 12 mM disodium hydrogenphosphate) (pH 7.0), at a flow rate of 5 mL/min. After rinsing with the buffer used for equilibration, it was eluted with 20 mM phosphate buffer (pH 7.0) containing 0.5 M sodium chloride.

(7) The eluate obtained in (6) was applied to an XK26/20 column (product of GE Healthcare) packed with 90 mL of IgG Sepharose (product of GE Healthcare) that had been previously equilibrated with 20 mM Tris-HCl buffer (pH 7.4) containing 150 mM sodium chloride. After rinsing with the buffer used for equilibration, elution was performed with 0.1 M glycine hydrochloride buffer (pH 3.0). The eluate was restored to nearly neutral pH by addition of 1 M Tris-HCl buffer (pH 8.0) at ¼ the volume of the eluate.

The purification yielded approximately 20 mg of high-purity cysteine tag-added improved recombinant FcγRIIb-m6b_Cys.

Example 16 Preparation of Improved Recombinant FcγRIIb-m6b_Cys Immobilized Gel and Evaluation of Separation Performance (1) After activating the hydroxyl groups on the surface of 2 mL of a hydrophilic vinyl polymer for separation (Tosoh Corp.) using iodoacetyl groups, 4 mg of the cysteine tag-added improved recombinant FcγRIIb-m6b_Cys prepared in Example 15 was reacted, to obtain a FcγRIIb-m6b immobilized gel.

(2) A FcγRIIb-m6b column was prepared by packing a φ4.6 mm×75 mm stainless steel column with 1.2 mL of the FcγRIIb-m6b immobilized gel prepared in (1).

(3) The FcγRIIb-m6b column prepared in (2) was connected to a high-performance liquid chromatography apparatus (Tosoh Corp.) and equilibrated with 50 mM Tris-glycine buffer (pH 8.5) as equilibrating buffer.

(4) Monoclonal antibody diluted to 1.0 mg/mL with PBS (Phosphate Buffered Saline) (pH 7.4) (Rituxan, (Zenyaku Kogyo), bevacizumab; infliximab) and polyclonal antibody (human immunoglobulin) were added at 5 μL at a flow rate of 0.6 mL/min.

(5) After rinsing for 10 minutes with equilibrating buffer while maintaining a flow rate of 0.6 mL/min, the monoclonal antibody adsorbed with a pH gradient produced with 50 mM Tris-glycine buffer (pH 3.0) (a gradient for 100% 50 mM Tris-glycine buffer (pH 3.0) in 30 minutes) was eluted.

Figure 2:
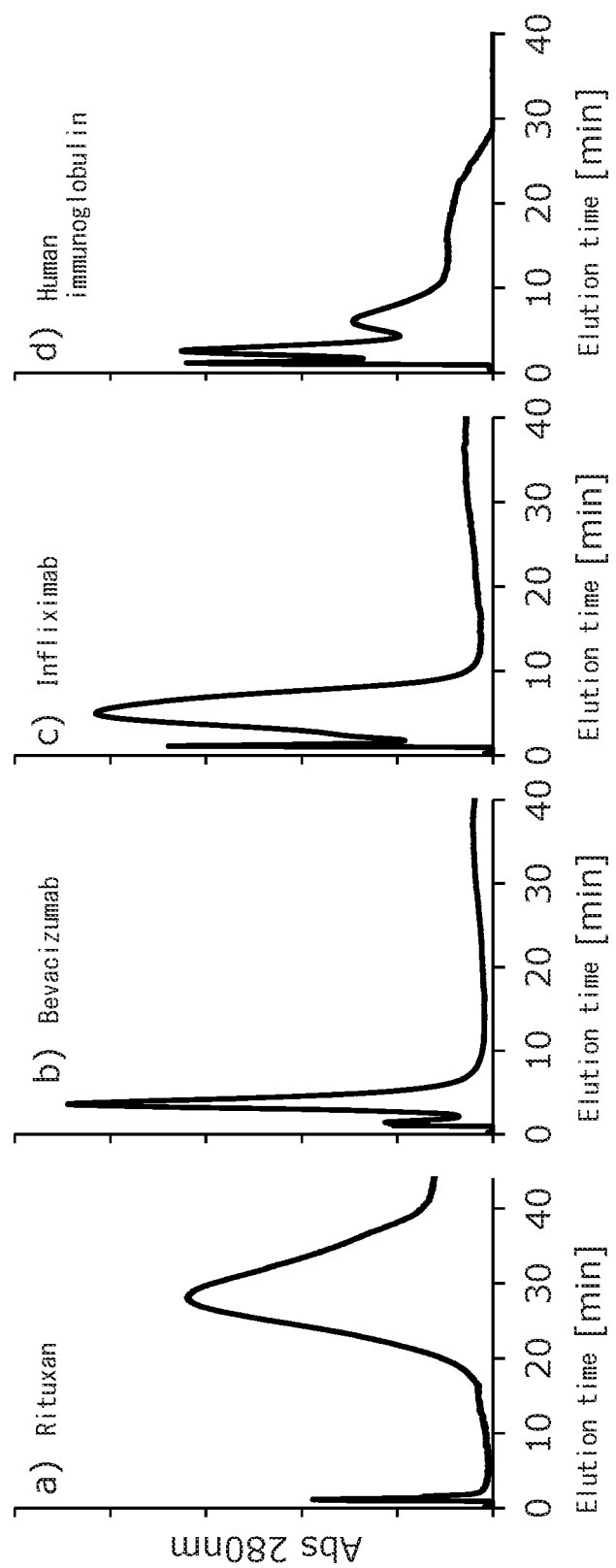
FIG. 2 is a set of chromatograms showing the results of separating different antibodies using a column packed with insoluble support immobilizing the improved recombinant FcγRIIb of the invention.

The result (elution pattern) is shown in FIG. 2. The results in FIG. 2 are for applying a) Rituxan, b) bevacizumab, c) infliximab and d) human immunoglobulin to the FcγRIIb-m6b column. Since the structure of each antibody (amino acid sequence or attached sugar chain structure) differs depending on differences in the type of monoclonal antibody or polyclonal antibody, the differences in their structure contribute to interaction with Fc-binding protein, with each antibody being separated into a different peak.

Example 17 Preparation of Improved Recombinant FcγRIIa-m6

(1) Preparation of DNA Including Base Sequence Encoding Improved Recombinant FcγRIIa-m6

DNA including a base sequence (SEQ ID NO: 91) encoding the amino acid sequence of improved recombinant FcγRIIa-m6 including substitution (7), substitution (8), substitution (9), substitution (10), substitution (11) and substitution (12) (SEQ ID NO: 89) was prepared in the following manner.

PCR was carried out using the recombinant vector pET-m6b described in Reference Example 2 as template DNA and oligonucleotides consisting of the sequences set forth in SEQ ID NO: 92 and SEQ ID NO: 93 as PCR primers. PCR was carried out by preparing a reaction mixture with the composition shown in Table 14 and reacting the reaction mixture under the conditions shown in Table 15. The obtained PCR product was designated as Am6p1.

TABLE 14

| Composition | Volume |
| --- | --- |
| Template DNA | 1 μL |
| 10 pmol/μL PCR primer | 2 μL each |
| 2.5 U/μL PrimeSTAR HS (Takara Bio, Inc.) | 0.25 μL |
| 5 × PrimeSTAR buffer (Takara Bio, Inc.) | 10 μL |
| dNTPs (Takara Bio, Inc.) | 4 μL |
| H$_2$O | up to 50 μL |

TABLE 15

| Reaction temperature (° C.) | Time (sec) | |
| --- | --- | --- |
| 98 | 10 | 30 cycles |
| 50 | 5 | |
| 72 | 60 | |

PCR was carried out using the recombinant vector pET-m6b described in Reference Example 2 as template DNA and oligonucleotides consisting of the sequences set forth in SEQ ID NO: 94 and SEQ ID NO: 95 as PCR primers. PCR was carried out by preparing a reaction mixture with the composition shown in Table 14 and reacting the reaction mixture under the conditions shown in Table 15. The obtained PCR product was designated as Am6p2.

PCR was carried out using the recombinant vector pET-m6b described in Reference Example 2 as template DNA and oligonucleotides consisting of the sequences set forth in SEQ ID NO: 96 and SEQ ID NO: 97 as PCR primers. PCR was carried out by preparing a reaction mixture with the composition shown in Table 14 and reacting the reaction mixture under the conditions shown in Table 15. The obtained PCR product was designated as Am6p3.

PCR products Am6p1, Am6p2 and Am6p3 were each electrophoresed using agarose gel, and then the gel portion including the target PCR product was cut out and extracted using a QIAquick Gel extraction kit (product of Qiagen Inc.) for purification (purification by the same method will hereunder be referred to simply as "DNA fragment purification"). PCR was carried out by mixing the DNA fragment-purified PCR products Am6p1, Am6p2 and Am6p3 and then preparing a reaction mixture with the composition shown in Table 16 and reacting the reaction mixture under the conditions shown in Table 17. The obtained PCR product was designated as Am6p4.

TABLE 16

| Composition | Volume |
| --- | --- |
| PCR product | 1 µL each |
| 2.5 U/µL PrimeSTAR HS (Takara Bio, Inc.) | 0.25 µL |
| 5 × PrimeSTAR buffer (Takara Bio, Inc.) | 10 µL |
| 2.5 mM dNTPs | 4 µL |
| H$_2$O | up to 50 µL |

TABLE 17

| Reaction temperature (° C.) | Time (sec) | |
| --- | --- | --- |
| 98 | 10 | |
| 50 | 5 | 5 cycles |
| 72 | 60 | |

PCR was carried out using the PCR product Am6p4 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was designated as Am6p5.

PCR was carried out using the DNA fragment-purified PCR product Am6p5 as template DNA and oligonucleotides consisting of the sequences set forth in SEQ ID NO: 92 and SEQ ID NO: 98 as PCR primers. PCR was carried out by preparing a reaction mixture with the composition shown in Table 14 and reacting the reaction mixture under the conditions shown in Table 15. The obtained PCR product was designated as Am6p6.

PCR was carried out using the DNA fragment-purified PCR product Am6p5 as template DNA and oligonucleotides consisting of the sequences set forth in SEQ ID NO: 99 and SEQ ID NO: 100 as PCR primers. PCR was carried out by preparing a reaction mixture with the composition shown in Table 14 and reacting the reaction mixture under the conditions shown in Table 15. The obtained PCR product was designated as Am6p7.

PCR was carried out using the DNA fragment-purified PCR product Am6p5 as template DNA and oligonucleotides consisting of the sequences set forth in SEQ ID NO: 101 and SEQ ID NO: 97 as PCR primers. PCR was carried out by preparing a reaction mixture with the composition shown in Table 14 and reacting the reaction mixture under the conditions shown in Table 15. The obtained PCR product was designated as Am6p8.

PCR was carried out by mixing the DNA fragment-purified PCR products Am6p6, Am6p7 and Am6p8 and then preparing a reaction mixture with the composition shown in Table 16 and reacting the reaction mixture under the conditions shown in Table 17. The obtained PCR product was designated as Am6p9.

PCR was carried out using the PCR product Am6p9 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was designated as Am6p10.

PCR was carried out using the DNA fragment-purified PCR product Am6p10 as template DNA and oligonucleotides consisting of the sequences set forth in SEQ ID NO: 102 and SEQ ID NO: 103 as PCR primers. PCR was carried out by preparing a reaction mixture with the composition shown in Table 14 and reacting the reaction mixture under the conditions shown in Table 15. The obtained PCR product was designated as Am6p11.

PCR was carried out using the DNA fragment-purified PCR product Am6p10 as template DNA and oligonucleotides consisting of the sequences set forth in SEQ ID NO: 104 and SEQ ID NO: 97 as PCR primers. PCR was carried out by preparing a reaction mixture with the composition shown in Table 14 and reacting the reaction mixture under the conditions shown in Table 15. The obtained PCR product was designated as Am6p12.

PCR was carried out by mixing the DNA fragment-purified PCR products Am6p11 and Am6p12 and then preparing a reaction mixture with the composition shown in Table 16 and reacting the reaction mixture under the conditions shown in Table 17. The obtained PCR product was designated as Am6p13.

PCR was carried out using the PCR product Am6p13 as template DNA and oligonucleotides consisting of the sequences set forth in SEQ ID NO: 102 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification to obtain DNA including a base sequence encoding the improved recombinant FcγRIIa-m6.

(2) Preparation of Recombinant Vector Comprising DNA Encoding Improved Recombinant FcγRIIa-m6 and Transformant Comprising it After digesting DNA including a base sequence encoding the improved recombinant FcγRIIa-m6 with restriction enzymes NcoI and HindIII, it was subjected to DNA fragment purification, and linked by ligation to a pETMalE21 vector (pETMalE21 vector prepared by the method reported by Hatayama & Ide (Protein Expr. Purif., 111, 1-8, 2015)) that had been previously digested with restriction enzymes NcoI and HindIII, to prepare a recombinant vector (hereunder referred to as "recombinant vector pET-Am6"). The recombinant vector pET-Am6 was used to transform E. coli NiCo21(DE3) (product of New England Biolabs) by the calcium chloride method. The obtained transformant was designated as transformant Am6.

Extraction of recombinant vector pET-Am6 from transformant Am6, and confirmation of the base sequences of DNA encoding improved recombinant FcγRIIa-m6 and it surrounding region were carried out, respectively, using the recombinant vector extraction and sequence analysis described below.

Recombinant vector extraction: The transformant was cultured (LB medium containing 50 μg/mL kanamycin (10 g/L Tryptone, 5 g/L Yeast extract, 5 g/L NaCl), overnight at 37° C., aerobic conditions), and a QIAprep Spin Miniprep Kit was used to extract the recombinant vector.

Sequence analysis: DNA encoding improved recombinant FcγRIIa-m6 and its surrounding region from the recombinant vector was provided to cycle sequencing reaction using a Big Dye Terminator Cycle Sequencing FS Read Reaction kit (product of PE Applied Biosystems), based on the chain terminator method, and the base sequence was analyzed with a fully automatic DNA sequencer: ABI Prism 3700 DNA analyzer (PE Applied Biosystems). For the analysis, an oligonucleotide consisting of the sequence set forth in SEQ ID NO: 92 or SEQ ID NO: 97 was used as the sequencing primer.

(3) Production of Improved Recombinant FcγRIIa-m6

Transformant Am6 was inoculated into 5 mL of LB medium containing 50 μg/mL kanamycin and precultured by aerobic shake culture overnight at 37° C. After preculturing, 1% (v/v) of the preculturing solution was inoculated into 20 mL of LB medium containing 0.01 mM IPTG and 50 μg/mL kanamycin and aerobically shake cultured at 20° C. for 24 hours, to produce improved recombinant FcγRIIa-m6.

A BugBuster Protein extraction kit (Novagen) was used to collect a soluble protein extract containing improved recombinant FcγRIIa-m6 from cells harvested by centrifugal separation from the culture solution. The concentration of the improved recombinant FcγRIIa-m6 in the soluble protein extract was measured by ELISA method 2 described below. As a result of calculation based on the concentration of the improved recombinant FcγRIIa-m6 in the soluble protein extract, the productivity of improved recombinant FcγRIIa-m6 per 1 L of culture solution was 4.7±0.1 mg (n=2, collection and measurement of the soluble protein extract conducted twice in series).

ELISA method 2: After preparing anti-FcγRIIa antibody (Human FcγRIIA/CD32a Antibody) (product of R & D Systems, Catalog No.: AF1875) to a concentration of 1 μg/mL in 50 mM Tris-HCl buffer (pH 8.0), it was added at 100 μL/well into each well of a 96-well microplate (MaxiSorp, Nunc), and the anti-FcγRIIa antibody was immobilized (at 4° C. for 18 hours). After immobilization was complete, the solution in each well was discarded and TBS-B buffer (20 mM Tris-HCl (pH 8.0) containing 137 mM NaCl, 2.68 mM KCl and 0.5% (w/v) bovine serum albumin) was added to each well for blocking (at 30° C. for 2 hours). After rinsing each well with rinsing buffer (20 mM Tris-HCl buffer (pH 7.5) containing 0.05% (w/v) Tween 20 and 150 mM NaCl), the prepared soluble protein extract was serially diluted with 50 mM Tris-HCl buffer (pH 8.0), and added to each well for reaction with the immobilized anti-FcγRIIa antibody (at 30° C. for 1.5 hours). Upon completion of the reaction, each well was rinsed with rinsing buffer, horseradish peroxidase-labeled anti-His-Tag antibody reagent (product of Bethyl) (diluted with 50 mM Tris-HCl buffer (pH 8.0)) was added to each well, and reaction was conducted at 30° C. for 1.5 hours. After the reaction, each well was rinsed with rinsing buffer, TMB Peroxidase Substrate (product of KPL) was added to each well, and the absorbance at 450 nm was measured. The concentration of the improved recombinant FcγRIIa-m6 in the soluble protein extract was determined from the measured absorbance, based on the measurement results for a known concentration of sugar chain-attached FcγRIIa (Recombinant Human Fc gamma RIIA/CD32a(R167) Protein, CF) (product of R & D Systems, Catalog No.: 1330-CD-050/CF).

Example 18 IgG Affinity of Improved Recombinant FcγRIIa-m6

The IgG affinity of the improved recombinant FcγRIIa-m6 of Example 17 was evaluated.

The affinity for IgG was evaluated using ELISA method 1 described above. Specifically, experimentation was conducted under two conditions: IgG immobilization conditions according to ELISA method 1, and non-IgG immobilization conditions in which ELISA method 1 was altered so that the IgG immobilization procedure was not carried out (each experiment carried out twice in series). The sample used for the experiment was a soluble protein extract including the improved recombinant FcγRIIa-m6 of Example 17, diluted 5-fold with 50 mM Tris-HCl buffer (pH 8.0).

As a control, the same experiment was conducted using 50 mM Tris-HCl buffer (pH 8.0) (hereunder referred to as "sample buffer").

The evaluation results for the IgG affinity of the improved recombinant FcγRIIa-m6 are shown in Table 18. As shown in Table 18, a high detected value was obtained only when the experiment was conducted by ELISA method 1 using the sample for the improved recombinant FcγRIIa-m6 (IgG immobilization conditions). The results confirmed that the improved recombinant FcγRIIa-m6 has affinity for IgG.

TABLE 18

| | Detected values in ELISA method 1 (absorbance, OD450) (n = 2) | |
|---|---|---|
| Sample name | Conditions with IgG immobilization in ELISA method 1 | Conditions without IgG immobilization in ELISA method 1 |
| Improved recombinant FcγRIIa-m6 | 0.82 ± 0.04 | 0.05 ± 0.00 |
| Sample buffer | 0.08 ± 0.01 | 0.04 ± 0.00 |

Example 19 Thermal Stability of Improved Recombinant FcγRIIa-m6

The thermal stability of the improved recombinant FcγRIIa-m6 of Example 17 was evaluated.

The samples used for evaluation of thermal stability were soluble protein extracts including the improved recombinant FcγRIIa-m6 of Example 17. Each sample was diluted 200-fold with 50 mM Tris-HCl buffer (pH 8.0), and heat treated at 4° C. for 30 minutes or at 50° C. for 30 minutes. The improved recombinant FcγRIIa-m6 concentration of each treated sample was measured by ELISA method 2 described in (3) of Example 17. The proportion of the concentration of the improved recombinant FcγRIIa-m6 heat treated at 50° C. for 30 minutes was calculated, with the concentration of the improved recombinant FcγRIIa-m6 treated at 4° C. for 30 minutes as 100%, and was recorded as the detection rate after heat treatment (%). The experiment was conducted twice in series. As a result, the detection rate after heat treatment (%) of the improved recombinant FcγRIIa-m6 for 30 minutes at 50° C. was 86±9% (n=2).

Comparative Example 4 Preparation of Recombinant FcγRIIa

Recombinant FcγRIIa consisting of the amino acid sequence set forth in SEQ ID NO: 88 was prepared.

(1) Preparation of DNA Including Base Sequence Encoding Recombinant FcγRIIa (SEQ ID NO: 105)

PCR was carried out using the recombinant vector pET-rhFcγRIIb described in Reference Example 1 as template DNA and oligonucleotides consisting of the sequences set forth in SEQ ID NO: 92 and SEQ ID NO: 93 as PCR primers. PCR was carried out by preparing a reaction mixture with the composition shown in Table 14 and reacting the reaction mixture under the conditions shown in Table 15. The obtained PCR product was designated as Ap1.

PCR was carried out using the recombinant vector pET-rhFcγRIIb described in Reference Example 1 as template DNA and oligonucleotides consisting of the sequences set forth in SEQ ID NO: 94 and SEQ ID NO: 95 as PCR primers. PCR was carried out by preparing a reaction mixture with the composition shown in Table 14 and reacting the reaction mixture under the conditions shown in Table 15. The obtained PCR product was designated as Ap2.

PCR was carried out using the recombinant vector pET-rhFcγRIIb described in Reference Example 1 as template DNA and oligonucleotides consisting of the sequences set forth in SEQ ID NO: 96 and SEQ ID NO: 97 as PCR primers. PCR was carried out by preparing a reaction mixture with the composition shown in Table 14 and reacting the reaction mixture under the conditions shown in Table 15. The obtained PCR product was designated as Ap3.

PCR was carried out by mixing the DNA fragment-purified PCR products Ap1, Ap2 and Ap3 and then preparing a reaction mixture with the composition shown in Table 16 and reacting the reaction mixture under the conditions shown in Table 17. The obtained PCR product was designated as Ap4.

PCR was carried out using the PCR product Ap4 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was designated as Ap5.

PCR was carried out using the DNA fragment-purified PCR product Ap5 as template DNA and oligonucleotides consisting of the sequences set forth in SEQ ID NO: 92 and SEQ ID NO: 98 as PCR primers. PCR was carried out by preparing a reaction mixture with the composition shown in Table 14 and reacting the reaction mixture under the conditions shown in Table 15. The obtained PCR product was designated as Ap6.

PCR was carried out using the DNA fragment-purified PCR product Ap5 as template DNA and oligonucleotides consisting of the sequences set forth in SEQ ID NO: 99 and SEQ ID NO: 100 as PCR primers. PCR was carried out by preparing a reaction mixture with the composition shown in Table 14 and reacting the reaction mixture under the conditions shown in Table 15. The obtained PCR product was designated as Ap7.

PCR was carried out using the DNA fragment-purified PCR product Ap5 as template DNA and oligonucleotides consisting of the sequences set forth in SEQ ID NO: 101 and SEQ ID NO: 97 as PCR primers. PCR was carried out by preparing a reaction mixture with the composition shown in Table 14 and reacting the reaction mixture under the conditions shown in Table 15. The obtained PCR product was designated as Ap8.

PCR was carried out by mixing the DNA fragment-purified PCR products Ap6, Ap7 and Ap8 and then preparing a reaction mixture with the composition shown in Table 16 and reacting the reaction mixture under the conditions shown in Table 17. The obtained PCR product was designated as Ap9.

PCR was carried out using the PCR product Ap9 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was designated as Ap10.

PCR was carried out using the DNA fragment-purified PCR product Ap10 as template DNA and oligonucleotides consisting of the sequences set forth in SEQ ID NO: 102 and SEQ ID NO: 103 as PCR primers. PCR was carried out by preparing a reaction mixture with the composition shown in Table 14 and reacting the reaction mixture under the conditions shown in Table 15. The obtained PCR product was designated as Ap11.

PCR was carried out using the DNA fragment-purified PCR product Ap10 as template DNA and oligonucleotides consisting of the sequences set forth in SEQ ID NO: 104 and SEQ ID NO: 97 as PCR primers. PCR was carried out by preparing a reaction mixture with the composition shown in Table 14 and reacting the reaction mixture under the conditions shown in Table 15. The obtained PCR product was designated as Ap12.

PCR was carried out by mixing the DNA fragment-purified PCR products Ap11 and Ap12 and then preparing a reaction mixture with the composition shown in Table 16 and reacting the reaction mixture under the conditions shown in Table 17. The obtained PCR product was designated as Ap13.

PCR was carried out using the PCR product Ap13 as template DNA and oligonucleotides consisting of the sequences set forth in SEQ ID NO: 102 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification to obtain DNA including a base sequence encoding recombinant FcγRIIa.

(2) Preparation of Recombinant Vector Comprising DNA Encoding Recombinant FcγRIIa and Transformant Comprising it After digesting DNA including a base sequence encoding the recombinant FcγRIIa with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-rhFcγRIIa"). The recombinant vector pET-rhFcγRIIa was used to transform *E. coli* NiCo21 (DE3) by the calcium chloride method. The obtained transformant was designated as transformant rhFcγRIIa.

Extraction of recombinant vector pET-rhFcγRIIa from the transformant rhFcγRIIa and confirmation of the sequence of the DNA encoding improved recombinant FcγRIIa and its surrounding region were carried out by the same method as described in (2) of Example 17.

(3) Production of Recombinant FcγRIIa

Recombinant FcγRIIa was produced using transformant rhFcγRIIa by the same method as described in (3) of Example 17. The productivity of recombinant FcγRIIa per 1 L of culture solution was 1.5±0.4 mg (n=2). Table 19 shows a summary of these results and the results for productivity of the improved recombinant FcγRIIa-m6 of Example 17. As shown in Table 19, the improved recombinant FcγRIIa-m6 of Example 17 had even higher productivity than recombinant FcγRIIa. In other words, it is seen that the improved recombinant FcγRIIa-m6 had increased productivity (expression level) by having the substitutions (7) to (12).

TABLE 19

| Example or Comp. Example | Sample name | SEQ ID NO: | Amino acid substitution | Sample productivity (mg/L-culture solution) (n = 2) |
|---|---|---|---|---|
| Example 17 | Improved recombinant FcγRIIa-m6 | 89 | Substitution (7), substitution (8), substitution (9), substitution (10), substitution (11), substitution (12) | 4.7 ± 0.1 |
| Comp. Example 4 | Recombinant FcγRIIa | 88 | | 1.5 ± 0.4 |

Comparative Example 5

The recombinant FcγRIIa of Comparative Example 4 was evaluated for thermal stability. The samples used for evaluation of thermal stability were soluble protein extracts including the recombinant FcγRIIa of Comparative Example 4. The experiment method was the same as described in Example 19. As a result, the detection rate after heat treatment (%) of the recombinant FcγRIIa for 30 minutes at 50° C. was 66±4% (n=2).

As demonstrated by Example 19, the detection rate after heat treatment of the improved recombinant FcγRIIa-m6 for 30 minutes at 50° C. was 86±9% (n=2), which was higher thermal stability than recombinant FcγRIIa. In other words, it is seen that the improved recombinant FcγRIIa-m6 had increased thermal stability by having the substitutions (7) to (12).

Reference Example 1 Preparation of Recombinant Vector pET-rhFcγRIIb

The recombinant vector pET-rhFcγRIIb of Comparative Example 4 was prepared in the following manner. The recombinant vector pET-rhFcγRIIb is a recombinant vector used for expression of recombinant FcγRIIb consisting of the amino acid sequence set forth in SEQ ID NO: 106.

Based on the amino acid sequence of human FcγRIIb (SEQ ID NO: 107), the codons were converted to *E. coli* codons using the DNA works method (Nucleic Acid Res., 30, e43, 2002), to design a base sequence encoding the amino acid sequence of human FcγRIIb set forth in SEQ ID NO: 108.

DNA having a base sequence encoding the amino acid sequence of human FcγRIIb set forth in SEQ ID NO: 108 was prepared by two-stage PCR utilizing 42 different oligonucleotides set forth in SEQ ID NO: 109 to SEQ ID NO: 150.

In the first stage PCR, a reaction mixture with the composition shown in Table 20 was prepared, and then the reaction mixture was heated at 94° C. for 5 minutes, after which 25 cycles of a reaction were repeated, where one cycle consisted of a first step at 94° C. for 30 seconds, a second step at 62° C. for 30 seconds and a third step at 72° C. for 1 minute, and then treatment was carried out at 72° C. for 7 minutes and the mixture was cooled to 4° C. The "DNA mix" in Table 20 is a mixed solution of fixed sampled quantities of the 42 different oligonucleotides set forth in SEQ ID NO: 109 to SEQ ID NO: 150.

TABLE 20

| Composition | Volume |
|---|---|
| 10 × Pyrobest buffer II (Takara Bio, Inc.) | 5 μL |
| dNTPs (Takara Bio, Inc.) | 5 μL |

TABLE 20-continued

| Composition | Volume |
|---|---|
| DNA mix | 1 μL |
| Pyrobest DNA Polymerase (Takara Bio, Inc.) | 0.5 μL |
| H₂O | up to 50 μL |

In the second stage PCR, a reaction mixture with the composition shown in Table 21 was prepared, and then the reaction mixture was heated at 94° C. for 5 minutes, after which 25 cycles of a reaction were repeated, where one cycle consisted of a first step at 94° C. for 30 seconds, a second step at 65° C. for 30 seconds and a third step at 72° C. for 1 minute, and then treatment was carried out at 72° C. for 7 minutes and the mixture was cooled to 4° C.

TABLE 21

| Composition | Volume |
|---|---|
| 10 × Pyrobest buffer II (Takara Bio, Inc.) | 5 μL |
| dNTPs (Takara Bio, Inc.) | 5 μL |
| 10 pmol/μL oligonucleotide of SEQ ID NO: 109 | 2 μL |
| 10 pmol/μL oligonucleotide of SEQ ID NO: 150 | 2 μL |
| First stage PCR product | 1 μL |
| Pyrobest DNA Polymerase (Takara Bio, Inc.) | 0.5 μL |
| H₂O | up to 50 μL |

The 5'-end of the DNA fragment purified second-stage PCR product was phosphorylated (TaKaRa BKL Kit: Takara Bio, Inc.) and linked by ligation to a pUC19 plasmid vector that had been digested with restriction enzyme SmaI, and *E.* coli JM109 (Takara Bio, Inc.) was transformed. The obtained transformants were cultured in LB medium containing added 50 μg/mL ampicillin (and a QIAprep Spin Miniprep Kit (Qiagen Inc.) was used for extraction to prepare vector pUC-FcγRIIb.

PCR was carried out using the vector pUC-FcγRIIb as template DNA and oligonucleotides consisting of the sequences set forth in SEQ ID NO: 151 and SEQ ID NO: 152 as PCR primers. The PCR was carried out by preparing a reaction mixture with the composition shown in Table 14, then heat treating the reaction mixture at 98° C. for 5 minutes, subsequently repeating 30 cycles of a reaction where one cycle consisted of a first step at 98° C. for 10 seconds, a second step at 55° C. for 5 seconds and a third step at 72° C. for 1 minute, and then carrying out treatment at 72° C. for 5 minutes and cooling the mixture to 4° C. The obtained PCR product was designated as rhFcγRIIb-p1. After digesting the DNA fragment-purified PCR product rhFcγRIIb-p1 with restriction enzymes NcoI and HindIII, DNA fragment purification was carried out again. The PCR product rhFcγRIIb-p1 that had been digested with restriction enzymes NcoI and HindIII was linked by ligation with pETMalE21 vector that had been previously digested with restriction enzymes NcoI and HindIII (the pETMalE21 vector was prepared by the method reported by Hatayama & Ide (Protein Expr. Purif, 111, 1-8, 2015)), to construct recombinant vector pET-rhFcγRIIb, which was used for transformation of *E. coli* NiCo21(DE3) (product of New England Biolabs) by the calcium chloride method. The obtained transformant was designated as transformant rhFcγRIIb. Transformant rhFcγRIIb was cultured in LB medium containing added 50 μg/mL kanamycin, and a QIAprep Spin Miniprep Kit was used for extraction to prepare recombinant vector pET-rhFcγRIIb.

The base sequence of DNA from the restriction enzyme XbaI recognition sequence to the HindIII recognition sequence in recombinant vector pET-rhFcγRIIb is set forth in SEQ ID NO: 153. The region from adenine at position 50 to thymine at position 676 from the 5'-end of SEQ ID NO: 153 codes for recombinant FcγRIIb consisting of the amino acid sequence set forth in SEQ ID NO: 106.

Reference Example 2 Preparation of Recombinant Vector pET-m6b

The recombinant vector pET-m6b of Example 17 was prepared in the following manner. Modified recombinant vector pET-m6b was prepared based on the recombinant vector pET-rhFcγRIIb of Reference Example 1, using DNA amplification methods (PCR and error-prone PCR method), in the order: recombinant vector pET-a4F3, recombinant vector pET-m3, recombinant vector pET-m3(B) and recombinant vector pET-m6b.

(1) Preparation of Recombinant Vector pET-a4F3

Recombinant vector pET-a4F3 was prepared by the following method. The recombinant vector pET-a4F3 is a recombinant vector used for expression of improved recombinant FcγRIIb-a4F3 consisting of the amino acid sequence set forth in SEQ ID NO: 154.

Error-prone PCR was carried out using the recombinant vector pET-rhFcγRIIb described in Reference Example 1 as template DNA and oligonucleotides consisting of the sequences set forth in SEQ ID NO: 92 and SEQ ID NO: 97 as PCR primers. The error-prone PCR was carried out by preparing a reaction mixture with the composition shown in Table 22, and then heat treating the reaction mixture at 95° C. for 2 minutes, carrying out 30 cycles of reaction where one cycle consisted of a first step at 95° C. for 30 seconds, a second step at 60° C. for 30 seconds and a third step at 72° C. for 90 seconds, and finally conducting heat treatment at 72° C. for 7 minutes. The obtained PCR product was designated as EP.

TABLE 22

| Composition | Concentration/Volume |
| --- | --- |
| Template DNA | 0.05 ng/uL |
| Each PCR primer | 0.4 μM |
| MnCl$_2$ | 0.4 mM |
| dATP | 0.2 mM |
| dGTP | 0.2 mM |
| dCTP | 1 mM |
| dTTP | 1 mM |
| Buffer (MgCl$_2$ prepared to 5 mM) | 5 μL |
| GoTaq polymerase (Promega Corp.) | 0.05 U/μL |
| H$_2$O | up to 50 μL |

The DNA fragment-purified PCR product EP was digested with restriction enzymes NcoI and HindIII, and after repeating DNA fragment purification, it was linked by ligation with pETMalE21 vector that had been previously digested with restriction enzymes NcoI and HindIII, and used for transformation of *E. coli* NiCo21(DE3) by the calcium chloride method. The obtained transformant was used to form colonies in LB agar medium containing 50 μg/mL kanamycin. The transformant colonies (approximately 1800) were inoculated into 400 μL of LB medium containing 50 μg/mL kanamycin, and a 96-well deep well plate was used for aerobic shake culturing overnight at 37° C. After culturing, 20 μL of culture solution was subcultured on 600 μL of LB medium (including 0.05 mM IPTG, 0.3% (w/v) glycine and 50 μg/mL kanamycin), and a 96-well deep well plate was used for aerobic shake culturing for 24 hours at 20° C. After culturing, the culture supernatant obtained by centrifugation was taken as a sample solution. Next, the amount of soluble improved recombinant FcγRIIb in each 5-fold diluted sample solution was evaluated based on the value measured by ELISA method 1 (using a sample solution of the culture supernatant obtained by centrifugation, instead of the sample solution containing improved recombinant FcγRIIa), using 50 mM Tris-HCl buffer (pH 8.0). A transformant (hereunder referred to as "transformant a4F3") was selected out and obtained based on the evaluation results of ELISA method 1.

Extraction of recombinant vector pET-a4F3 from the transformant a4F3 and confirmation of the base sequence of the DNA (SEQ ID NO: 155) encoding improved recombinant FcγRIIb-a4F3 (SEQ ID NO: 154) and its surrounding region were carried out by the same method as described in (2) of Example 17.

(2) Preparation of Recombinant Vector pET-m3

Recombinant vector pET-m3 was prepared by the following method. The recombinant vector pET-m3 is a recombinant vector used for expression of improved recombinant FcγRIIb-m3 consisting of the amino acid sequence set forth in SEQ ID NO: 156.

PCR was carried out using the recombinant vector pET-rhFcγRIIb described in Reference Example 1 as template DNA and oligonucleotides consisting of the sequences set forth in SEQ ID NO: 92 and SEQ ID NO: 157 as PCR primers. PCR was carried out by preparing a reaction mixture with the composition shown in Table 14 and reacting the reaction mixture under the conditions shown in Table 15. The obtained PCR product was designated as m3p1.

PCR was carried out using the recombinant vector pET-a4F3 as template DNA and oligonucleotides consisting of the sequences set forth in SEQ ID NO: 158 and SEQ ID NO: 159 as PCR primers. PCR was carried out by preparing a reaction mixture with the composition shown in Table 14 and reacting the reaction mixture under the conditions shown in Table 15. The obtained PCR product was designated as m3p2.

PCR was carried out using the recombinant vector pET-rhFcγRIIb described in Reference Example 1 as template DNA and oligonucleotides consisting of the sequences set forth in SEQ ID NO: 160 and SEQ ID NO: 97 as PCR primers. PCR was carried out by preparing a reaction mixture with the composition shown in Table 14 and reacting the reaction mixture under the conditions shown in Table 15. The obtained PCR product was designated as m3p3.

The procedure was carried out by mixing the DNA fragment-purified PCR products m3p1, m3p2 and m3p3 and then preparing a reaction mixture with the composition shown in Table 16 and reacting the reaction mixture under the conditions shown in Table 17. The obtained PCR product was designated as m3p4.

PCR was carried out using the PCR product m3p4 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification to obtain DNA including a base sequence encoding the improved recombinant FcγRIIb-m3.

After digesting DNA including a base sequence encoding the improved recombinant FcγRIIb-m3 with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m3"). The recombinant vector pET-m3 was used to transform *E. coli* NiCo21(DE3) by the calcium chloride method. The obtained transformant was designated as transformant m3.

Extraction of recombinant vector pET-m3 from the transformant m3 and confirmation of the base sequence of the DNA (SEQ ID NO: 161) encoding improved recombinant FcγRIIb-m3 (SEQ ID NO: 156) and its surrounding region were carried out by the same method as described in (2) of Example 17.

(3) Preparation of Recombinant Vector pET-m3(B)

Recombinant vector pET-m3(B) was prepared by the following method. The recombinant vector pET-m3(B) is a recombinant vector used for expression of improved recombinant FcγRIIb-m3 consisting of the amino acid sequence set forth in SEQ ID NO: 156. Recombinant vector pET-m3(B) is based on recombinant vector pET-m3, being obtained by modifying the region of DNA encoding a portion of the amino acid sequence of improved recombinant FcγRIIb-m3 (from serine at position 107 to proline at position 109 from the N-terminal end of the amino acid sequence set forth in SEQ ID NO: 156) by providing a restriction enzyme BamHI recognition sequence.

PCR was carried out using the recombinant vector pET-m3 as template DNA and oligonucleotides consisting of the sequences set forth in SEQ ID NO: 92 and SEQ ID NO: 162 as PCR primers. PCR was carried out by preparing a reaction mixture with the composition shown in Table 14 and reacting the reaction mixture under the conditions shown in Table 15. The obtained PCR product was designated as m3(B)p1.

PCR was carried out using the recombinant vector pET-m3 as template DNA and oligonucleotides consisting of the sequences set forth in SEQ ID NO: 163 and SEQ ID NO: 97 as PCR primers. PCR was carried out by preparing a reaction mixture with the composition shown in Table 14 and reacting the reaction mixture under the conditions shown in Table 15. The obtained PCR product was designated as m3(B)p2.

PCR was carried out by mixing the DNA fragment-purified PCR products m3(B)p1 and m3(B)p2 and then preparing a reaction mixture with the composition shown in Table 16 and reacting the reaction mixture under the conditions shown in Table 17. The obtained PCR product was designated as m3(B)p3.

PCR was carried out using the PCR product m3(B)p3 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification to obtain DNA having the restriction enzyme BamHI recognition sequence and including a base sequence encoding the same amino acid sequence as the improved recombinant FcγRIIb-m3. After digesting this DNA with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m3(B)"). The recombinant vector pET-m3(B) was used to transform *E. coli* NiCo21(DE3) by the calcium chloride method. The obtained transformant was designated as transformant m3(B).

Extraction of recombinant vector pET-m3(B) from the transformant m3(B) and confirmation of the base sequence of the DNA (SEQ ID NO: 164) encoding improved recombinant FcγRIIb-m3 (SEQ ID NO: 156) and its surrounding region were carried out by the same method as described in (2) of Example 17.

(4) Preparation of Recombinant Vector pET-m6b

Recombinant vector pET-m6b was prepared by the following method. The recombinant vector pET-m6b is a recombinant vector used for expression of improved recombinant FcγRIIb-m6b consisting of the amino acid sequence set forth in SEQ ID NO: 165.

PCR was carried out using the recombinant vector pET-m3(B) as template DNA and oligonucleotides consisting of the sequences set forth in SEQ ID NO: 92 and SEQ ID NO: 166 as PCR primers. PCR was carried out by preparing a reaction mixture with the composition shown in Table 14 and reacting the reaction mixture under the conditions shown in Table 15. The obtained PCR product was designated as m5cp1.

PCR was carried out using the recombinant vector pET-m3(B) as template DNA and oligonucleotides consisting of the sequences set forth in SEQ ID NO: 167 and SEQ ID NO:

97 as PCR primers. PCR was carried out by preparing a reaction mixture with the composition shown in Table 14 and reacting the reaction mixture under the conditions shown in Table 15. The obtained PCR product was designated as m5cp2.

PCR was carried out by mixing the DNA fragment-purified PCR products m5cp1 and m5cp2 and then preparing a reaction mixture with the composition shown in Table 16 and reacting the reaction mixture under the conditions shown in Table 17. The obtained PCR product was designated as m5cp3.

PCR was carried out using the PCR product m5cp3 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification, and was designated as m5cp4.

PCR was carried out using the PCR product m5cp4 as template DNA and oligonucleotides consisting of the sequences set forth in SEQ ID NO: 92 and SEQ ID NO: 168 as PCR primers. PCR was carried out by preparing a reaction mixture with the composition shown in Table 14 and reacting the reaction mixture under the conditions shown in Table 15. The obtained PCR product was designated as m6bp 1.

PCR was carried out using the PCR product m5cp4 as template DNA and oligonucleotides consisting of the sequences set forth in SEQ ID NO: 169 and SEQ ID NO: 97 as PCR primers. PCR was carried out by preparing a reaction mixture with the composition shown in Table 14 and reacting the reaction mixture under the conditions shown in Table 15. The obtained PCR product was designated as m6bp2.

PCR was carried out by mixing the DNA fragment-purified PCR products m6bp1 and m6bp2 and then preparing a reaction mixture with the composition shown in Table 16 and reacting the reaction mixture under the conditions shown in Table 17. The obtained PCR product was designated as m6bp3.

PCR was carried out using the PCR product m6bp3 as template DNA and oligonucleotides consisting of the sequences set forth in SEQ ID NO: 92 and SEQ ID NO: 97 as PCR primers. PCR was carried out by preparing a reaction mixture with the composition shown in Table 14 and reacting the reaction mixture under the conditions shown in Table 15. The obtained PCR product was subjected to DNA fragment purification to obtain DNA including a base sequence encoding the improved recombinant FcγRIIb-m6b.

After digesting DNA including a base sequence encoding the improved recombinant FcγRIIb-m6b with restriction enzymes NcoI and HindIII, it was subjected to DNA fragment purification, and linked by ligation to a pETMalE21 vector that had been previously digested with restriction enzymes NcoI and HindIII, to prepare a recombinant vector (hereunder referred to as "recombinant vector pET-m6b"). The recombinant vector pET-m6b was used to transform *E. coli* NiCo21(DE3) by the calcium chloride method. The obtained transformant was designated as transformant m6b.

Extraction of recombinant vector pET-m6b from the transformant m6b and confirmation of the base sequence of the DNA (SEQ ID NO: 170) encoding improved recombinant FcγRIIb-m6b and its surrounding region were carried out by the same method as described in (2) of Example 17.

Example 20 Acid Stability of Improved Recombinant FcγRIIa-m6

The acid stability of the improved recombinant FcγRIIa-m6 of Example 17 was evaluated.

After diluting a sample solution of the soluble protein extract including the improved recombinant FcγRIIa-m6 of Example 17 with purified water to 30 μg/mL, 100 μL of the diluted sample solution was mixed with 200 μL of 0.1 M glycine hydrochloride buffer (pH 3.0), and allowed to stand at 30° C. for 24 hours, 48 hours or 72 hours.

The antibody binding activity of the protein after acid treatment with glycine hydrochloride buffer (pH 3.0) and the antibody binding activity of the protein without acid treatment were measured by ELISA method 2 described in (3) of Example 17. Next, the antibody binding activity with acid treatment was divided by the antibody binding activity without acid treatment, to calculate the residual activity.

Comparative Example 6 Acid Stability of Recombinant FcγRIIa

The recombinant FcγRIIa of Comparative Example 4 was evaluated for acid stability. The acid stability was evaluated by the same method as described in Example 20, except that a soluble protein extract including the recombinant FcγRIIa of Comparative Example 4 was used as the sample.

The evaluation results for the acid stability of improved recombinant FcγRIIa-m6 (Example 20) and recombinant FcγRIIa (Comparative Example 6) are shown in Table 23. As shown in Table 23, the improved recombinant FcγRIIa-m6 of Example 17 had higher acid stability (residual activity after acid treatment) than the recombinant FcγRIIa of Comparative Example 4. This indicates that the improved recombinant FcγRIIa-m6 has both increased thermal stability (Example 19 and Comparative Example 5) as well as increased acid stability, compared to recombinant FcγRIIa.

TABLE 23

| Example or Comp. Example | Sample name | SEQ ID NO: | Amino acid substitution | Residual acid resistance activity (%) | | | |
|---|---|---|---|---|---|---|---|
| | | | | 0 hours | 24 hours | 48 hours | 72 hours |
| Example 17 | Improved recombinant FcγRIIa-m6 | 89 | Substitution (7), substitution (8), substitution (9), substitution (10), substitution (11), substitution (12) | 100.0 | 100.0 | 81.1 | 76.0 |
| Comp. Example 4 | Recombinant FcγRIIa | 88 | | 100.0 | 7.8 | 0.0 | 0.0 |

Example 21 Preparation of Cysteine Tag-Added Improved Recombinant FcγRIIa-Am6_Cys (1) PCR was carried out using as the template an expression vector pET-Am6 including the polynucleotide set forth in SEQ ID NO: 91 encoding a protein consisting of the amino acid sequence set forth in SEQ ID NO: 89, prepared in Example 17. The PCR primers used were oligonucleotides consisting of the sequences set forth in SEQ ID NO: 171 (5'-TAGCCATGGGCATGCGTACCGAAGATCTG-CCGAAAGC-3') and SEQ ID NO: 172 (5'-CCCAAGCT-TATCCGCAGGTATCGTTGCGGCAGCCCTGCACGGT-GATAGTAACCGGCT TGCTGCTATA-3'). The PCR was conducted by preparing a reaction mixture with the composition shown in Table 14, and then heat treating the reaction mixture at 98° C. for 5 minutes, and repeating 30 cycles of a reaction where one cycle consisted of a first step at 98° C. for 10 seconds, a second step at 55° C. for 5 seconds and a third step at 72° C. for 1 minute.

(2) The polynucleotide obtained in (1) was purified and digested with restriction enzymes NcoI and HindIII, and then ligated with expression vector pTrc-PelBV3 constructed by the method described in WO2015/199154, which had been previously digested with restriction enzymes NcoI and HindIII, and the ligation product was used to transform *E. coli* W3110.

(3) The obtained transformants were cultured in LB medium containing 100 μg/mL carbenicillin, and then a QIAprep Spin Miniprep kit (product of Qiagen Inc.) was used to obtain expression vector pTrc-Am6_Cys.

(4) The nucleotide sequence of pTrc-Am6_Cys was analyzed in the same manner as (2) of Example 17, except that the oligonucleotide consisting of the sequence set forth in SEQ ID NO: 173 (5'-TGTGGTATGGCTGTGCAGG-3') or SEQ ID NO: 174 (5'-TCGGCATGGGGTCAGGTG-3') was used as the sequencing primer.

The amino acid sequence of polypeptide FcγRIIa-Am6_Cys expressed by expression vector pTrc-Am6_Cys is set forth in SEQ ID NO: 175, and the sequence of the polynucleotide encoding the polypeptide is set forth in SEQ ID NO: 176. In the amino acid sequence set forth in SEQ ID NO: 175, the amino acid residues from methionine at position 1 to alanine at position 22 are the PelB signal peptide, methionine at position 23 and glycine at position 24 are linkers, the amino acid residues from glutamine at position 25 to glutamine at position 197 are the improved FcγRIIa extracellular domain (corresponding to the amino acid residues from glutamine at position 29 to glutamine at position 201 in the amino acid sequence set forth in SEQ ID NO: 89), glycine at position 198 and cysteine at position 199 are linkers, and the amino acid residues from arginine at position 200 to glycine at position 205 are a cysteine tag. Among the amino acid substitutions in the improved FcγRIIa extracellular domain, valine at position 68 (substitution (7)) of SEQ ID NO: 89 corresponds to position 64 in SEQ ID NO: 175, glutamine at position 80 (substitution (8)) of SEQ ID NO: 89 corresponds to position 76 in SEQ ID NO: 175, threonine at position 84 (substitution (9)) of SEQ ID NO: 89 corresponds to position 80 in SEQ ID NO: 175, threonine at position 90 (substitution (10)) of SEQ ID NO: 89 corresponds to position 86 in SEQ ID NO: 175, serine at position 91 (substitution (11)) of SEQ ID NO: 89 corresponds to position 87 in SEQ ID NO: 175, and arginine at position 125 (substitution (12)) of SEQ ID NO: 89 corresponds to position 121 in SEQ ID NO: 175.

Example 22 Preparation of Cysteine Tag-Added Improved Recombinant FcγRIIa-Am6_Cys (1) Transformants expressing the cysteine tag-added improved recombinant FcγRIIa-Am6_Cys constructed in Example 21 were inoculated into 400 mL of 2YT liquid medium (16 g/L peptone, 10 g/L yeast extract and 5 g/L sodium chloride) containing 100 μg/mL carbenicillin in a 2 L baffle flask, and aerobically shake cultured overnight at 37° C., as preculturing.

(2) After inoculating 180 mL of the culture solution of (7) into 1.8 L of liquid medium containing 10 g/L glucose, 20 g/L yeast extract, 3 g/L trisodium phosphate dodecahydrate, 9 g/L disodium hydrogenphosphate dodecahydrate, 1 g/L ammonium chloride and 100 mg/L carbenicillin, a 3 L fermenter (product of Biott) was used for main culturing. The conditions were set to a temperature of 30° C., a pH of 6.9 to 7.1, an aeration rate of 1 VVM and a dissolved oxygen concentration at 30% saturated concentration, and main culturing was commenced. For pH regulation, 50% phosphoric acid was used as the acid and 14% (w/v) ammonia water was used as the alkali, the dissolved oxygen was controlled by varying the stirring speed, and the stirring rotational speed was set with a lower limit of 500 rpm and an upper limit of 1000 rpm. After the start of culturing, and when the glucose concentration was no longer measurable, feeding culture medium (248.9 g/L glucose, 83.3 g/L yeast extract, 7.2 g/L magnesium sulfate heptahydrate) was added while controlling the dissolved oxygen (DO).

(3) When the absorbance at 600 nm (OD600 nm) reached about 150 as a measure of the cell mass, the culturing temperature was lowered to 25° C., and upon confirming that the preset temperature had been reached, IPTG was added to a final concentration of 0.5 mM and culturing was continued at 25° C.

(4) Culturing was terminated at about 48 hours after the start of culturing, and the cells were recovered by centrifugation of the culture solution at 8000 rpm for 20 minutes at 4° C.

(5) The collected cells were suspended in 20 mM Tris-HCl buffer (pH 7.0) to 5 mL/1 g-cells, and an ultrasonic generator (INSONATOR 201M, product of Kubota Corp.) was used to disrupt the cells at 4° C. for about 10 minutes, with an output of about 150 W. The cell disruptate was centrifuged twice at 4° C. for 20 minutes, 8000 rpm, and the supernatant was collected.

(6) The supernatant obtained in (5) was applied to a VL32×250 column (Merck, Ltd. Millipore) packed with 140 mL of TOYOPEARL CM-650 M (Tosoh Corp.) that had been previously equilibrated with 20 mM phosphate buffer (8 mM sodium dihydrogenphosphate, 12 mM disodium hydrogenphosphate) (pH 7.0), at a flow rate of 5 mL/min. After rinsing with the buffer used for equilibration, it was eluted with 20 mM phosphate buffer (pH 7.0) containing 0.5 M sodium chloride.

(7) The eluate obtained in (6) was applied to an XK26/20 column (product of GE Healthcare) packed with 90 mL of IgG Sepharose (product of GE Healthcare) that had been previously equilibrated with 20 mM Tris-HCl buffer (pH 7.4) containing 150 mM sodium chloride. After rinsing with the buffer used for equilibration, elution was performed with 0.1 M glycine hydrochloride buffer (pH 3.0). The eluate was restored to nearly neutral pH by addition of 1 M Tris-HCl buffer (pH 8.0) at ¼ the volume of the eluate.

The purification yielded approximately 20 mg of high-purity cysteine tag-added improved recombinant FcγRIIa-Am6_Cys.

Example 23 Preparation of Improved Recombinant FcγRIIa-Am6_Cys Immobilized Gel and Evaluation of Separation Performance (1) After activating the hydroxyl groups on the surface of 2 mL of a hydrophilic vinyl polymer for separation (Tosoh Corp.) using iodoacetyl groups, 4 mg of the cysteine tag-added improved recombinant FcγRIIa-Am6_Cys prepared in Example 22 was reacted, to obtain a FcγRIIa-Am6 immobilized gel.

(2) A FcγRIIa-Am6 column was prepared by packing a φ4.6 mm×75 mm stainless steel column with 1.2 mL of the FcγRIIa-Am6 immobilized gel prepared in (1).

(3) The FcγRIIa-Am6 column prepared in (2) was connected to a high-performance liquid chromatography apparatus (Tosoh Corp.) and equilibrated with 50 mM Tris-glycine buffer (pH 8.5) as equilibrating buffer.

(4) Monoclonal antibody diluted to 1.0 mg/mL with PBS (Phosphate Buffered Saline) (pH 7.4) (Rituxan, (Zenyaku Kogyo), bevacizumab; infliximab) and polyclonal antibody (human immunoglobulin) were added at 5 μL at a flow rate of 0.6 mL/min.

(5) After rinsing for 10 minutes with equilibrating buffer while maintaining a flow rate of 0.6 mL/min, the monoclonal antibody adsorbed with a pH gradient produced with 50 mM Tris-glycine buffer (pH 3.0) (a gradient for 100% 50 mM Tris-glycine buffer (pH 3.0) in 30 minutes) was eluted.

Figure 3:
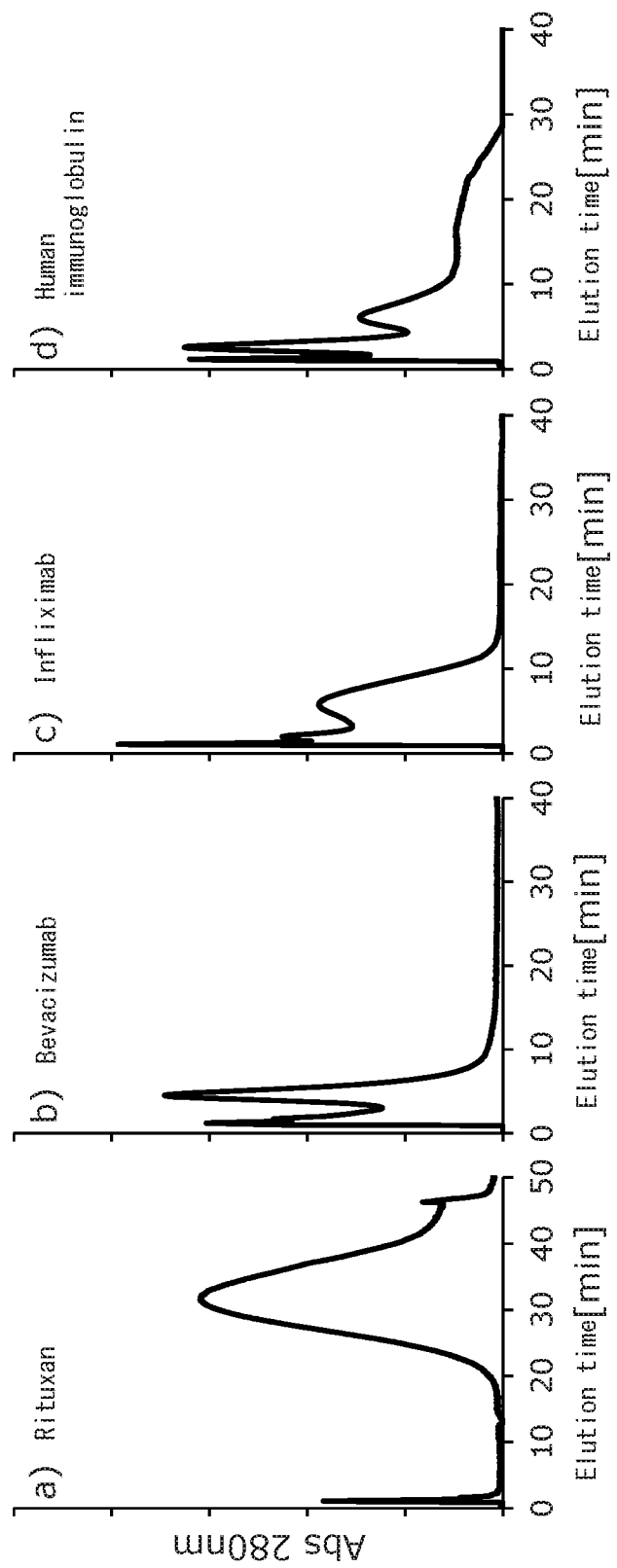
FIG. 3 is a set of chromatograms showing the results of separating different antibodies using a column packed with insoluble support immobilizing the improved recombinant FcγRIIa of the invention.

The result (elution pattern) is shown in FIG. 3. The results in FIG. 3 are for applying a) Rituxan, b) bevacizumab, c) infliximab and d) human immunoglobulin to the FcγRIIa-Am6 column. Since the structure of each antibody (amino acid sequence or attached sugar chain structure) differs depending on differences in the type of monoclonal antibody or polyclonal antibody, the differences in their structure contribute to interaction with Fc-binding protein, with each antibody being separated into a different peak.

INDUSTRIAL APPLICABILITY

Improved recombinant FcγRIIb and FcγRIIa according to the invention is useful as a ligand for affinity chromatography, to be used for purification or analysis of diagnostic reagent-containing drugs, biochemical reagents, and IgG.

Sequence Listing Free Text

The invention claimed is:
1. An improved recombinant FcγRII selected from the following (i) to (iii):
   (i) Improved recombinant FcγRIIb comprising at least the amino acid residues from position 29 to position 201 of the amino acid sequence set forth in SEQ ID NO: 1, wherein at least one of the following amino acid substitutions (1) to (6) is included in the amino acid residues from position 29 to position 201:
   (1) A substitution of valine for isoleucine at position 68 of SEQ ID NO: 1;
   (2) A substitution of glutamine for histidine at position 80 of SEQ ID NO: 1;
   (3) A substitution of threonine for serine at position 84 of SEQ ID NO: 1;
   (4) A substitution of threonine for asparagine at position 90 of SEQ ID NO: 1;
   (5) A substitution of serine for asparagine at position 91 of SEQ ID NO: 1;
   (6) A substitution of arginine for histidine at position 125 of SEQ ID NO: 1;
   (ii) Improved recombinant FcγRIIa comprising at least the amino acid residues from position 29 to position 201 of the amino acid sequence set forth in SEQ ID NO: 88, wherein at least one of the following amino acid substitutions (7) to (12) are included in the amino acid residues from position 29 to position 201:
   (7) A substitution of valine for isoleucine at position 68 of SEQ ID NO: 88;
   (8) A substitution of glutamine for histidine at position 80 of SEQ ID NO: 88;
   (9) A substitution of threonine for serine at position 84 of SEQ ID NO: 88;
   (10) A substitution of threonine for asparagine at position 90 of SEQ ID NO: 88;
   (11) A substitution of serine for asparagine at position 91 of SEQ ID NO: 88;
   (12) A substitution of arginine for histidine at position 125 of SEQ ID NO: 88;
   (iii) Improved recombinant FcγRII consisting of an amino acid sequence of the improved recombinant FcγRII of the above (i) or (ii) in which one or more amino acid residues in a region other than positions substituted by the substitutions (1) to (12) have been deleted, substituted or added, and having affinity for IgG.
2. The improved recombinant FcγRII according to claim 1, which is the improved recombinant FcγRII selected from the following (iv) to (vi):
   (iv) Improved recombinant FcγR11b comprising at least the amino acid residues from position 29 to position 201 of the amino acid sequence set forth in SEQ ID NO: 1, wherein at least the following amino acid substitution (1) is included in the amino acid residues from position 29 to position 201:
   (1) A substitution of valine for isoleucine at position 68 of SEQ ID NO: 1;
   (v) Improved recombinant FcγRIIa comprising at least the amino acid residues from position 29 to position 201 of the amino acid sequence set forth in SEQ ID NO: 88, wherein at least the following amino acid substitution (7) is included in the amino acid residues from position 29 to position 201:
   (7) A substitution of valine for isoleucine at position 68 of SEQ ID NO: 88;
   (vi) Improved recombinant FcγRII consisting of an amino acid sequence of the improved recombinant FcγRII of the above (iv) or (v) in which one or more amino acid residues in a region other than the position substituted by the substitution (1) or (7) have been deleted, substituted or added, and having affinity for IgG.
3. The improved recombinant FcγRII according to claim 1, which is selected from the following (vii) to (ix):
   (vii) Improved recombinant FcγRIIb comprising at least the amino acid residues from position 29 to position 201 of the amino acid sequence set forth in any one of SEQ ID NOs: 2 to 11;
   (viii) Improved recombinant FcγRIIa comprising at least the amino acid residues from position 29 to position 201 of the amino acid sequence set forth in SEQ ID NO: 89;
   (ix) Improved recombinant FcγRII consisting of an amino acid sequence of the improved recombinant FcγRII of the above (vii) or (viii) in which one or more amino acid residues in a region other than positions substituted by the substitutions (1) to (12) have been deleted, substituted or added, and having affinity for IgG.
4. DNA encoding the improved recombinant FcγRII according to claim 1.
5. A recombinant vector comprising the DNA according to claim 4.
6. A transformant capable of producing an improved recombinant FcγRII, obtained by transforming a host with the recombinant vector according to claim 5.
7. The transformant according to claim 6, wherein the host is *E. coli*.
8. A method for producing an improved recombinant FcγRII, comprising two steps of: culturing the transformant according to claim 6 to produce the improved recombinant FcγRII; and collecting the improved recombinant FcγRII that is produced from the obtained cultured product.
9. An adsorbent obtained by immobilizing the improved recombinant FcγRII according to claim 1 on an insoluble support.
10. A method for separating an antibody, comprising two steps of: adding an antibody-containing solution to a column packed with the adsorbent according to claim 9, thereby adsorbing the antibody onto the adsorbent; and eluting the adsorbed antibody by use of an eluent.

* * * * *